US011578359B2

(12) United States Patent
Weng et al.

(10) Patent No.: US 11,578,359 B2
(45) Date of Patent: Feb. 14, 2023

(54) METHODS AND COMPOSITIONS FOR ENRICHMENT OF AMPLIFICATION PRODUCTS

(71) Applicant: ACCURAGEN HOLDINGS LIMITED, Grand Cayman (KY)

(72) Inventors: Li Weng, Fremont, CA (US); Shengrong Lin, Fremont, CA (US); Ling Fung Tang, San Francisco, CA (US)

(73) Assignee: ACCURAGEN HOLDINGS LIMITED, George Town (KY)

(*) Notice: Subject to any disclaimer, the term of this patent is extended or adjusted under 35 U.S.C. 154(b) by 148 days.

(21) Appl. No.: 16/927,898

(22) Filed: Jul. 13, 2020

(65) Prior Publication Data
US 2021/0002716 A1 Jan. 7, 2021

Related U.S. Application Data

(63) Continuation of application No. 15/947,100, filed on Apr. 6, 2018, now Pat. No. 10,752,942, which is a continuation of application No. PCT/US2016/056126, filed on Oct. 7, 2016.

(60) Provisional application No. 62/239,690, filed on Oct. 9, 2015.

(51) Int. Cl.
*C12Q 1/6853* (2018.01)
*C12Q 1/6858* (2018.01)
*C12Q 1/68* (2018.01)
*G16B 25/00* (2019.01)
*G16B 25/20* (2019.01)

(52) U.S. Cl.
CPC .......... *C12Q 1/6853* (2013.01); *C12Q 1/68* (2013.01); *C12Q 1/6858* (2013.01); *G16B 25/00* (2019.02); *G16B 25/20* (2019.02)

(58) Field of Classification Search
CPC ........ C12Q 1/68; C12Q 1/6844; C12Q 1/686; C12Q 2525/307; C12P 19/34; C07H 21/00; G16B 25/00; G16B 25/20
See application file for complete search history.

(56) References Cited

U.S. PATENT DOCUMENTS

| | | |
|---|---|---|
| 5,130,238 A | 7/1992 | Malek et al. |
| 5,234,809 A | 8/1993 | Boom et al. |
| 5,270,184 A | 12/1993 | Walker et al. |
| 5,310,652 A | 5/1994 | Gelfand et al. |
| 5,322,770 A | 6/1994 | Gelfand |
| 5,330,892 A | 7/1994 | Vogelstein et al. |
| 5,352,775 A | 10/1994 | Albertsen et al. |
| 5,362,623 A | 11/1994 | Vogelstein et al. |
| 5,399,491 A | 3/1995 | Kacian et al. |
| 5,455,166 A | 10/1995 | Walker |
| 5,480,784 A | 1/1996 | Kacian et al. |
| 5,492,808 A | 2/1996 | de la Chapelle et al. |
| 5,494,810 A | 2/1996 | Barany et al. |
| 5,527,670 A | 6/1996 | Stanley |
| 5,527,676 A | 6/1996 | Vogelstein et al. |
| 5,545,540 A | 8/1996 | Mian |
| 5,571,905 A | 11/1996 | Vogelstein et al. |
| 5,576,422 A | 11/1996 | Vogelstein et al. |
| 5,591,826 A | 1/1997 | de la Chapelle et al. |
| 5,648,212 A | 7/1997 | Albertsen et al. |
| 5,648,245 A | 7/1997 | Fire et al. |
| 5,691,454 A | 11/1997 | Albertsen et al. |
| 5,693,470 A | 12/1997 | de la Chapelle et al. |
| 5,693,536 A | 12/1997 | Vogelstein et al. |
| 5,705,365 A | 1/1998 | Ryder et al. |
| 5,705,628 A | 1/1998 | Hawkins |
| 5,710,029 A | 1/1998 | Ryder et al. |
| 5,783,666 A | 7/1998 | Albertsen et al. |
| 5,807,692 A | 9/1998 | Kinzler et al. |
| 5,830,676 A | 11/1998 | Vogelstein et al. |
| 5,830,711 A | 11/1998 | Barany et al. |
| 5,837,443 A | 11/1998 | de la Chapelle et al. |
| 5,854,033 A | 12/1998 | Lizardi |
| 5,871,925 A | 2/1999 | de la Chapelle et al. |

(Continued)

FOREIGN PATENT DOCUMENTS

| | | |
|---|---|---|
| AU | 9057901 A | 3/2002 |
| CN | 101985654 A | 3/2011 |

(Continued)

OTHER PUBLICATIONS

Dean et al., Rapid Amplification of Plasmid and Phage DNA Using Phi29 DNA Polymerase and Multiply-Primed Rolling Circle Amplification. Genome Research 11: 1095-1099 (Year: 2001).*
Dillon et al., Cell Reports 11:1749-1759 (Jun. 2015) (Year: 2015).*
Faham et al., Deep-sequencing approach for minimal residual disease detection in acute lymphoblastic leukemia. Blood 120 (26): 5173 (Year: 2012).*
Huang, SH. Inverse Polymerase Chain Reaction. Molecular Biotechnology 2 : 15 (Year: 1994).*
Lroenlein et al., Genes, Chromosomes & Cancer 51 : 290-299 (Year: 2012).*
Kumar et al., Molecular Cancer Reseatch 15(9): 1197-1205 (Year: 2017).*

(Continued)

*Primary Examiner* — Ethan C Whisenant
(74) *Attorney, Agent, or Firm* — Wilson Sonsini Goodrich & Rosati

(57) ABSTRACT

In some aspects, the present disclosure provides methods for enriching amplicons, or amplification products, comprising a concatemer of at least two or more copies of a target polynucleotide. In some embodiments, a method comprises sequencing the amplicons comprising at least two or more copies of a target polynucleotide. In some embodiments, the target polynucleotides comprise sequences resulting from chromosome rearrangement, including but not limited to point mutations, single nucleotide polymorphisms, insertions, deletions, and translocations including fusion genes. In some aspects, the present disclosure provides compositions and reaction mixtures useful in the described methods.

22 Claims, 11 Drawing Sheets

Specification includes a Sequence Listing.

(56) References Cited

U.S. PATENT DOCUMENTS

| | | |
|---|---|---|
| 5,871,968 A | 2/1999 | Kinzler et al. |
| 5,888,779 A | 3/1999 | Kacian et al. |
| 5,939,291 A | 8/1999 | Loewy et al. |
| 5,942,391 A | 8/1999 | Zhang et al. |
| 5,955,263 A | 9/1999 | Vogelstein et al. |
| 6,033,850 A | 3/2000 | Purvis |
| RE36,713 E | 5/2000 | Vogelstein et al. |
| 6,090,566 A | 7/2000 | Vogelstein et al. |
| 6,114,124 A | 9/2000 | Albertsen et al. |
| 6,143,495 A | 11/2000 | Lizardi et al. |
| 6,156,504 A | 12/2000 | Gocke et al. |
| 6,210,891 B1 | 4/2001 | Nyren et al. |
| 6,245,515 B1 | 6/2001 | Vogelstein et al. |
| 6,251,639 B1 | 6/2001 | Kurn |
| 6,277,605 B1 | 8/2001 | Wijnhoven et al. |
| 6,300,059 B1 | 10/2001 | Vogelstein et al. |
| 6,333,157 B1 | 12/2001 | Miller-Jones et al. |
| 6,380,369 B1 | 4/2002 | Adams et al. |
| 6,410,278 B1 | 6/2002 | Notomi et al. |
| 6,413,727 B1 | 7/2002 | Albertsen et al. |
| 6,416,984 B1 | 7/2002 | Haseltine et al. |
| 6,482,606 B1 | 11/2002 | Adams et al. |
| 6,511,805 B1 | 1/2003 | Gocke et al. |
| 6,521,409 B1 | 2/2003 | Gocke et al. |
| 6,569,647 B1 | 5/2003 | Zhang et al. |
| 6,593,086 B2 | 7/2003 | Zhang |
| 6,610,477 B1 | 8/2003 | Haseltine et al. |
| 6,620,619 B2 | 9/2003 | Haseltine et al. |
| 6,677,312 B1 | 1/2004 | Vogelstein et al. |
| 6,800,617 B1 | 10/2004 | Vogelstein et al. |
| 6,815,167 B2 | 11/2004 | Crothers et al. |
| 6,833,246 B2 | 12/2004 | Balasubramanian |
| 6,917,726 B2 | 7/2005 | Levene et al. |
| 6,939,675 B2 | 9/2005 | Gocke et al. |
| 6,946,251 B2 | 9/2005 | Kurn |
| RE38,916 E | 12/2005 | Vogelstein et al. |
| 6,977,148 B2 | 12/2005 | Dean et al. |
| 7,001,724 B1 | 2/2006 | Greenfield |
| 7,033,764 B2 | 4/2006 | Korlach et al. |
| 7,052,847 B2 | 5/2006 | Korlach et al. |
| 7,056,676 B2 | 6/2006 | Korlach et al. |
| 7,087,583 B2 | 8/2006 | Vogelstein et al. |
| 7,170,050 B2 | 1/2007 | Turner et al. |
| 7,183,053 B2 | 2/2007 | Gocke et al. |
| 7,208,275 B2 | 4/2007 | Gocke et al. |
| 7,267,955 B2 | 9/2007 | Vogelstein et al. |
| 7,282,335 B2 | 10/2007 | Gocke et al. |
| 7,288,380 B1 | 10/2007 | Gocke et al. |
| 7,326,778 B1 | 2/2008 | de la Chapelle et al. |
| 7,361,466 B2 | 4/2008 | Korlach et al. |
| 7,387,874 B2 | 6/2008 | Gocke et al. |
| 7,399,592 B2 | 7/2008 | Gocke et al. |
| 7,410,764 B2 | 8/2008 | Gocke et al. |
| 7,416,844 B2 | 8/2008 | Korlach et al. |
| 7,553,619 B2 | 6/2009 | Kumar et al. |
| 7,569,349 B2 | 8/2009 | Gocke et al. |
| 7,569,350 B2 | 8/2009 | Gocke et al. |
| RE40,948 E | 10/2009 | Vogelstein et al. |
| 7,700,286 B2 | 4/2010 | Stroun et al. |
| RE41,327 E | 5/2010 | Gocke et al. |
| 7,790,395 B2 | 9/2010 | Gocke et al. |
| 7,824,890 B2 | 11/2010 | Hoser et al. |
| 7,935,484 B2 | 5/2011 | Gocke et al. |
| 7,935,487 B2 | 5/2011 | Gocke et al. |
| 7,972,817 B2 | 7/2011 | Kopreski |
| 8,048,629 B2 | 11/2011 | Gocke et al. |
| 8,209,130 B1 | 6/2012 | Kennedy et al. |
| 8,361,726 B2 | 1/2013 | Gocke et al. |
| 8,563,477 B2 | 10/2013 | Smith et al. |
| RE44,596 E | 11/2013 | Stroun et al. |
| 8,835,358 B2 | 9/2014 | Fodor et al. |
| 9,217,167 B2 | 12/2015 | Heller et al. |
| 10,155,980 B2 | 12/2018 | Weng et al. |
| 10,443,087 B2 | 10/2019 | Rigatti et al. |
| 10,724,088 B2 | 7/2020 | Weng et al. |
| 10,752,942 B2 * | 8/2020 | Weng .................. C12Q 1/6853 |
| 10,767,222 B2 | 9/2020 | Lin et al. |
| 2002/0042061 A1 | 4/2002 | Yang et al. |
| 2002/0168645 A1 | 11/2002 | Taylor |
| 2003/0032024 A1 | 2/2003 | Lizardi |
| 2003/0100077 A1* | 5/2003 | Korte .................. C12N 15/8213 435/6.12 |
| 2004/0058378 A1 | 3/2004 | Kong et al. |
| 2004/0067511 A1* | 4/2004 | Thomas ............... C12Q 1/6844 435/6.12 |
| 2006/0228721 A1 | 10/2006 | Leamon et al. |
| 2007/0020646 A1* | 1/2007 | Hoon .................. G01N 33/5011 435/6.1 |
| 2007/0087362 A1 | 4/2007 | Church et al. |
| 2007/0099208 A1 | 5/2007 | Drmanac et al. |
| 2007/0134128 A1 | 6/2007 | Korlach |
| 2008/0021205 A1 | 1/2008 | Blau et al. |
| 2008/0039417 A1 | 2/2008 | Wang et al. |
| 2008/0160511 A1 | 7/2008 | Dawson et al. |
| 2009/0099041 A1 | 4/2009 | Church et al. |
| 2009/0136924 A1* | 5/2009 | Larionov ................ C12N 15/85 435/320.1 |
| 2010/0075384 A1 | 3/2010 | Kong et al. |
| 2010/0115744 A1 | 5/2010 | Fong |
| 2010/0291548 A1 | 11/2010 | Sharaf et al. |
| 2010/0304989 A1 | 12/2010 | Von et al. |
| 2011/0003705 A1 | 1/2011 | Lowe et al. |
| 2011/0151438 A9 | 6/2011 | Nautiyal et al. |
| 2011/0237444 A1 | 9/2011 | Clancy et al. |
| 2011/0288284 A1 | 11/2011 | Makarov |
| 2011/0319299 A1 | 12/2011 | Osborne et al. |
| 2012/0115744 A1 | 5/2012 | Raymond |
| 2012/0157326 A1 | 6/2012 | Tisi et al. |
| 2012/0164651 A1* | 6/2012 | Kazakov ............. C12Q 1/6844 435/6.12 |
| 2013/0217023 A1 | 8/2013 | Godwin et al. |
| 2013/0224740 A1 | 8/2013 | Thierry et al. |
| 2013/0244873 A1 | 9/2013 | Wang et al. |
| 2013/0331288 A1 | 12/2013 | Gunderson et al. |
| 2014/0051154 A1 | 2/2014 | Hyland et al. |
| 2014/0066317 A1 | 3/2014 | Talasaz |
| 2014/0121116 A1 | 5/2014 | Richards et al. |
| 2014/0154683 A1 | 6/2014 | Vogelstein et al. |
| 2014/0221329 A1 | 8/2014 | Cronin et al. |
| 2014/0227705 A1 | 8/2014 | Vogelstein et al. |
| 2014/0234850 A1 | 8/2014 | Zhang et al. |
| 2014/0274740 A1 | 9/2014 | Srinivasan et al. |
| 2014/0295498 A1 | 10/2014 | Turner et al. |
| 2014/0296081 A1 | 10/2014 | Diehn et al. |
| 2014/0336236 A1 | 11/2014 | Cronin et al. |
| 2015/0031035 A1 | 1/2015 | Kvam et al. |
| 2015/0033372 A1* | 1/2015 | Bradley ................. C07K 16/00 435/328 |
| 2015/0044687 A1 | 2/2015 | Schmitt et al. |
| 2015/0111789 A1 | 4/2015 | Betts et al. |
| 2015/0126376 A1 | 5/2015 | Bielas et al. |
| 2015/0133391 A1 | 5/2015 | De Vlaminick et al. |
| 2015/0141292 A1 | 5/2015 | Fodor et al. |
| 2015/0147815 A1 | 5/2015 | Babiarz et al. |
| 2015/0315636 A1 | 11/2015 | Nadeau et al. |
| 2015/0361492 A1 | 12/2015 | Vogelstein et al. |
| 2015/0366866 A1 | 12/2015 | Ali et al. |
| 2016/0040229 A1 | 2/2016 | Talasaz et al. |
| 2016/0145691 A1 | 5/2016 | Cronin et al. |
| 2016/0201135 A1 | 7/2016 | Cronin et al. |
| 2016/0319345 A1 | 11/2016 | Gnerre et al. |
| 2017/0204456 A1 | 7/2017 | Nobile et al. |
| 2017/0362639 A1 | 12/2017 | Wilson |
| 2018/0363039 A1 | 12/2018 | Weng et al. |
| 2018/0363052 A1 | 12/2018 | Schmitt et al. |
| 2019/0241935 A1 | 8/2019 | Makarov et al. |
| 2019/0300949 A1 | 10/2019 | Weng et al. |
| 2019/0323073 A1 | 10/2019 | Lin et al. |
| 2020/0010883 A1 | 1/2020 | Weng et al. |

(56) References Cited

U.S. PATENT DOCUMENTS

| | | | |
|---|---|---|---|
| 2020/0010884 A1 | 1/2020 | Faham et al. | |
| 2020/0080141 A1 | 3/2020 | Weng et al. | |

FOREIGN PATENT DOCUMENTS

| | | | |
|---|---|---|---|
| CN | 102625850 A | 8/2012 | |
| CN | 103717752 A | 4/2014 | |
| CN | 104745679 A | 7/2015 | |
| EP | 0684315 A1 | 11/1995 | |
| EP | 0518650 B1 | 1/1997 | |
| EP | 0390323 B1 | 12/1998 | |
| EP | 0929694 A1 | 7/1999 | |
| EP | 0580596 B1 | 7/2000 | |
| EP | 0569527 B1 | 3/2001 | |
| EP | 0730648 B1 | 8/2004 | |
| EP | 2396430 B1 | 5/2013 | |
| EP | 2828218 A1 | 1/2015 | |
| EP | 3080298 B1 | 10/2018 | |
| JP | 2002503948 A | 2/2002 | |
| JP | 2002538840 A | 11/2002 | |
| JP | 2004512134 A | 4/2004 | |
| JP | 2006516410 A | 7/2006 | |
| JP | 2011505161 A | 2/2011 | |
| JP | 2013143966 A | 7/2013 | |
| JP | 2014138597 A | 7/2014 | |
| WO | WO-9844151 A1 | 10/1998 | |
| WO | WO-0049176 A1 | 8/2000 | |
| WO | WO-0118230 A1 | 3/2001 | |
| WO | WO-0120035 A2 | 3/2001 | |
| WO | WO-0138580 A2 | 5/2001 | |
| WO | WO-2007133703 A2 | 11/2007 | |
| WO | WO-2007140417 A2 | 12/2007 | |
| WO | WO-2007140417 A3 | 2/2008 | |
| WO | WO-2007024653 A3 | 4/2008 | |
| WO | WO-2008070352 A3 | 10/2008 | |
| WO | WO-2013074632 A1 | 5/2013 | |
| WO | WO-2013142389 A1 | 9/2013 | |
| WO | WO-2013181170 A1 | 12/2013 | |
| WO | WO-2013181276 A1 | 12/2013 | |
| WO | WO-2014014498 A1 | 1/2014 | |
| WO | WO-2014015084 A2 | 1/2014 | |
| WO | WO-2014145128 A2 | 9/2014 | |
| WO | WO-2015079042 A1 | 6/2015 | |
| WO | WO-2015089333 A1 | 6/2015 | |
| WO | WO-2015100427 A1 | 7/2015 | |
| WO | WO-2016053638 A1 | 4/2016 | |
| WO | WO-2017062863 A1 | 4/2017 | |
| WO | WO-2017096322 A1 | 6/2017 | |
| WO | WO-2017201102 A1 | 11/2017 | |
| WO | WO-2017223366 A1 | 12/2017 | |
| WO | WO-2018035170 A1 | 2/2018 | |

OTHER PUBLICATIONS

Li et al., Analytical Chemistry 85 :11174-11179 (Year: 2013).*
Liu et al., Cancer Research 64:2544-2551 (Year: 2004).*
Mitchell et al., PPNAS 105(30) :10513-10518 (Year: 2008).*
Nelson et al. Biotechniques 32 : S44-S47 (Year: 2002).*
Ochman et al., Genetics 120: 621-623 (Year: 1988).*
Pavlopoulos, A. Methods in Molecular Biology 772(Ch. 16) :267-275 (Year: 2011).*
Schubert et al., Virus Research 127: 61-70 (Year: 2007).*
Shibata et al., Science 336 : 82 (Year: 2012).*
Zhang et al. Gene 211:277-285 (Year: 1998).*
Tsaftaris et al. Rolling circle amplification of genomic templates for inversePCR (RCA-GIP): a method for 5'- and 3'-genome walking. Biotechnol. Letters 32 :157-161 (Year: 2010).*
Ali et al., Rolling circle amplification: a versatile tool for chemical biology, materials science and medicine. Chem Soc Rev 43(10): 3324-3341 (2014).
Amado, et al. Wild-type KRAS is required for panitumumab efficacy in patients with metastic colorectal cancer. Journal of Clinical Oncology. Apr. 1, 2008; 26(10);1626-1634.
Awuah, et al. Thermal inactivation kinetics of trypsin at aseptic processing temperatures. Journal of food process engineering 1993 v.16 No. 4 pp. 315-328 (abstract).
Blast. Basic local alignment search tool. Available at http://blast.ncbi.nlm.nih.gov/Blast.cgi. Accessed on Oct. 10, 2016.
Bokemeyer, et al. Fluorouracil, leucovorin, and oxaliplatin with and without cetuximab in the first-line treatment of metastatic colorectal cancer. Journal of Clinical Oncology. Feb. 10, 2009; 27(5).: 663-671.
Brenner. A cultivated taste for yeast. Genome Biol. 2000;1(1):Reviews103. Epub Apr. 27, 2000.
Brenner, C. Chemical genomics in yeast. Genome Biology. 2004; 5:240.
Brietbach et al. Direct Quantification of Cell-Free, Circulating DNA from Unpurified Plasma. PLoS One 9(3):1-11 (2014).
Creating Standard Curves with Genomic DNA or Plasmid DNA Templates for Use in Quantitative PCR. Applied Biosystems 2003. Downloaded Oct. 17, 2017. URL: http://www6.appliedbiosystems.com/support/tutorials/pdf/quant_pcr.pdf.
Dawson, et al., Analysis of circulating tumor DNA to monitor metastatic breast cancer. The New England Journal of Medicine. Mar. 28, 2013. 368(13); 1199-1209.
Delcher, et al. Alignment of whole genomes. Nucleic Acids Research. Feb. 2, 1999; 27(11): 2369-2376.
Devonshire, Alison S. et al. Towards standardisation of cell-free DNA measurement in plasma: controls for extraction efficiency, fragment size bias and quantification, Analytical and Bioanalytical Chemistry, 406(26): 6499-6512 (2014).
Dicker, et al. The detection of TP53 mutations in chronic lymphocytic leukemia independently predicts rapid disease progression and is highly correlated with a complex aberrant karyotype. Leukemia. Jan. 2009; 23(1):117-124.:.
Eason, et al. Characterization of synthetic DNA bar codes in *Saccharomyces cerevisiae* gene-deletion strains. Proc Natl Acad Sci U S A. Jul. 27, 2004; 101(30): 11046-11051.
EMBOSS. EMBOSS Water: Pairwise Sequence Alignment (Nucleotide). Available at http://www.ebi.ac.uk/Tools/psa/emboss_water/nucleotide.html. Accessed on Oct. 10, 2016.
Enari et al. A caspase-activated DNase that degrades DNA during apoptosis, and its inhibitor ICAD. Nature 391:43-50 (1998).
Florsheim, et al. Integrated Innate Mechanisms Involved in Airway Allergic Inflammation to the Serine Protease Subtilisin. J Immunol. May 15, 2015; 194(10): 4621-4630.
Foss et al. Effects of fixative and fixation time on the extraction and polymerase chain reaction amplification of RNA from paraffin-embedded tissue. Comparison of two housekeeping gene mRNA controls. Diagn Mol Path 3:148-155 (1994).
Freshney. Culture of Animal Cells: A Manual of Basic Technique and Specialized Applications. 6th Edition. 2010.
Giacona, et al. Cell-free DNA in human blood plasma: length measurements in patients with pancreatic cancer and healthy controls. Pancreas. Jul. 1998; 17(1):89-97.
Giaever, et al. Chemogenomic profiling: identifying the functional interactions of small molecules in yeast. Proc Natl Acad Sci U S A. Jan. 20, 2004;101(3):793-8. Epub Jan. 12, 2004.
Guatelli, et al. Isothermal, in vitro amplification of nucleic acids by a multienzyme reaction modeled after retroviral replication. PNAS USA 87(5):1874-1878 (1990).
Harkins, et al., Replicating fetal trisomy patient-like reference material for use in non-invasive prenatal screening tests. Sera Care. AMP 2015. Nov. 5-7, 2015.
Harlow, et al. Antibodies: A Laboratory manual. Cold Spring Harbor Laboratory. 1988.
Heinrich. et al. Kinase mutations and imatinib response in patients with metastatic gastrointestinal stromal tumor. Journal of Clinical Oncology.Dec. 1, 2003; 21(23):4342-4349.
Hindson, et al. High-throughput droplet digital PCR system for absolute quantitation of DNA copy number. Analytical Chemistry. 83(22):8604-8610 (2011).
Horizon Product Specification. cfDNA Reference Standard Set. 6068PSS-01(V-01). 2015.

(56) References Cited

OTHER PUBLICATIONS

Hussmann, et al. Reply to Schmitt et al.: Data-filtering schemes for avoiding double-counting in circle sequencing. PNAS. Apr. 22, 2014; 111(16).

Illumina. Genome Analyzer System. Available at http://support.illumina.com/content/dam/illumina-marketing/documents/products/datasheets/datasheet_genome_analyzeriix.pdf. Accessed onOct. 10, 2016.

International search report and written opinion dated Oct. 17, 2017 for PCT Application No. PCT/US2017/32980.

Jahr, et al. DNA fragments in the blood plasma of cancer patients: quantitations and evidence for their origin from apoptotic and necrotic cells. Cancer Res. Feb. 15, 2001;61(4):1659-65.

Jeffreys et al. DNA Enrichment by Allele-Specific Hybridization (DEASH): A Novel Method for Haplotyping and for Detecting Low-Frequency Base Substitutional Variants and Recombinant DNA Molecules. Genome Research 13:2316-2324 (2003).

Jiang et al. The Long and Short of Circulating Cell-Free DNA and the Ins and Outs of Molecular Diagnostics. Trends Genet 32(6):360-371 (2016).

Katayama, et al. Mechanisms of acquired crizotinib resistance in ALK-rearranged lung cancers. Sci. Transl Med. Feb. 8, 2012; 8(4).

Kent, W.J. Blat—The Blast-like alignment tool. Genome Research. 2012: 656-664.

Kumar, et al. Emerging technologies in yeast genomics. Nat Rev Genet. Apr. 2001;2(4):302-12.

Kurtz, et al. Versatile and open software for comparing large genomes. Biomed central. Jan. 30, 2004.

Landegren, U. Molecular mechanics of nucleic acid sequence amplification. Elsevier Science. Jun. 1993. 9(6). 199-204.

Langmead et al. Ultrafast and memory-efficient alignment of short DNA sequences to the human genome. Genome biology 10:R25 (10 pgs) (2009).

Larking, et al. Clustal W and Clustal X version 2.0. Bioinformatics applications note. 2007. 2947-2948; 23(21).

Lee, et al. Nucleic acid amplification technologies: application to disease diagnosis. Biotechniques books. 1997.

Li, et al. Fast and accurate long-read alignment with burrows-wheeler transform. Bioinformatics. Mar. 1, 2010;26(5):589-95.

Li et al. Fast and accurate short read alignment with burrows-wheeler transform. Bioinformatics 25(14):1754-1760 (2009).

Li, et al. Technical advance: Whole genome amplification of plasma-circulating DNA enables expanded screening for allelic imbalance in plasma. Journal of Molecular Diagnostics. Feb. 2006. 8(1); 22-30.

Lin, et al. Rolling Circle Enzymatic Replication of a Complex Multi-Crossover DNA Nanostructure. J Am Chem Soc. Nov. 21, 2007; 129(46): 14475-14481.

Lipman, et al. Rapid and sensitive protein similarity searches. Science. Mar. 22, 1985; 227(4693):1435-41.

Lizardi, et al. Exponential amplification of recombinant-RNA hybridization probes. Biotechnology. 1988. 6:1197-1202.

Lou, et al. High-throughput DNA sequencing errors are reduced by orders of magnitude using circle sequencing. Proc Natl Acad Sci U S A. Dec. 3, 2013;110(49):19872-7. doi: 10.1073/pnas.1319590110. Epub Nov. 15, 2013.

Lou et al., Supporting Information for "High-throughput DNA sequencing errors are reduced by orders of magnitude using circle sequencing," Proc Natl Acad Sci USA., 110(49):19872-7. doi: 10.1073/pnas.1319590110 (14 pages) (2013).

Maldonado, et al. Determinants of BRAF mutations in primary melanomas. Journal of the National Cancer Institute. Dec. 17, 2003; 95(24):1878-1890.

Matta, et al. Isolation and partial characterization of a thermostable extracellular protease of Bacillus polymyxa B-17. Int J Food Microbiol. Jul. 21, 1998;42(3):139-45 (abstract).

McLendon, et al. Survival analysis of presumptive prognostic markers among oligodendrogliomas. John Wiley & Sons. Oct. 15, 2005; 104(8):1693-1699.

McPherson, M. J. et al (Eds.) PCR 2: A Practical Approach. Practical approach series. IRL Press. 1995. (Table of Contents).

Miller, et al. A simple salting out procedure for extracting DNA from human nucleated cells. Nucleic Acid Research. 1988; 16(3).

Misale, et al. Emergence of KRAS mutations and acquired resistance to anti-EGFR therapy in colorectal cancer. Nature. Jun. 13, 2012; 486(7404):532-536.

Moran et al., Heat-labile proteases in molecular biology applications. FEMS Microbiology Letters 197(1): 59-63 (2001).

Neumann, et al., Frequency and type of KRAS mutations in routine diagnostic analysis of metastatic colorectal cancer. Pathol Res Pract. 2009;205(12):858-62.

Novocraft Technologies SDN BHD. NovoAlign. Available at http://www.novocraft.com/products/novoalign/. Accessed on Oct. 10, 2016.

Olivier, et al., TP53 mutations in human cancers: origins, consequences, and clinical use. Cold Spring Harb. Perspect Biology. 2010;1-17.

Pao, et al., EGF receptor gene mutations are common in lung cancers from "never smokers" and are associated with sensitivity of tumors to gefitinib and erlotinib. Proc. Natl. Acad. Sci. USA. Sep. 7, 2004; 101(36):13306-13311.

Paska et al. Effect of formalin, acetone, and RNAlater fixatives on tissue preservation and different size amplicons by real-time PCR from paraffin-embedded tissue. Diagn Mol Path 13(4): 234-240 (2004).

PCT/US2016/056126 International search Report and Written Opinion dated Jan. 11, 2017.

Pearson et al. Improved Tools for Biological Sequence Comparison. PNAS USA 85:2444-48 (1988).

Pinheiro et al., Evaluation of a Droplet Digital Polymerase Chain Reaction Format for DNA Copy Number Quantification. Analytical Chemistry. 84(2):1003-1011 (2012).

Polidoros, et al., Rolling circle amplification-RACE: A method for simultaneous isolation of 5' and 3' cDNA ends from amplified cDNA templates. BioTechniques 41.1 (Jul. 2006):35-42. including p. 1/1 of Supplementary Material.

Promega. Thermolysin—Thermostable Proteinase with High Digest Temperature; Better Denaturation, Digestion of Proteolytically Resistant Proteins. Available at https://www.promega.com/products/mass-spectrometry/proteases-and-surfactants/thermolysin/. Accessed Apr. 11, 2018.

Qiagen. How can QIAGEN Protease and Proteinase K be inactivated? Available at https://www.qiagen.com/ca/resources/faq?id=d24681d7-88e7-421a-84d9-27bfd5141103&lang=en. Accessed Apr. 11, 2018.

Remacle, et al. Substrate Cleavage Analysis of Furin and Related Proprotein Convertases—A Comparative Study. J Biol Chem. Jul. 25, 2008; 283(30): 20897-20906.

Samuels, et al. High Frequency of Mutations of the PIK3CA Gene in Human Cancers. Science Mag. Apr. 23, 2004; 304.

Schmitt et al., Detection of ultra-rare mutations by next-generation sequencing. PNAS. 109(36):14508-14523 (2012).

Schmitt, et al. Risks of double-counting in deep sequencing. PNAS. Apr. 22, 2014;111(16).

SeraCare and NIST Partner on Development of Circulating Tumor DNA Reference Standards for Diagnostics (Press Release). SeraCare Life Sciences, Inc. Jul. 14, 2016 (2 pages).

Seraseq(TM) ctDNA: A Breakthrough QC Technology. SeraCare Life Sciences, Inc. (2017) 6 pages.

Shaw, et al. Clinical Features and Outcome of Patients With Non-Small-Cell Lung Cancer Who Harbor EML4-ALK. Journal of Clinical Oncology. Sep. 10, 2009; 27(26):4247-4253.

Sievers, et al. Fast, Scalable generation of high-quality protein multiple sequence alignments using clustal omega. Molecular systems biology. 2011.

Sigma-Alorich. Protease from Streptomyces griseus. Available at https://www.sigmaaldrich.com/catalog/product/sigma/p6911?lang=en®ion=US#. Accessed Apr. 11, 2018.

Slater, et al. Automated generation of heuristics for biological sequence comparison. BMC Bioinformatics. Feb. 15, 2005; 6(31): 1-11.

SOAP.Short Oligonucleotide Analysis Package. Available at http://soap.genomics.org.cn/. Accessed on Oct. 10, 2016.

(56) References Cited

OTHER PUBLICATIONS

Sourceforge-Maq-Mapping-and-Assembly-with-Qualities. Available at http://maq.sourceforge.net/. Accessed on Oct. 10, 2016.
Spargo, et al. Detection of M. tuberculosis DNA using thermophilic strand displacement amplification. Mol Cell Probes. Aug. 1996;10(4):247-56.
Stanford. HIV Drug resistance database. Available at https://hivdb.stanford.edu/pages/genotype-rx.html. Accessed on Oct. 10, 2016.
Tissen, P. Laboratory techniques in biochemistry and molecular biology:Hybridization with nucleic acid probes. Elsevier Science. 1993.
U.S. Appl. No. 16/434,941 Non-Final Office Action dated Sep. 8, 2020.
U.S. Appl. No. 16/434,941 Final Office Action dated Mar. 10, 2020.
U.S. Appl. No. 16/434,941 Office Action dated Nov. 25, 2019.
U.S. Appl. No. 15/102,241 Office Action dated Apr. 25, 2019.
U.S. Appl. No. 15/102,241 Office Action dated Oct. 12, 2018.
U.S. Appl. No. 15/947,100 Office Action dated Oct. 24, 2019.
Walsh, et al. Chelex 100 as a medium for simple extraction of DNA for PCR-based typing from forensic material. BioTechniques. 1991; 10(4):506-513.
Wang, et al., Using ultra-sensitive next generation sequencing to dissect DNA damage-induced mutagenesis. Nature:Scientific Report. Dec. 2015.6:25310.
Wang et al., DNA amplification method tolerant to sample degradation. Genome Research. 14(11):2357-2366 (2004).
Wharam, et al. Specific detection of DNA and RNA targets using a novel isothermal nucleic acid amplification assay based on the formation of a three-way junction structure. Nucleic Acids Res. Jun. 1, 2001; 29(11): e54.
Widlak et al. Cleavage Preferences of the Apoptotic Endonuclease DFF40 (Caspase-activated DNase or Nuclease) on Naked DNA and Chromatin Substrates. The Journal of Biological Chemistry 275:8226-8232 (2000).
Winzeler, et al. Functional Characterization of the S. cerevisiae Genome by Gene Deletion and Parallel Analysis. Science. Aug. 6, 1999: vol. 285, Issue 5429, pp. 901-906.
Yan, et al. Isothermal amplified detection of DNA and RNA. Mol Biosyst. May 2014;10(5):970-1003.
EMBOSS. EMBOSS Needle: Pairwise Sequence Alignment (Nucleotide). Available at http://www.ebi.ac.uk/Tools/psa/emboss_needle/nucleotide.html. Accessed on Oct. 10, 2016.
Newman, et al. An ultrasensitive method for quantitating circulating tumor DNA with broad patient coverage. Nat Med. May 2014;20(5):548-54. Epub Apr. 6, 2014.
Beck, et al. Next generation sequencing of serum circulating nucleic acids from patients with invasive ductal breast cancer reveals differences to healthy and nonmalignant controls. Mol Cancer Res. Mar. 2010;8(3):335-42. doi: 10.1158/1541-7786.MCR-09-0314. Epub Mar. 9, 2010.
Dean et al., Comprehensive human genome amplification using multiple displacement amplification. Proc Natl Acad Sci USA 99(8): 5261-5266 (2002).
U.S. Appl. No. 16/301,707 Final Office Action dated Oct. 7, 2021.
U.S. Appl. No. 16/301,707 Non-Final Office Action dated May 19, 2021.
U.S. Appl. No. 16/434,941 Final Office Action dated Apr. 16, 2021.
U.S. Appl. No. 16/689,018 Non-Final Office Action dated Dec. 24, 2021.

* cited by examiner

| Mass ratio | RCA (one cycle) | RCA (multiple cycles) |
|---|---|---|
| 2 repeats:1 repeat | 3.59 | 33.46 |
| 3 repeats:1 repeat | 4.97 | 40.68 |

FIG. 6

| Spike-in fusion allele frequency | 2.50% | 0.50% | 0.05% | 0.00% |
|---|---|---|---|---|
| ng* of Fusion DNA (HD664ᵃ with 50% fusion allele) | 0.50 | 0.12 | 0.01 | 0.00 |
| ng* of Control DNA (wild type) | 9.50 | 9.88 | 9.99 | 10.00 |

*ng of circularized DNA a. HD664 refers to a 50% EML4/ALK DNA Reference Standard

FIG. 9

SEQUENCE LISTING

<160> NUMBER OF SEQ ID NOS: 86

<210> SEQ ID NO 1
<211> LENGTH: 29
<212> TYPE: DNA
<213> ORGANISM: Artificial Sequence
<220> FEATURE:

-continued

```
<223> OTHER INFORMATION: Description of Artificial Sequence: Synthetic
      oligonucleotide

<400> SEQUENCE: 1
ccatctaatt caacaagaat tgggacaac                                           29

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
acatgggtgg tggtatagcg cttgcg                                              26

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
caatttacat ctttatttat taacg                                               25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agctcgttta gtgaaccgtc agatc                                               25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gagtcacttt aaaatttgta tacac                                               25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
caaggctgtt agagagataa ttgga                                               25

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 7
gtgagtgatg gttgaggtag tgtggag                                    27

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
agctggacat cacctcccac aacg                                       24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ctctgaatac tttcaacaag ttac                                       24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aatatacctc tatactttaa cgtc                                       24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gatgaagccc tgaaagacgc gcag                                       24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gcatcaatgc agaagctgat ctca                                       24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gacggcatcg cagcttggat acac                                              24

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cttagcatgt ccgtggggtt tgaat                                             25

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gagcggataa caatttcaca cagg                                              24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cggtaggtat tgattgtaat tctg                                              24

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cccagtcacg acgttgtaaa acg                                               23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agcggataac aatttcacac agg                                               23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 19
cccttgaacc tcctcgttcg acc                                           23

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cagcggggct gctaaagcgc atgc                                          24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ctacaaactc ttcctgttag ttag                                          24

<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccttggcacc cgagaattcc atttgaggga tggcaccata t                       41

<210> SEQ ID NO 23
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gttcagagtt ctacagtccg acgatcggga caggataata ggagctaaca              50

<210> SEQ ID NO 24
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gttcagagtt ctacagtccg acgatccagt ttgaacagtt gtctggatc               49

<210> SEQ ID NO 25
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
```
ccttggcacc cgagaattcc aaaactgatg ggacccactc c    41

<210> SEQ ID NO 26
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gttcagagtt ctacagtccg acgatcttcc cactatcatt gattatttcc    50

<210> SEQ ID NO 27
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccttggcacc cgagaattcc atgggaaaat tattgcatat ctaagag    47

<210> SEQ ID NO 28
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gttcagagtt ctacagtccg acgatccttt ctcaccttct gggatcc    47

<210> SEQ ID NO 29
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccttggcacc cgagaattcc aaaattcccg tcgctatcaa g    41

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gttcagagtt ctacagtccg acgatcccat cacgtaggct tcctg    45

<210> SEQ ID NO 31
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
ccttggcacc cgagaattcc aatggccagc gtggacaac                                39
```

<210> SEQ ID NO 32
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
gttcagagtt ctacagtccg acgatcgaca tagtccagga ggcagc                        46
```

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

```
ccttggcacc cgagaattcc atgtccggga acacaaagac                               40
```

<210> SEQ ID NO 34
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

```
gttcagagtt ctacagtccg acgatcaagc gacggtcctc caag                          44
```

<210> SEQ ID NO 35
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35

```
ccttggcacc cgagaattcc atggcagcca ggaacgtac                                39
```

<210> SEQ ID NO 36
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36

```
gttcagagtt ctacagtccg acgatcagta cgttcctggc tgcc                          44
```

<210> SEQ ID NO 37
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

```
ccttggcacc cgagaattcc aaacaccgca gcatgtcaag                               40
```

```
<210> SEQ ID NO 38
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gttcagagtt ctacagtccg acgatcatcc acttgatagg caccttg                    47

<210> SEQ ID NO 39
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccttggcacc cgagaattcc aaagtggatg gcattggaat c                          41

<210> SEQ ID NO 40
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gttcagagtt ctacagtccg acgatctctc gctggcaggg attc                       44

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ccttggcacc cgagaattcc acctggagaa aggagaacgc                            40

<210> SEQ ID NO 42
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gttcagagtt ctacagtccg acgatcaact ttgggcgact atctgc                     46

<210> SEQ ID NO 43
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ccttggcacc cgagaattcc aagttccgtg agttgatcat cg                         42
```

<210> SEQ ID NO 44
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gttcagagtt ctacagtccg acgatcttgg agtctgtagg acttggc          47

<210> SEQ ID NO 45
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccttggcacc cgagaattcc aacttctacc gtgccctgat g                41

<210> SEQ ID NO 46
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gttcagagtt ctacagtccg acgatcctgc tgtgggatga ggtactc          47

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ccttggcacc cgagaattcc acacagcagg gcttcttcag                  40

<210> SEQ ID NO 48
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gttcagagtt ctacagtccg acgatccatg gaatgcttgt accacatc         48

<210> SEQ ID NO 49
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ccttggcacc cgagaattcc acatgggcaa cttctctgtt tc               42

```
<210> SEQ ID NO 50
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gttcagagtt ctacagtccg acgatcctgg cagccaggaa cgtact           46

<210> SEQ ID NO 51
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ccttggcacc cgagaattcc acgacggtcc tccaagtagt tc               42

<210> SEQ ID NO 52
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gttcagagtt ctacagtccg acgatcacac cgcagcatgt caagatc          47

<210> SEQ ID NO 53
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ccttggcacc cgagaattcc aagtacgttc ctggctgcca g                41

<210> SEQ ID NO 54
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gttcagagtt ctacagtccg acgatcgcac ggtgtataag gtaaggtcc        49

<210> SEQ ID NO 55
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ccttggcacc cgagaattcc agaattcagt ttccttcaag atcc             44

<210> SEQ ID NO 56
```

<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gttcagagtt ctacagtccg acgatcaaga gtgccttgac gatacagc                48

<210> SEQ ID NO 57
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ccttggcacc cgagaattcc atcttgccta cgccaccag                          39

<210> SEQ ID NO 58
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gttcagagtt ctacagtccg acgatctcga gaatatccaa gagacagg                48

<210> SEQ ID NO 59
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ccttggcacc cgagaattcc aagaggagta cagtgcaatg agg                     43

<210> SEQ ID NO 60
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gttcagagtt ctacagtccg acgatcgctt tgagctgttc tttgtcatt              49

<210> SEQ ID NO 61
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccttggcacc cgagaattcc aaaagcaatt tctacacgag atcc                   44

<210> SEQ ID NO 62
<211> LENGTH: 50

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gttcagagtt ctacagtccg acgatctttta attgtgtgga agatccaatc         50

<210> SEQ ID NO 63
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ccttggcacc cgagaattcc aattaaacag catgcattga actg                44

<210> SEQ ID NO 64
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gttcagagtt ctacagtccg acgatccctc tctctgaaat cactgagc              48

<210> SEQ ID NO 65
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ccttggcacc cgagaattcc agaggatctc gtgtagaaat tgc                 43

<210> SEQ ID NO 66
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gttcagagtt ctacagtccg acgatctgtt tctgctaacg atctctttg             49

<210> SEQ ID NO 67
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ccttggcacc cgagaattcc aaggagatat caagaggatg gattc               45

<210> SEQ ID NO 68
<211> LENGTH: 49
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 68
gttcagagtt ctacagtccg acgatccagg aaatcccata gcaataatg            49

<210> SEQ ID NO 69
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ccttggcacc cgagaattcc atcctgcaga aagacttgaa gg                   42

<210> SEQ ID NO 70
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gttcagagtt ctacagtccg acgatcgctt tgaatccaaa aaccttaaaa c         51

<210> SEQ ID NO 71
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ccttggcacc cgagaattcc aggattcaaa gcataaaaac cattac               46

<210> SEQ ID NO 72
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gttcagagtt ctacagtccg acgatcggat tcaaagcata aaaaccatta c         51

<210> SEQ ID NO 73
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ccttggcacc cgagaattcc agctttgaat ccaaaaacct taaaac               46

<210> SEQ ID NO 74
<211> LENGTH: 51
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 74
gttcagagtt ctacagtccg acgatcgatg ttagtgacaa tgaacctgat c         51

<210> SEQ ID NO 75
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ccttggcacc cgagaattcc atggtgttac agaagttgaa ctgc                 44

<210> SEQ ID NO 76
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gttcagagtt ctacagtccg acgatccctg actcagactg acattctcc            49

<210> SEQ ID NO 77
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ccttggcacc cgagaattcc acaggcccctt ctgtcttgaa c                   41

<210> SEQ ID NO 78
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gttcagagtt ctacagtccg acgatcatgt tccgagagct gaatgag              47

<210> SEQ ID NO 79
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ccttggcacc cgagaattcc agaacatctc gaagcgctca c                    41

<210> SEQ ID NO 80
<211> LENGTH: 48
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 80
gttcagagtt ctacagtccg acgatcttaa aggaccagac cagctttc                      48

<210> SEQ ID NO 81
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ccttggcacc cgagaattcc attatggtat aagttggtgt tctgaag                       47

<210> SEQ ID NO 82
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gttcagagtt ctacagtccg acgatcttat ggtataagtt ggtgttctga ag                 52

<210> SEQ ID NO 83
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ccttggcacc cgagaattcc attaaaggac cagaccagct ttc                           43

<210> SEQ ID NO 84
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gttcagagtt ctacagtccg acgatcgctc gacgctagga tctgac                        46

<210> SEQ ID NO 85
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ccttggcacc cgagaattcc actctgagtc aggaaacatt ttcag                         45

<210> SEQ ID NO 86
<211> LENGTH: 4

```
<212> TYPE: PRT
<213> ORGANISM: Homo sapiens

<400> SEQUENCE: 86

Asp Glu Ala Asp
1
```

METHODS AND COMPOSITIONS FOR ENRICHMENT OF AMPLIFICATION PRODUCTS

CROSS-REFERENCE

This application is a continuation of U.S. Ser. No. 15/947,100 filed on Apr. 6, 2018, which is a continuation of International Application No. PCT/US2016/056126 filed on Oct. 7, 2016, which claims the benefit of U.S. Provisional Application No. 62/239,690 filed on Oct. 9, 2015, which applications are incorporated herein by their reference.

SEQUENCE LISTING

The instant application contains a Sequence Listing which has been filed electronically in ASCII format and is hereby incorporated by reference in its entirety. Said ASCII copy, created on Jul. 13, 2020 is named 47608-702_303_SL.txt and is 19,825 bytes in size.

BACKGROUND OF THE INVENTION

The advent of large scale parallel nucleic acid sequencing has made the identification of sequence variation within complex populations feasible. Rolling circle amplification (RCA), an amplification process which utilizes a polymerase possessing strand displacement abilities, has emerged as a useful alternative and supplement to polymerase chain reaction (PCR) procedures for preparing nucleic acids for sequencing analysis. RCA involves growing a polynucleotide with a repetitive sequence by continuously adding nucleotides to a primer annealed to a circular polynucleotide template, such as a circular DNA template. This extension process can cover the entire length of the circular polynucleotide template multiple times, resulting in the formation of repeated sequences of the template or what can be referred to as concatemers. Concatemers can also serve as template to generate further amplification products. This extension, however, proceeds only until the terminus of the linear concatemer is reached. As the front of the growing polynucleotide strand encounters a double-stranded portion of DNA, the growing strand displaces the existing strand from the template. The result is often the formation of various lengths of double-stranded DNA consisting of a variable number of repeats of the template sequence. In the conventional methods of RCA, short concatemers are more often amplified disproportionally compared to longer concatemers that contain many repeats of a target sequence. Subsequent analyses of the longer concatemers may therefore be more difficult.

Large scale parallel sequencing has significant limitations in that the inherent error frequency in commonly-used techniques is larger than the frequency of many of the actual sequence variations in the population. For example, error rates of 0.1-1% have been reported in standard high throughput sequencing. Detection of rare sequence variants has high false positive rates when the frequency of variants is low, such as at or below the error rate.

The ability to detect rare sequence variants is pivotal for a variety of reasons. For example, detecting rare characteristic sequences can be used to identify and distinguish the presence of a harmful environmental contaminant, such as bacterial taxa. A common way of characterizing bacterial taxa is to identify differences in a highly conserved sequence, such as rRNA sequences. However, typical sequencing-based approaches to this date are faced with challenges relating to the sheer number of different genomes in a given sample and the degree of homology between members, presenting a complex problem for already laborious procedures.

The existing techniques for detecting sequence variations are particularly ineffective in detecting fusion gene variations and chromosome rearrangements. Often the 'partner' gene fused with the rearranged gene is not known, which makes the detection challenging. Fusions genes may also be difficult to detect if the junction site is not observed.

SUMMARY OF THE INVENTION

In view of the foregoing, there is a need for alternative and/or robust methods and compositions of detecting rare sequence variations, particularly rare sequence changes and gene fusion events. The compositions and methods of the present disclosure address this need, and provide additional advantages as well. In particular, the various aspects of the disclosure provide amplicons containing multiple copies of a target polynucleotide that can be used for massively parallel sequencing methods. Using amplicons containing multiple copies of a target polynucleotide, a target polynucleotide can be sequenced more than once, decreasing the error in sequencing rare sequence variants and fusion genes.

In one aspect, a method for enriching amplicons comprising a concatemer of at least two or more copies of a target polynucleotide is disclosed. The method comprises (a) generating a concatemer comprising a single-stranded polynucleotide from a circular target polynucleotide by extension of a first primer, the first primer comprising a first 3' end that specifically hybridizes to the target polynucleotide via sequence complementarity and a first 5' end comprising a first common sequence that does not specifically hybridize to the target polynucleotide via sequence complementarity, (b) generating a plurality of extension products containing one or more copies of the target polynucleotide by extension of a second primer comprising a second 3' end that specifically hybridizes to the concatemer via sequence complementarity and a second 5' end comprising a second common sequence that does not specifically hybridize to the concatemer via sequence complementarity, wherein the first common sequence and the second common sequence each comprise at least 10 contiguous nucleotides at a 5' end and are at least 90% identical when optimally aligned, and (c) amplifying the plurality of extension products of step (b) under conditions to generate a plurality of amplicons, wherein amplicons comprising at least 2 or more copies of the target polynucleotide are enriched. In some embodiments, step (a) is effected by a polymerase having strand-displacement activity. In some embodiments, the first common sequence and the second common sequence are identical. In some embodiments, the amplifying of step (c) comprises primer extension of a third primer, wherein the third primer comprises a sequence that specifically hybridizes to the first common sequence or the second common sequence via sequence complementarity. In some embodiments, the amplifying step of (c) yields a percentage of amplicons having two or more copies of the target polynucleotide that is greater than a percentage of amplicons having fewer than two copies of the target polynucleotide. In some embodiments, the percentage of amplicons having two or more copies of the target polynucleotide is at least 90%. In some embodiments, the percentage of amplicons having two or more copies of the target polynucleotide is at least 80%. In some embodiments, the percentage of amplicons having two or more copies of the target polynucleotide is at least 60%. In some embodiments, the extension products form stem loop structures comprising intramolecular hybridization between (i) the first common sequence and a complement of the second common sequence, or (ii) the second common sequence and a complement of the first common sequence. In some embodiments, the formation of the stem loop products is effected by performing the amplifying of step (c) with an annealing step held at a temperature within ±5° C. of a melting temperature of the third primer. In some embodiments, the formation of the stem loop products is effected by performing the amplifying of step (c) with an annealing step held at a temperature of less than 70° C. In some embodiments, the stem loop structures comprise intramolecular hybridization of at least 9 base pairs. In some embodiments, the stem loop structures comprise intramolecular hybridization of at least 15 base pairs. In some embodiments, the stem loop structures comprise intramolecular hybridization of at least 20 base pairs. In some embodiments, the stem loop structures comprise intramolecular hybridization of at least 25 base pairs. In some embodiments, the stem loop structures comprise intramolecular hybridization of at least 30 base pairs. In some embodiments, step (b) comprises no more than 6 cycles of extension of the second primer. In some embodiments, step (b) comprises no more than 8 cycles of extension of the second primer. In some embodiments, step (b) comprises no more than 10 cycles of extension of the second primer. In some embodiments, the first common sequence, the second common sequence, and the hybridizing sequence of the third primer all have melting temperatures (Tm's) within ±5° C. of one another. In some embodiments, the circular target polynucleotide is a circularized cell free DNA. In some embodiments, the circular target polynucleotide is a circularized fragment of genomic DNA. In some embodiments, the circular target polynucleotide comprises sequences resulting from a chromosomal rearrangement. In some embodiments, the chromosomal rearrangement is at least one of a deletion, duplication, inversion, and translocation. In some embodiments, the combined length of sequence portions of the target polynucleotide corresponding to, from 5' to 3' along the target polynucleotide, (i) sequence complementary to the first 3' end, (ii) sequence identical to the second 3' end, and (iii) intervening sequence between (i) and (ii), is 75 nucleotides or less. In some embodiments, at least 50% of concatemers comprise a target polynucleotide of at least 75 nucleotides in length. In some embodiments, the circular target polynucleotide is single-stranded. In some embodiments, the method further comprises sequencing the plurality of amplicons produced in step (c). In some embodiments, the sequencing is performed without selectively purifying amplicons comprising two or more copies of the target polynucleotide from amplicons comprising only one copy of the target polynucleotide. In some embodiments, the method further comprises purifying amplicons in the plurality of amplicons produced in step (c) that comprise two or more copies of the target polynucleotide. In some embodiments, the method further comprises sequencing the purified amplicons. In some embodiments, a plurality of different target polynucleotides is amplified in the same reaction mixture.

In another aspect, a reaction mixture for enriching amplicons comprising a concatemer of at least two or more copies of a target polynucleotide is disclosed. In one embodiment, the reaction mixture comprises (a) a circular target polynucleotide, (b) a first primer comprising a first 3' end that specifically hybridizes to the target polynucleotide via sequence complementarity and a first 5' end comprising a first common sequence that does not specifically hybridize to the target polynucleotide via sequence complementarity, and (c) a second primer comprising a second 3' end that specifically hybridizes to the concatemer via sequence complementarity and a second 5' end comprising a second common sequence that does not specifically hybridize to the concatemer via sequence complementarity, wherein the first common sequence and the second common sequence each comprise at least 10 contiguous nucleotides at a 5' end and are at least 90% identical when optimally aligned, and the concatemer is an extension product of the first primer. In some embodiments, the first common sequence and the second common sequence are identical. In some embodiments, the reaction mixture is contained in a container. In some embodiments, the container is a well, a plate, a tube, a chamber, a flow cell, or a chip. In some embodiments, the reaction mixture further comprises a third primer having a sequence that specifically hybridizes to the first common sequence or the second common sequence via sequence complementarity. In some embodiments, the first common sequence, the second common sequence, and the hybridizing sequence of the third primer all have melting temperatures (Tm's) within ±5° C. of one another. In some embodiments, the first common sequence and the second common sequence each comprise at least 15 nucleotides. In some embodiments, the circular target polynucleotide is a circularized cell free DNA. In some embodiments, the circular target polynucleotide is a circularized fragment of genomic DNA. In some embodiments, the circular target polynucleotide comprises sequences resulting from a chromosomal rearrangement. In some embodiments, the chromosomal rearrangement is at least one of a deletion, duplication, inversion, and translocation. In some embodiments, the combined length of sequence portions of the target polynucleotide corresponding to, from 5' to 3' along the target polynucleotide, (i) sequence complementary to the first 3' end, (ii) sequence identical to the second 3' end, and (iii) intervening sequence between (i) and (ii), is 75 nucleotides or less. In some embodiments, the circular target polynucleotide is single-stranded.

In another aspect, a kit for enriching amplicons comprising a concatemer of at least two or more copies of a target polynucleotide is disclosed. In one embodiment, the kit comprises (a) a first primer comprising a first 3' end that specifically hybridizes to the target polynucleotide via sequence complementarity and a first 5' end comprising a first common sequence that does not specifically hybridize to the target polynucleotide via sequence complementarity; (b) a second primer comprising a second 3' end that specifically hybridizes to the concatemer via sequence complementarity and a second 5' end comprising a second common sequence that does not specifically hybridize to the concatemer via sequence complementarity, wherein the first common sequence and the second common sequence each comprise at least 10 contiguous nucleotides at a 5' end and are at least 90% identical when optimally aligned, and the concatemer is an extension product of the first primer; and (c) a third primer having a sequence that specifically hybridizes to the first common sequence or the second common sequence via sequence complementarity. In some embodiments, the first common sequence and the second common sequence are identical. In some embodiments, the first common sequence, the second common sequence, and the hybridizing sequence of the third primer all have melting temperatures (Tm's) within ±5° C. of one another. In some embodiments, the combined length of sequence portions of the target polynucleotide corresponding to, from 5' to 3' along the target polynucleotide, (i) sequence complementary to the first 3' end, (ii) sequence identical to the second 3' end, and (iii) intervening sequence between (i) and (ii), is 75 nucleotides or less.

In another aspect, a system for designing primers for use in enriching amplicons comprising a concatemer of at least two or more copies of a target polynucleotide is disclosed. In one embodiment, the system comprises (a) a computer configured to receive a customer request to design primers for amplifying a specified target sequence; (b) computer readable medium comprising codes that, upon execution by one or more processors, design at least three primers for the amplification of the target sequence, wherein the at least three primers comprise: (i) a first primer comprising a first 3' end that specifically hybridizes to the target polynucleotide via sequence complementarity and a first 5' end comprising a first common sequence that does not specifically hybridize to the target polynucleotide via sequence complementarity; (ii) a second primer comprising a second 3' end that specifically hybridizes to the concatemer via sequence complementarity and a second 5' end comprising a second common sequence that does not specifically hybridize to the concatemer via sequence complementarity, wherein the first common sequence and the second common sequence each comprise at least 10 contiguous nucleotides at a 5' end and are at least 90% identical when optimally aligned, and the concatemer is an extension product of the first primer; and (iii) a third primer having a sequence that specifically hybridizes to the first common sequence or the second common sequence via sequence complementarity; and (c) a report generator that sends a report to a recipient, wherein the report contains sequences of the at least three primers. In some embodiments, the first common sequence and the second common sequence are identical. In some embodiments, the first common sequence, the second common sequence, and the hybridizing sequence of the third primer all have melting temperatures (Tm's) within ±5° C. of one another. In some embodiments, the combined length of sequence portions of the target polynucleotide corresponding to, from 5' to 3' along the target polynucleotide, (i) sequence complementary to the first 3' end, (ii) sequence identical to the second 3' end, and (iii) intervening sequence between (i) and (ii), is 75 nucleotides or less.

In an aspect, the present disclosure provides a method of conducting rolling circle amplification. The method comprises (a) providing a circular polynucleotide comprising a target polynucleotide; (b) subjecting an amplification reaction mixture to multiple cycles of rolling circle amplification to generate a plurality of amplification products comprising concatemers, wherein the amplification reaction mixture comprises (i) a polymerase having strand displacement activity, (ii) the circular polynucleotide, and (iii) primers; and wherein each cycle of the multiple cycles of rolling circle amplification comprises denaturation at a denaturing temperature, primer annealing at an annealing temperature, and primer elongation at an elongation temperature for a given elongation time period, to generate the plurality of amplification products; and wherein the plurality of amplification products generated is characterized in that it contains a higher proportion of concatemers having at least two copies of the target polynucleotide as compared to a plurality of amplification products generated by utilizing one cycle of amplification under comparable conditions for denaturation and primer annealing but with an elongation time period comparable to a sum of the elongation time period of the multiple cycles.

In an aspect, the present disclosure provides a method of increasing a proportion of concatemers having at least two copies of a target polynucleotide generated by a rolling circle amplification. The method comprises (a) providing a circular polynucleotide comprising a target polynucleotide; (b) subjecting an amplification reaction mixture to multiple cycles of rolling circle amplification to generate a plurality of amplification products comprising concatemers, wherein the amplification reaction mixture comprises (i) a polymerase having strand displacement activity, (ii) the circular polynucleotide, and (iii) primers; and wherein each cycle of the multiple cycles of rolling circle amplification comprises denaturation at a denaturing temperature, primer annealing at an annealing temperature, and primer elongation at an elongation temperature for a given elongation time period, to generate the plurality of amplification products; thereby increasing a proportion of concatemers having at least two copies of the target polynucleotide. In some embodiments, the proportion of concatemers in the plurality of amplification products having at least two copies of the target polynucleotide is increased as compared to a plurality of amplification products generated by utilizing one cycle of amplification under comparable conditions for denaturation and primer annealing but an elongation time period comparable to a sum of the elongation time period of the multiple cycles.

In some embodiments, the polymerase is selected from the group consisting of: Bsu DNA polymerase, Vent polymerase, Bst DNA polymerase, phi29 DNA polymerase, PyroPhage 3173 polymerase, any variant thereof, and any fragment thereof.

In some embodiments, the plurality of amplification products exhibits a mean fragment length of about 180 base pairs when the circular polynucleotide utilized in the reaction mixture comprises a human cell free DNA (cfDNA). In some embodiments, the plurality of amplification products exhibits a median fragment length of about 170 base pairs when the circular polynucleotide utilized in the reaction mixture comprises a human cell free DNA (cfDNA). In some embodiments, the plurality of amplification products exhibits a distribution of fragment lengths from about 40 bases to about 450 bases when the circular polynucleotide utilized in the reaction mixture comprises a human cell free DNA (cfDNA). In some embodiments, the plurality of amplification products exhibits a distribution of fragment lengths from about 100 bases to about 200 bases when the circular polynucleotide utilized in the reaction mixture comprises a human cell free DNA (cfDNA).

In some embodiments, the proportion of concatemers having at least two copies of the target polynucleotide is increased by at least about 1%. In some embodiments, the method further comprises supplementing the reaction mixture with the polymerase subsequent to at least one cycle of the multiple cycles of rolling circle amplification.

In some embodiments, the circular polynucleotide has a length of between about 40 bases and about 500 bases. In some embodiments, the circular polynucleotide comprises cell free DNA (cfDNA). In some embodiments, the circular polynucleotide comprises a fragment of genomic DNA. In some embodiments, the circular polynucleotide comprises a sequence resulting from a chromosomal rearrangement. In some embodiments, the chromosomal rearrangement is at least one of a deletion, duplication, inversion and translocation. In some embodiments, the circular polynucleotide is double stranded. In some embodiments, the circular polynucleotide is single stranded.

In some embodiments, a plurality of different circular polynucleotides is amplified in the amplification reaction mixture. In some embodiments, the multiple cycles comprises at least two cycles. In some embodiments, each cycle of the multiple cycles comprises denaturation at a denaturing temperature of between about 75° C. and about 95° C. for about 5 seconds to about 60 seconds, (ii) primer annealing at an annealing temperature of between about 45° C. and about 65° C. for about 5 seconds to about 60 seconds, and (iii) primer elongation at an elongation temperature of between about 65° C. and about 75° C. for an elongation time period of about 30 seconds to about 10 minutes. In some embodiments, each cycle of the multiple cycles comprises denaturation at a denaturing temperature of about 80° C. for about 15 seconds to about 30 seconds, (ii) primer annealing at an annealing temperature of about 50° C. for about 15 seconds to about 45 seconds, and (iii) primer elongation at an elongation temperature of about 70° C. for an elongation time period of about 3 minutes to about 10 minutes.

In some embodiments, the primers comprise random sequences capable of randomly hybridizing to and priming various regions of a circular polynucleotide for primer extension. In some embodiments, the primers comprise a gene specific sequence capable of hybridizing to and priming regions of a circular polynucleotide for primer extension in a sequence specific manner. In some embodiments, the primers comprise a first primer comprising (i) a first 3' end that specifically hybridizes to the circular polynucleotide via sequence complementarity and (ii) a first 5' end comprising a first common sequence that does not specifically hybridize to the target polynucleotide via sequence complementarity, wherein a concatemer comprising a single-stranded polynucleotide is generated during the multiple cycles of rolling circle amplification by extension of the first primer using the circular polynucleotide as template. In some embodiments, the primers comprise a second primer comprising (i) a second 3' end that specifically hybridizes to the concatemer comprising the single-stranded polynucleotide via sequence complementarity and (ii) a second 5' end comprising a second common sequence that does not specifically hybridize to the concatemer via sequence complementarity, wherein a plurality of extension products containing one or more copies of the target polynucleotide are generated during the multiple cycles of rolling circle amplification by extension of the second primer using the concatemer as template. In some embodiments, the first common sequence and the second common sequence each comprise at least 10 contiguous nucleotides at a 5' end and are at least 90% identical when optimally aligned. In some embodiments, the first common sequence and the second common sequence are identical.

In some embodiments, the method further comprises amplifying the plurality of extension products under conditions to generate a plurality of amplicons, wherein amplicons comprising at least 2 or more copies of the target polynucleotide are enriched. In some embodiments, amplifying comprises primer extension of a third primer, wherein the third primer comprises a sequence that specifically hybridizes to the first common sequence or the second common sequence via sequence complementarity. In some embodiments, amplifying yields a percentage of amplicons having two or more copies of the target polynucleotide that is greater than a percentage of amplicons having fewer than two copies of the target polynucleotide. In some embodiments, the percentage of amplicons having two or more copies of the target polynucleotide is at least 5%. In some embodiments, the percentage of amplicons having two or more copies of the target polynucleotide is at least 10%. In some embodiments, the percentage of amplicons having two or more copies of the target polynucleotide is at least 20%. In some embodiments, the percentage of amplicons having two or more copies of the target polynucleotide is at least 30%. In some embodiments, the percentage of amplicons having two or more copies of the target polynucleotide is at least 40%. In some embodiments, the percentage of amplicons having two or more copies of the target polynucleotide is at least 60%. In some embodiments, the percentage of amplicons having two or more copies of the target polynucleotide is at least 80%. In some embodiments, the percentage of amplicons having two or more copies of the target polynucleotide is at least 90%.

In some embodiments, the plurality of extension products form stem loop structures comprising intramolecular hybridization between (i) the first common sequence and a complement of the second common sequence, or (ii) the second common sequence and a complement of the first common sequence. In some embodiments, formation of the stem loop structures is effected by performing the amplifying with an annealing step held at a temperature within ±5° C. of a melting temperature of the third primer. In some embodiments, formation of the stem loop structures is effected by performing the amplifying with an annealing step held at a temperature of less than about 70° C. In some embodiments, the stem loop structures comprise intramolecular hybridization of at least 9 base pairs. In some embodiments, the stem loop structures comprise intramolecular hybridization of at least 15 base pairs. In some embodiments, the stem loop structures comprise intramolecular hybridization of at least 20 base pairs. In some embodiments, the stem loop structures comprise intramolecular hybridization of at least 25 base pairs. In some embodiments, the stem loop structures comprise intramolecular hybridization of at least 30 base pairs. In some embodiments, the first common sequence, the second common sequence, and the hybridizing sequence of the third primer all have melting temperatures (Tm's) within ±5° C. of one another.

In some embodiments, a combined length of sequence portions of a the target polynucleotide corresponding to, from 5' to 3' along the target polynucleotide, (i) sequence complementary to the first 3' end, (ii) sequence identical to the second 3' end, and (iii) intervening sequence between (i) and (ii), is 75 nucleotides or less.

In some embodiments, the method further comprises sequencing the plurality of amplification products comprising concatemers. In some embodiments, the sequencing is performed without selectively separating concatemers having at least two copies of the target polynucleotide from concatemers comprising less than two copies of the target polynucleotide.

In some embodiments, the method further comprises separating concatemers comprising at least two copies of the target polynucleotide from concatemers comprising less than two copies of the target polynucleotide. In some embodiments, the method further comprises sequencing the concatemers comprising at least two copies of the target polynucleotide.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (FIG. or Figure) of which:

FIG. 6 presents a table showing the ratio between amplification products with different numbers of repeats.

FIG. 9 presents a table illustrating mixing of HD664, an ELM4/ALK fusion DNA sample with a wild type reference DNA sample at different ratios, in accordance with an embodiment.

DETAILED DESCRIPTION OF THE INVENTION

Figure 1:
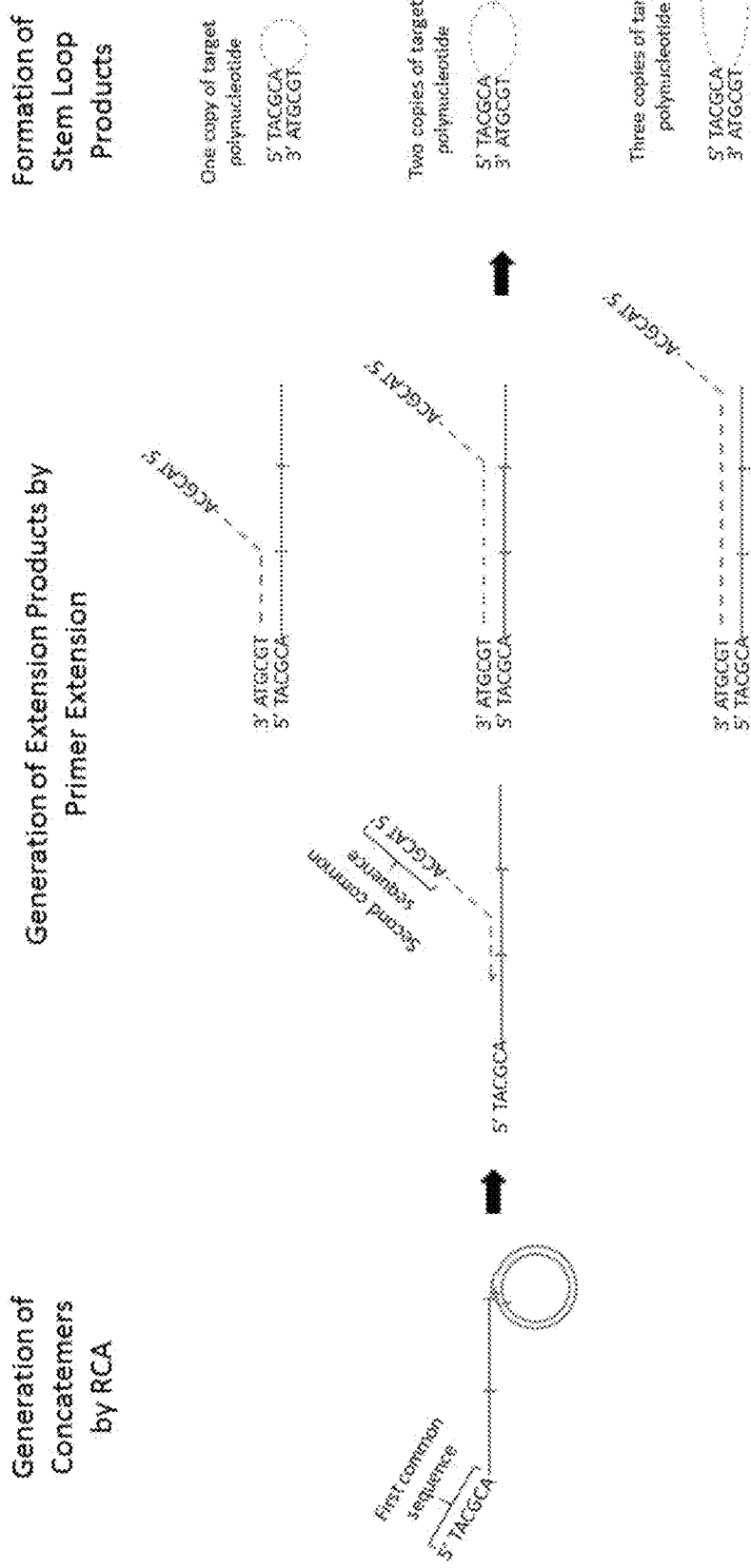
FIG. 1 illustrates the formation of stem loop products in accordance with an embodiment.

The practice of some methods disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "polynucleotide", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "target polynucleotide" refers to a nucleic acid molecule or polynucleotide in a starting population of nucleic acid molecules having a target sequence whose presence, amount, and/or nucleotide sequence, or changes in one or more of these, are desired to be determined. The target polynucleotide may be a portion of a larger polynucleotide (e.g. a portion to be amplified, sequenced, or otherwise analyzed), or may be used to refer to the larger polynucleotide comprising a target sequence. In general, the term "target sequence" refers to a nucleic acid sequence on a single strand of nucleic acid. The target sequence may be a portion of a gene, a regulatory sequence, genomic DNA, cDNA, fusion gene, RNA including mRNA, miRNA, rRNA, or others. The target sequence may be a target sequence from a sample or a secondary target such as a product of an amplification reaction.

In general, the term "sequence variant" refers to any variation in sequence relative to one or more reference sequences. Typically, the sequence variant occurs with a lower frequency than the reference sequence for a given population of individuals for whom the reference sequence is known. In some cases, the reference sequence is a single known reference sequence, such as the genomic sequence of a single individual. In some cases, the reference sequence is a consensus sequence formed by aligning multiple known sequences, such as the genomic sequence of multiple individuals serving as a reference population, or multiple sequencing reads of polynucleotides from the same individual. In some cases, the sequence variant occurs with a low frequency in the population (also referred to as a "rare" sequence variant). For example, the sequence variant may occur with a frequency of about or less than about 5%, 4%, 3%, 2%, 1.5%, 1%, 0.75%, 0.5%, 0.25%, 0.1%, 0.075%, 0.05%, 0.04%, 0.03%, 0.02%, 0.01%, 0.005%, 0.001%, or lower. In some cases, the sequence variant occurs with a frequency of about or less than about 0.1%. A sequence variant can be any variation with respect to a reference sequence. A sequence variation may consist of a change in, insertion of, or deletion of a single nucleotide, or of a plurality of nucleotides (e.g. 2, 3, 4, 5, 6, 7, 8, 9, 10, or more nucleotides). Where a sequence variant comprises two or more nucleotide differences, the nucleotides that are different may be contiguous with one another, or discontinuous. Non-limiting examples of types of sequence variants include single nucleotide polymorphisms (SNP), deletion/insertion polymorphisms (DIP), copy number variants (CNV), short tandem repeats (STR), simple sequence repeats (SSR), variable number of tandem repeats (VNTR), amplified fragment length polymorphisms (AFLP), retrotransposon-based insertion polymorphisms, sequence specific amplified polymorphism, and differences in epigenetic marks that can be detected as sequence variants (e.g. methylation differences). In some embodiments, a sequence variant can refer to a chromosome rearrangement, including but not limited to a translocation or fusion gene.

The term "concatemer," as used herein, generally refers to a ligation product or an amplification product comprising a continuous polynucleotide that contains multiple copies of a target polynucleotide sequence (e.g. at least 2, 3, 4, 5, 6, 7, 8, 9, or 10 copies of the target sequence; in some cases, at least 2 copies). In some cases, a concatemer contains multiple copies of a target polynucleotide sequence linked in tandem. In some cases, additional polynucleotide sequences are interspersed between the multiple copies of a target polynucleotide sequence.

The terms "hybridize," "hybridization," "hybridizing," "anneal," and "annealing," as used herein, generally refer to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of a PCR, or the enzymatic cleavage of a polynucleotide by a ribozyme. A first sequence that can be stabilized via hydrogen bonding with the bases of the nucleotide residues of a second sequence is said to be "hybridizable" to the second sequence. In such a case, the second sequence can also be said to be hybridizable to the first sequence.

The terms "complement," "complements," "complementary," and "complementarity," as used herein, generally refer to a sequence that is fully complementary to and hybridizable to the given sequence. In some cases, a sequence hybridized with a given nucleic acid is referred to as the "complement" or "reverse-complement" of the given molecule if its sequence of bases over a given region is capable of complementarily binding those of its binding partner, such that, for example, A-T, A-U, G-C, and G-U base pairs are formed. In general, a first sequence that is hybridizable to a second sequence is specifically or selectively hybridizable to the second sequence, such that hybridization to the second sequence or set of second sequences is preferred (e.g. thermodynamically more stable under a given set of conditions, such as stringent conditions commonly used in the art) to hybridization with non-target sequences during a hybridization reaction. Typically, hybridizable sequences share a degree of sequence complementarity over all or a portion of their respective lengths, such as between 25%-100% complementarity, including at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters.

The term "extension product," as used herein, generally refers to a product of a reaction in which a nucleotide primer is extending by the covalent addition of nucleotides. In some cases, the nucleotide incorporation can be guided by a template. In some cases, the nucleotide incorporation can occur without a template. In some cases, an extension product is an amplification product, such as from PCR amplification, rolling circle amplification (RCA), or isothermal amplification.

The terms "amplify," "amplifies," "amplified," "amplification," as used herein, generally refer to any process by which one or more copies are made of a target polynucleotide or a portion thereof. A variety of methods of amplifying polynucleotides (e.g. DNA and/or RNA) are available, some examples of which are described herein. Amplification may be linear, exponential, or involve both linear and exponential phases in a multi-phase amplification process. Amplification methods may involve changes in temperature, such as a heat denaturation step, or may be isothermal processes that do not require heat denaturation.

The terms "stem loop product" and "stem loop structure", as used herein, generally refer to a secondary structure of a polynucleotide in which intramolecular hybridization occurs between portions of the polynucleotide. A stem loop may form when two regions of a single polynucleotide strand hybridize to form a double-stranded portion, which can be referred to as a "stem," and a single-stranded loop that is unpaired, which can be referred to as a "loop". The stem can be of any variable length of base pairs, and base pairing along a stem may be interrupted internally by gaps of one or more unpaired bases on one or both portions participating in the stem. The loop can be of any variable length of unpaired bases. In some cases, the loop is at least 3 bases in length. In some cases, the two regions forming the "stem" are completely complementary. In some cases, the two regions forming the "stem" are partially complementary. In some cases, a single polynucleotide may comprise one stem loop structure. In some cases, a single polynucleotide may comprise more than one stem loop structure. The stem portion of a stem loop structure may terminate as a double stranded section with no overhangs, with a single stranded section comprising a 5' overhang, with a single stranded section comprising a 3' overhang, or with single-stranded portions extending from both the 5' end and the 3' end.

The present disclosure provides methods and compositions that can be used for generating amplicons comprising two or more copies of a target polynucleotide. In some embodiments, the methods are useful for detecting rare sequence variants and fusion genes. In some embodiments, gene fusions are detected without prior knowledge of a partner gene and can be applied for screening gene rearrangement events, such as in cell free DNA or genomic DNA samples. Various aspects of the disclosure provide amplicons containing two or more copies of a target polynucleotide that can be used with massively parallel sequencing methods.

In one aspect, the present disclosure provides a method of increasing a proportion of concatemers having at least two copies of a target polynucleotide generated by rolling circle amplification. The method comprises (a) providing a circular polynucleotide comprising a target polynucleotide, (b) subjecting an amplification reaction mixture to multiple cycles of rolling circle amplification to generate a plurality of amplification products comprising concatemers. The reaction mixture can comprise (i) a polymerase having strand displacement activity, (ii) the circular polynucleotide comprising the target polynucleotide, and (iii) primers. Each cycle of the multiple cycles of rolling circle amplification can comprise denaturation at a denaturing temperature, primer annealing at an annealing temperature, and primer elongation at an elongation temperature for a give elongation time period. The multiple cycles of rolling circle amplification can generate a plurality of amplification products having an increased proportion of concatemers having at least two copies of the target polynucleotide. The plurality of amplification products generated can be characterized in that it contains a higher proportion of concatemers having at least two copies of the target polynucleotide as compared to a plurality of amplification products generated by utilizing one cycle of amplification under comparable conditions for denaturation and primer annealing but with an elongation time period comparable to a sum of the elongation time period of the multiple cycles.

Rolling circle amplification can be facilitated by polymerases having strand displacement activity, for example DNA polymerases having strand displacement activity. A variety of polymerases useful in the subject methods are available, non-limiting examples of which include Bst DNA polymerase, large fragment; Bsu DNA polymerase, large fragment; Deep Vent$_R$™ DNA polymerase; Deep Vent$_R$™ (exo-) DNA polymerase; Klenow fragment (3'-5' exo-); DNA polymerase I, large fragment; M-MuLV reverse transcriptase; phi29 DNA polymerase; PyroPhage 3173 polymerase; Vent$_R$® DNA polymerase; and Vent$_R$® (exo-) DNA polymerase.

An amplification reaction mixture for conducting rolling circle amplification may comprise the necessary reagents for primer extension reactions, including, but not limited to a template (e.g., a circular polynucleotide), one or more primers, dNTPs, and buffer components. One cycle of amplification can comprise (i) denaturation at a denaturation temperature in which double-stranded template is converted to single-stranded polynucleotides, (ii) primer annealing at an annealing temperature in which primers hybridize to single-stranded polynucleotides, and (iii) primer elongation at an elongation temperature for a given elongation time period in which a primer hybridized to a single-stranded polynucleotide is extended using the single-stranded polynucleotide as template. Strand-displacing polymerases are particularly useful in RCA, as displacement allows the polymerase to continue around a circular template more than once, generating concatemeric tandem copies of sequences complementary to the circular template. Using a circular polynucleotide as template, primer extension can continue on the template, thereby generating an amplification product comprising multiple copies of the circular polynucleotide sequence (e.g., concatemer). In some embodiments, a plurality of amplification products are generated by subjecting the amplification reaction mixture to multiple cycles of rolling circle amplification.

In some embodiments, the multiple cycles comprise at least 2 cycles (e.g., at least 3, 4, 5, 6, 7, 8, 9, or 10 cycles). Multiple cycles of RCA can result in the formation of a plurality of linear concatemers from a circular template. During denaturation, extension of a first concatemer from a circular template is terminated. By repeating primer binding and extension, a plurality of concatemers can be generated from a circular template over multiple cycles. In some embodiments, three temperature phases are used—a first temperature phase for denaturation, a second temperature phase for primer binding, and a third temperature phase for primer extension. In some embodiments, a temperature for primer extension that is higher than for primer binding is selected to minimize primer binding during primer extension. Minimizing primer binding during primer extension can decrease the formation of shorter amplification products and reduce biased amplification of short fragments, as primers are less likely to hybridize to amplification products as they are being formed, such as in the case of a reverse primer included in the amplification reaction mixture. Primers hybridized to amplification products as they are being formed can also participate in primer extension but may result in preferential amplification of small fragments, as during extension, small circles tend to generate more copies of repeated units and more primer binding sites than large fragments within a given period of time. In some embodiments, a temperature selected for primer extension can be at least 5° C. (e.g. at least 6° C., 7° C., 8° C., 9° C., 10° C., 11° C., 12° C., 13° C., 14° C., 15° C. or greater) higher than a temperature selected for primer annealing. A temperature selected for primer extension can be about 1° C. to 20° C. higher (e.g. about 2° C. to 18° C., about 4° C. to 15° C., or about 5° C. to 10° C. higher) than a temperature selected for primer annealing. The range of temperatures suitable for non-isothermal RCA can depend on the properties of the polymerase enzyme used.

Each cycle of the multiple cycles can comprise denaturation at a denaturing temperature of at least about 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., or 95° C. Each cycle of the multiple cycles can comprise denaturation at a denaturing temperature of about 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., or 95° C. Each cycle of the multiple cycles can comprise denaturation at a denaturing temperature of at most about 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., or 95° C. Each cycle of the multiple cycles can comprise denaturation at a denaturing temperature of between about 70° C. and about 100° C., about 70° C. and about 95° C., about 70° C. and about 90° C., about 70° C. and about 85° C., about 70° C. and about 80° C., or about 70° C. and about 75° C. Each cycle of the multiple cycles can comprise denaturation at a denaturing temperature of between about 70° C. and about 100° C., about 75° C. and about 100° C., about 80° C. and about 100° C., about 85° C. and about 100° C., about 90° C. and about 100° C., or about 95° C. and about 100° C. Each cycle of the multiple cycles can comprise denaturation at a denaturing temperature for at least about 5 seconds, 10 seconds, 15 seconds, 20 seconds, 25 seconds, 30 seconds, 35 seconds, 40 seconds, 45 seconds, 50 seconds, 55 seconds, or 60 seconds. Each cycle of the multiple cycles can comprise denaturation at a denaturing temperature for about 5 seconds, 10 seconds, 15 seconds, 20 seconds, 25 seconds, 30 seconds, 35 seconds, 40 seconds, 45 seconds, 50 seconds, 55 seconds, or 60 seconds. Each cycle of the multiple cycles can comprise denaturation at a denaturing temperature for at most about 5 seconds, 10 seconds, 15 seconds, 20 seconds, 25 seconds, 30 seconds, 35 seconds, 40 seconds, 45 seconds, 50 seconds, 55 seconds, or 60 seconds. Each cycle of the multiple cycles can comprise denaturation at a denaturing temperature for between about 5 seconds and 60 seconds, 5 seconds and 55 seconds, 5 seconds and 50 seconds, 5 seconds and 45 seconds, 5 seconds and 40 seconds, 5 seconds and 35 seconds, 5 seconds and 30 seconds, 5 seconds and 25 seconds, 5 seconds and 20 seconds, 5 seconds and 15 seconds, or 5 seconds and 10 seconds. Each cycle of the multiple cycles can comprise denaturation at a denaturing temperature for between about 5 seconds and 60 seconds, 10 seconds and 60 seconds, 15 seconds and 60 seconds, 20 seconds and 60 seconds, 25 seconds and 60 seconds, 30 seconds and 60 seconds, 35 seconds and 60 seconds, 40 seconds and 60 seconds, 45 seconds and 60 seconds, 50 seconds and 60 seconds, or 55 seconds and 60 seconds.

Each cycle of the multiple cycles can comprise primer annealing at an annealing temperature of at least about 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., or 65° C. Each cycle of the multiple cycles can comprise primer annealing at an annealing temperature of about 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., or 65° C. Each cycle of the multiple cycles can comprise primer annealing at an annealing temperature of at most about 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., or 65° C. Each cycle of the multiple cycles can comprise primer annealing at an annealing temperature of between about 45° C. and about 65° C., about 45° C. and about 60° C., about 45° C. and about 55° C., or about 45° C. and about 50° C. Each cycle of the multiple cycles can comprise primer annealing at an annealing temperature of between about 45° C. and about 65° C., about 50° C. and about 65° C., about 55° C. and about 65° C., or about 60° C. and about 65° C. Each cycle of the multiple cycles can comprise primer annealing at an annealing temperature for at least about 5 seconds, 10 seconds, 15 seconds, 20 seconds, 25 seconds, 30 seconds, 35 seconds, 40 seconds, 45 seconds, 50 seconds, 55 seconds, or 60 seconds. Each cycle of the multiple cycles can comprise primer annealing at an annealing temperature for about 5 seconds, 10 seconds, 15 seconds, 20 seconds, 25 seconds, 30 seconds, 35 seconds, 40 seconds, 45 seconds, 50 seconds, 55 seconds, or 60 seconds. Each cycle of the multiple cycles can comprise primer annealing at an annealing temperature for at most about 5 seconds, 10 seconds, 15 seconds, 20 seconds, 25 seconds, 30 seconds, 35 seconds, 40 seconds, 45 seconds, 50 seconds, 55 seconds, or 60 seconds. Each cycle of the multiple cycles can comprise primer annealing at an annealing temperature for between about 5 seconds and 60 seconds, 5 seconds and 55 seconds, 5 seconds and 50 seconds, 5 seconds and 45 seconds, 5 seconds and 40 seconds, 5 seconds and 35 seconds, 5 seconds and 30 seconds, 5 seconds and 25 seconds, 5 seconds and 20 seconds, 5 seconds and 15 seconds, or 5 seconds and 10 seconds. Each cycle of the multiple cycles can comprise primer annealing at an annealing temperature for between about 5 seconds and 60 seconds, 10 seconds and 60 seconds, 15 seconds and 60 seconds, 20 seconds and 60 seconds, 25 seconds and 60 seconds, 30 seconds and 60 seconds, 35 seconds and 60 seconds, 40 seconds and 60 seconds, 45 seconds and 60 seconds, 50 seconds and 60 seconds, or 55 seconds and 60 seconds.

Each cycle of the multiple cycles can comprise primer elongation at an elongation temperature of at least about 65° C., 66° C., 67° C., 68° C., 69° C., 70° C., 71° C., 72° C., 73° C., 74° C., or 75° C. Each cycle of the multiple cycles can comprise primer elongation at an elongation temperature of about 65° C., 66° C., 67° C., 68° C., 69° C., 70° C., 71° C., 72° C., 73° C., 74° C., or 75° C. Each cycle of the multiple cycles can comprise primer elongation at an elongation temperature of at most about 65° C., 66° C., 67° C., 68° C., 69° C., 70° C., 71° C., 72° C., 73° C., 74° C., or 75° C. Each cycle of the multiple cycles can comprise primer elongation at an elongation temperature of between about 65° C. and about 75° C. or between about 65° C. and about 70° C. Each cycle of the multiple cycles can comprise primer elongation at an elongation temperature of between about 65° C. and about 75° C. or between about 70° C. and about 75° C. Each cycle of the multiple cycles can comprise primer elongation at an elongation temperature for an elongation time period of at least about 30 seconds, 1 minute, 2 minutes, 3 minutes, 4 minutes, 5 minutes, 6 minutes, 7 minutes, 8 minutes, 9 minutes, or 10 minutes. Each cycle of the multiple cycles can comprise primer elongation at an elongation temperature for an elongation time period of about 30 seconds, 1 minute, 2 minutes, 3 minutes, 4 minutes, 5 minutes, 6 minutes, 7 minutes, 8 minutes, 9 minutes, or 10 minutes. Each cycle of the multiple cycles can comprise primer elongation at an elongation temperature for an elongation time period of at most about 30 seconds, 1 minute, 2 minutes, 3 minutes, 4 minutes, 5 minutes, 6 minutes, 7 minutes, 8 minutes, 9 minutes, or 10 minutes. Each cycle of the multiple cycles can comprise primer elongation at an elongation temperature for an elongation time period of between about 30 seconds and 10 minutes, 30 seconds and 9 minutes, 30 seconds and 8 minutes, 30 seconds and 7 minutes, 30 seconds and 6 minutes, 30 seconds and 5 minutes, 30 seconds and 4 minutes, 30 seconds and 3 minutes, 30 seconds and 2 minutes, or 30 seconds and 1 minute. Each cycle of the multiple cycles can comprise primer elongation at an elongation temperature for an elongation time period of between about 30 seconds and 10 minutes, 1 minute and 10 minutes, 2 minutes and 10 minutes, 3 minutes and 10 minutes, 4 minute and 10 minutes, 5 minutes and 10 minutes, 6 minutes and 10 minutes, 7 minutes and 10 minutes, 8 minutes and 10 minutes, or 9 minutes and 10 minutes. The length of the elongation time period can be selected to optimize amplification product yield. Some factors for consideration when selecting an elongation time period include, but are not limited to, the size of the circular polynucleotide (e.g., circular template), GC content of the circular polynucleotide sequence, and the formation of secondary structure in the amplification product. For example, to produce a similar yield of amplification product, a longer circular polynucleotide may utilize longer elongation time periods as compared to a shorter circular polynucleotide. For further example, to produce a similar yield of amplification product, a circular polynucleotide having higher GC content may utilize longer elongation time periods as compared to a circular polynucleotide having lower GC content but comparable length.

In some embodiments, each cycle of the multiple cycles comprises denaturation at a denaturing temperature of between about between about 75° C. and about 95° C. for about 5 seconds to about 60 seconds, (ii) primer annealing at an annealing temperature of between about 45° C. and about 65° C. for about 5 seconds to about 60 seconds, and (iii) primer elongation at an elongation temperature of between about 65° C. and about 75° C. for an elongation time period of about 30 seconds to about 10 minutes. In some embodiments, each cycle of the multiple cycles comprises denaturation at a denaturing temperature of about 80° C. for about 15 seconds to about 30 seconds, (ii) primer annealing at an annealing temperature of about 50° C. for about 15 seconds to about 45 seconds, and (iii) primer elongation at an elongation temperature of about 70° C. for an elongation time period of about 3 minutes to about 10 minutes. In some embodiments, each cycle of the multiple cycles comprises denaturation at a denaturing temperature of about 80° C. for about 20 seconds, (ii) primer annealing at an annealing temperature of about 50° C. for about 30 seconds, and (iii) primer elongation at an elongation temperature of about 70° C. for an elongation time period of about 6 minutes.

In some embodiments, the reaction mixture is supplemented with polymerase at any cycle of the multiple cycles of rolling circle amplification. In some embodiments, the reaction mixture is supplemented with polymerase at at least two cycles of the multiple cycles of rolling circle amplification. Supplementing the amplification reaction mixture may be desired, in some cases, due to heat-inactivation of polymerase activity. Some polymerases are heat-inactivated at elevated temperatures. The temperature for heat-inactivation may depend on the polymerase used. Depending on the polymerase chosen for amplification and the temperature selected for any one of the denaturation temperature, the primer annealing temperature, and the primer extension temperature, polymerase may be optionally supplemented after at least one cycle of amplification. In some embodiments, the reaction mixture is supplemented with polymerase after every other cycle. In various embodiments, the reaction mixture is supplemented with polymerase as necessary, for example as determined by the yield of amplification product.

In some embodiments, the plurality of amplification products generated using methods disclosed herein are characterized in that they contain a higher proportion of concatemers having at least two copies (e.g., at least three, four, or five copies) of the target polynucleotide as compared to a plurality of amplification products generated utilizing one cycle of amplification under comparable conditions for denaturation and primer annealing but with an elongation time period comparable to a sum of the elongation time period of the multiple cycles.

Concatemers or amplification products having more copies of the target polynucleotide relative to amplification products have fewer copies of the target polynucleotide may have a larger fragment size. Determination of the number of copies of target polynucleotide in an amplification product or concatemer can be ascertained using a variety of methods, for example analysis by agarose gel, size exclusion chromatography, or next-generation sequencing. Concatemers or amplification products generated using methods comprising multiple cycles of rolling circle amplification as disclosed herein may, as ascertained using any suitable method (e.g., agarose gel, size exclusion chromatography, or next-generation sequencing), have an increased proportion of concatemers having at least two copies of the target polynucleotide as compared to rolling circle amplification comprising one cycle. The proportion of concatemers having at least two copies of the target polynucleotide, in some embodiments, is increased by at least 1%, 2%, 3%, 4%, 5%, 6%, 7%, 8%, 9%, 10%, 25%, or 50%.

In some embodiments, the plurality of amplification products exhibits a mean fragment length of at least about 100, 110, 120, 130, 140, 150, 160, 170, 180, 190, 200, 210, 220, 230, 240, or 250 base pairs. In some embodiments, the plurality of amplification products exhibits a mean fragment length of about 100, 110, 120, 130, 140, 150, 160, 170, 180, 190, 200, 210, 220, 230, 240, or 250 base pairs. In some embodiments, the plurality of amplification products exhibits a mean fragment length of at most about 100, 110, 120, 130, 140, 150, 160, 170, 180, 190, 200, 210, 220, 230, 240, or 250 base pairs. In some embodiments, the plurality of amplification products exhibits a mean fragment length of about 150 base pairs. In some embodiments, the plurality of amplification products exhibits a mean fragment length of about 160 base pairs. In some embodiments, the plurality of amplification products exhibits a mean fragment length of about 170 base pairs. In some embodiments, the plurality of amplification products exhibits a mean fragment length of about 180 base pairs. In some embodiments, the plurality of amplification products exhibits a mean fragment length of about 190 base pairs. In some embodiments, the plurality of amplification products exhibits a mean fragment length of about 200 base pairs.

In some embodiments, the plurality of amplification products exhibits a median fragment length of at least about 100, 110, 120, 130, 140, 150, 160, 170, 180, 190, 200, 210, 220, 230, 240, or 250 base pairs. In some embodiments, the plurality of amplification products exhibits a median fragment length of about 100, 110, 120, 130, 140, 150, 160, 170, 180, 190, 200, 210, 220, 230, 240, or 250 base pairs. In some embodiments, the plurality of amplification products exhibits a median fragment length of at most about 100, 110, 120, 130, 140, 150, 160, 170, 180, 190, 200, 210, 220, 230, 240, or 250 base pairs. In some embodiments, the plurality of amplification products exhibits a median fragment length of about 150 base pairs. In some embodiments, the plurality of amplification products exhibits a median fragment length of about 160 base pairs. In some embodiments, the plurality of amplification products exhibits a median fragment length of about 170 base pairs. In some embodiments, the plurality of amplification products exhibits a median fragment length of about 180 base pairs. In some embodiments, the plurality of amplification products exhibits a median fragment length of about 190 base pairs. In some embodiments, the plurality of amplification products exhibits a median fragment length of about 200 base pairs.

In some embodiments, analysis of cell free polynucleotides is desired, for example cell free DNA. Cell free DNA (cfDNA), as further described elsewhere herein, can be circulating tumor DNA or circulating fetal DNA. Cell free polynucleotides, in some cases, can comprise cell free RNA. Cell free DNA can be circularized, for example, by ligation using an enzyme such as ligase and amplified via the subject methods. In some embodiments, the plurality of amplification products exhibits a distribution of fragment lengths from about 40 bases to about 450 bases, 40 bases to about 400 bases, 40 bases to about 350 bases, 40 bases to about 300 bases, 40 bases to about 250 bases, 40 bases to about 200 bases, 40 bases to about 150 bases, 40 bases to about 100 bases, or 40 bases to about 50 bases when the circular polynucleotide utilized in the reaction mixture comprises a cfDNA. In some embodiments, the plurality of amplification products exhibits a distribution of fragment lengths from about 40 bases to about 450 bases, 50 bases to about 450 bases, 100 bases to about 450 bases, 150 bases to about 450 bases, 200 bases to about 450 bases, 250 bases to about 450 bases, 300 bases to about 450 bases, 350 bases to about 450 bases, or 400 bases to about 450 bases when the circular polynucleotide utilized in the reaction mixture comprises a cfDNA. In some embodiments, the plurality of amplification products exhibits a distribution of fragment lengths from about 100 bases to about 200 bases, 110 bases to about 200 bases, 120 bases to about 200 bases, 130 bases to about 200 bases, 140 bases to about 200 bases, 150 bases to about 200 bases, 160 bases to about 200 bases, 170 bases to about 200 bases, 180 bases to about 200 bases, or 190 bases to about 200 bases when the circular polynucleotide utilized in the reaction mixture comprises a cfDNA. In some embodiments, the plurality of amplification products exhibits a distribution of fragment lengths from about 100 bases to about 200 bases, 100 bases to about 190 bases, 100 bases to about 180 bases, 100 bases to about 170 bases, 100 bases to about 160 bases, 100 bases to about 150 bases, 100 bases to about 140 bases, 100 bases to about 130 bases, 100 bases to about 120 bases, or 100 bases to about 110 bases when the circular polynucleotide utilized in the reaction mixture comprises a cfDNA.

In some embodiments, primers in the amplification reaction mixture comprise random sequences. In some embodiments, primers in the amplification reaction mixture comprise gene specific sequences. In some embodiments, primers comprise gene specific sequences for multiple genes (e.g., at least 2, 3, 4, 5, 6, 7, 8, 9, or 10 genes). In some embodiments, the primers comprise a first primer comprising (i) a first 3' end that specifically hybridizes to the circular polynucleotide via sequence complementarity and (ii) a first 5' end comprising a first common sequence that does not specifically hybridize to the target polynucleotide via sequence complementarity. A concatemer comprising a single-stranded polynucleotide can be generated during the multiple cycles of rolling circle amplification by extension of the first primer using the circular polynucleotide as template. The primers may comprise a second primer comprising (i) a second 3' end that specifically hybridizes to the concatemer comprising the single-stranded polynucleotide via sequence complementarity and (ii) a second 5' end comprising a second common sequence that does not specifically hybridize to the concatemer via sequence complementarity. A plurality of extension products containing one or more copies of the target polynucleotide can be generated during the multiple cycles of rolling circle amplification by extension of the second primer using the concatemer as template. Methods of conducting amplification using such first primers and second primers, as further described herein, can be utilized to enrich amplicons comprising a concatemer of at least two or more copies of the target polynucleotide.

In one aspect, the present disclosure provides a method for enriching amplicons comprising a concatemer of at least two or more copies of a target polynucleotide. In one embodiment, the method comprises (a) generating a concatemer comprising a single-stranded polynucleotide from a circular target polynucleotide by extension of a first primer, the first primer comprising a first 3' end that specifically hybridizes to the target polynucleotide via sequence complementarity and a first 5' end comprising a first common sequence that does not specifically hybridize to the target polynucleotide via sequence complementarity, (b) generating a plurality of extension products containing one or more copies of the target polynucleotide by extension of a second primer comprising a second 3' end that specifically hybridizes to the concatemer via sequence complementarity and a second 5' end comprising a second common sequence that does not specifically hybridize to the concatemer via sequence complementarity, wherein the first common sequence and the second common sequence each comprise at least 10 contiguous nucleotides at a 5' end and are at least 90% identical when optimally aligned, and (c) amplifying the plurality of extension products of step (b) under conditions to generate a plurality of amplicons, wherein amplicons comprising at least 2 or more copies of the target polynucleotide are enriched.

In some embodiments, generating a concatemer comprising a single-stranded polynucleotide from a circular target polynucleotide comprises extension of a first primer. Primer extension can be accomplished by amplification reactions, including, but not limited to, thermocycling reactions and isothermal reactions. In some embodiments, thermocycling reactions involve several cycles of, for example, denaturation, primer binding, and primer extension. In some embodiments, generating concatemers of the subject methods is effected by a polymerase. A variety of polymerases useful in the subject methods are available, non-limiting examples of which are provided herein. In some embodiments, a polymerase for effecting the generation of concatemers has strand-displacement activity. In some embodiments, generating a concatemer comprising a single-stranded polynucleotide from a circular target polynucleotide comprises isothermal rolling circle amplification (RCA). Strand-displacing polymerases are particularly useful in RCA, as displacement allows the polymerase to continue around a circular template more than once, generating concatemeric tandem copies of sequences complementary to the circular template. In some embodiments, generating a concatemer comprising a single-stranded polynucleotide comprises non-isothermal RCA. Non-isothermal RCA can comprise at least two cycles (e.g. at least 2, 3, 4, 5, 6, 7, 8, 9, 10 or more cycles) of at least 2 temperature phases (e.g. at least 2, 3, 4, or more temperature phases). For example, a first temperature phase can be suitable for primer binding and extension, and a second temperature phase can be suitable for denaturing double-stranded polynucleotides. In some embodiments, non-isothermal RCA comprises between 2 and 35 cycles (e.g. between 3 and 30, between 4 and 20, between 5 and 15, or between 6 and 10 cycles) of at least two temperature phases. Cycling through temperature phases, including a second temperature phase suitable for denaturing double-stranded polynucleotides, during non-isothermal RCA can result in the formation of a plurality of linear concatemers from a circular template. During denaturation, extension of a first concatemer from a circular template is terminated. By repeating primer binding and extension, a plurality of concatemers can be generated from a circular template over several cycles. In some embodiments, three temperature phases are used—a first temperature phase for primer annealing, a second temperature phase for primer extension, and a third temperature phase for denaturing double-stranded polynucleotides. In some embodiments, a temperature for primer extension that is higher than for primer binding is selected to minimize primer binding during primer extension. Minimizing primer binding during primer extension can decrease the formation of shorter amplification products and reduce biased amplification of short fragments, as primers are less likely to hybridize to amplification products as they are being formed, such as in the case of a reverse primer included in the RCA reaction mixture. Primers hybridized to amplification products as they are being formed can also participate in primer extension but may result in preferential amplification of small fragments, as during extension, small circles tend to generate more copies of repeated units and more primer binding sites than large fragments within a given period of time. In some embodiments, a temperature selected for primer extension can be at least 5° C. (e.g. at least 6° C., 7° C., 8° C., 9° C., 10° C., 11° C., 12° C., 13° C., 14° C., 15° C. or greater) higher than a temperature selected for primer annealing. A temperature selected for primer extension can be about 1° C. to 20° C. higher (e.g. about 2° C. to 18° C., about 4° C. to 15° C., or about 5° C. to 10° C. higher) than a temperature selected for primer annealing. In some embodiments, non-isothermal RCA can comprise a fourth temperature phase. A fourth temperature phase can be, for example, suitable for forming secondary structure in an extension product, for example forming a stem loop structure. The range of temperatures suitable for non-isothermal RCA can depend on the properties of the polymerase enzyme used.

In some embodiments, RCA (isothermal or non-isothermal) can comprise a primer extension reaction along a linear template, such as extension of a reverse primer along a linear concatemer produced by primer extension along the circular template. For example, a second primer may hybridize to a template comprising a linear concatemeric template generated as an extension product of a first primer, and primer extension of the second primer during an primer extension phase can generate a linear, double-stranded polynucleotide, the strands of which can further serve as templates for extension by additional copies of the first and second primers.

In some embodiments, generating a plurality of extension products containing one or more copies of the target polynucleotide comprises extension of a second primer hybridized to a linear concatemeric template generated as an extension product of a first primer. In some embodiments, a plurality of extension products can be generated concurrently with the generation of linear concatemers from a circular template during non-isothermal RCA. Methods of primer extension and amplification often favor the amplification of short fragments compared to long fragments. In accordance with some embodiments, primer extension reactions to generate extension products can be optimized to reduce bias in favor of shorter products, and thus increase the proportion of longer products, such as products comprising two or more copies of the target polynucleotide. The present disclosure contemplates a variety of ways to accomplish this end, which may be used alone or in combination. One way to accomplish this is by limiting the number of primer extension cycles such that short fragments are not preferentially amplified, or amplified at a reduced frequency as compared to templates of the same length but lacking a hairpin structure. In some embodiments, generating extension products comprises extension of the second primer no more than 15 cycles (e.g. no more than 10, 8, 6, or fewer cycles). In some embodiments, generating the extension products comprises extension of the second primer between 2 and 15 cycles. In some embodiments, generating the extension products comprises extension of the second primer between 2 and 10 cycles. In some embodiments, extension of a second primer occurs concurrently with extension of a first primer.

In some embodiments, a circular target polynucleotide, herein used interchangeably with circular polynucleotide, which can be used for the generation of concatemers is formed from a linear target polynucleotide. In some embodiments, a circular target polynucleotide or a circular polynucleotide is single-stranded. In some embodiments, a circular target polynucleotide or a circular polynucleotide is double-stranded. A circular target polynucleotide or a circular polynucleotide can be of any length. In some embodiments, a circular target polynucleotide or a circular polynucleotide is about 25, 50, 75, 100, 150, 200, 250, 300, 400, 500, 600, 700, or 800 nucleotides in length. In some embodiments, a circular target polynucleotide or a circular polynucleotide is between 25-1000 nucleotides in length. In some embodiments, a circular target polynucleotide or a circular polynucleotide is between 50-500 nucleotides in length. In some embodiments, a circular target polynucleotide or a circular polynucleotide is between 75-250 nucleotides in length. In some embodiments, circular a target polynucleotide is or a circular polynucleotide between 100-200 nucleotides in length. A circular target polynucleotide or a circular polynucleotide can comprise a chromosome or gene fragment. In some embodiments, a circular target polynucleotide or a circular polynucleotide comprises a gene product, including but not limited to miRNA, rRNA, tRNA, and mRNA. In some embodiments, a circular target polynucleotide or a circular polynucleotide comprises sequences resulting from a point mutation, a SNP, insertion, or a deletion. In some embodiments, a circular target polynucleotide or a circular polynucleotide comprises sequences resulting from a chromosomal rearrangement. A chromosomal rearrangement can be one or more inversions; one or more deletions; one or more duplications; one or more translocations; or combinations thereof. In some embodiments, a circular target polynucleotide or a circular polynucleotide comprising one or more translocations comprises the fusion point, or fusion junction, of a fusion gene. In some embodiments, a circular target polynucleotide or a circular polynucleotide comprises at least one of an inversion, deletion, duplication, and translocation.

A first primer utilized in one or more subject methods to generate a concatemer can comprise a first 3' end that specifically hybridizes to the target polynucleotide via sequence complementarity and a first 5' end comprising a first common sequence that does not specifically hybridize to the target polynucleotide via sequence complementarity. A first primer can be any suitable length, such as at least 5, 10, 15, 20, 25, 30, 35, 40, 45, 50, 55, 60, 65, 70, 75, 80, 90, or 100 nucleotides, any portion of which may be complementary to the corresponding target sequence to which the primer hybridizes (e.g. at least 5, 10, 15, 20, 25, 30, 35, 40, 45, or 50 nucleotides). The first 3' end of the first primer that specifically hybridizes to the target polynucleotide via sequence complementarity can be any suitable length, such as at least 10, 15, 20, 25, 30, 35, 40, 45, 50, 55, 60, 65, 70, 75, 80, 85, 90, or 95 nucleotides in length. In some embodiments, a first primer comprises a first 3' end comprising a random nucleotide sequence that randomly hybridizes and primes various random regions of a circular target polynucleotide or a circular polynucleotide for primer extension, each random sequence specifically hybridizing to a corresponding complementary sequence via sequence complementarity. When the primer comprises a random 3'-end sequence, the target sequence is the sequence amplified by primer extension. Typically, a 3' end comprises the 3'-terminal nucleotide. The first 5' end (having a first common sequence of the first primer that does not specifically hybridize to the target polynucleotide via sequence complementarity) can be any suitable length, such as at least 10, 15, 20, 25, 30, 35, 40, 45, 50, 55, 60, 65, 70, 75, 80, 85, 90, or 95 nucleotides in length. The first common sequence can be any suitable length. In some embodiments, the first common sequence of the first primer is at least 10 (e.g. at least 15, 20, 25, 30, or more nucleotides in length). In general, a 5' end refers to a portion of a polynucleotide that is 5' with respect to the 3' end. In some embodiments, the 5' end comprises the 5' terminal nucleotide.

A second primer, comprising a second 3' end that specifically hybridizes to the concatemer via sequence complementarity and a second 5' end comprising a second common sequence that does not specifically hybridize to the concatemer via sequence complementarity, can be used for generating a plurality of extension products containing one or more copies of the target polynucleotide by primer extension. A second primer for generating a plurality of extension products can be of any suitable length, such as about or at least 5, 10, 15, 20, 25, 30, 35, 40, 45, 50, 55, 60, 65, 70, 75, 80, 90, or 100 nucleotides, any portion of which may be complementary to the corresponding target sequence to which the primer hybridizes (e.g. at least 5, 10, 15, 20, 25, 30, 35, 40, 45, 50 nucleotides). The second 3' end of the second primer that specifically hybridizes to the concatemer via sequence complementarity can be any suitable length, such as at least 10, 15, 20, 25, 30, 35, 40, 45, 50, 55, 60, 65, 70, 75, 80, 85, 90, or 95 nucleotides in length. In some embodiments, a second primer comprises a second 3' end comprising a random nucleotide sequence that randomly hybridizes and primes various random regions of a concatemer for primer extension. The second 5' end, comprising a second common sequence of the second primer that does not specifically hybridize to the concatemer via sequence complementarity, can be any suitable length, such as at least 10, 15, 20, 25, 30, 35, 40, 45, 50, 55, 60, 65, 70, 75, 80, 85, 90, or 95 nucleotides in length. The second common sequence can be any suitable length. In some embodiments, the second common sequence of the second primer is at least 10 nucleotides in length (e.g. at least 15, 20, 25, 30, or more nucleotides in length). In general, a 5' end refers to a portion of a polynucleotide that is 5' with respect to the 3' end. In some embodiments, the 5' end comprises the 5' terminal nucleotide. In some embodiments, the second common sequence is at least 80% identical (e.g. at least 90%, 95%, or 100% identical) to the first common sequence, such that the second common sequence is hybridizable to a complement of the first common sequence under suitable reaction conditions (e.g. one or more steps in an amplification reaction, such as primer hybridization and/or primer extension steps). In some embodiments, the first and second common sequences are identical.

In general, a common sequence that does not specifically hybridize to the target is designed to not hybridize to the target polynucleotide under conditions in which the 3' end does hybridize to the target polynucleotide (e.g. one or more steps in an amplification reaction). In some embodiments, the common sequence is designed to have less than 75%, 50%, 25%, 10%, or less complementarity with a sequence along the target polynucleotide that is 3' relative to where the 3' end hybridizes, with a sequence anywhere within the target polynucleotide, or with any of a group of polynucleotides in the sample (e.g. all genomic sequences of an organism, such as a bacteria, virus, plant, or animal, including human genomic DNA sequences). In certain embodiments, the first common sequence and the second common sequence each comprise at least 10 (e.g. at least 15, 20, 25, 30, 40, 50, or more) contiguous nucleotides at a 5' end and are at least 90% identical when optimally aligned. In certain embodiments, the first common sequence and the second common sequence comprise at least 5, 10, 15, 20, 25, or 30 contiguous nucleotides at a 5' end are at least 70% identical (e.g. at least 80%, 90%, 95%, or 100% identical) when optimally aligned.

In some embodiments, the extension products of the subject methods form stem loop structures comprising intramolecular hybridization between (i) the first common sequence and a complement of the second common sequence, and/or (ii) the second common sequence and a complement of the first common sequence. The extension products can form stem loop structures during non-isothermal RCA, for example during a fourth temperature phase with a temperature suitable for forming a stem loop structure. In some embodiments, the stem loop structures form during a subsequent amplification reaction, following RCA. The formation of a stem loop structure can depend on the stability of the double-stranded stem region and single-stranded loop region. The stability of the stem can depend on its length, the number of mismatches, and the base composition. The stability of a stem loop structure also depends on the length of the loop. Large loops without secondary structure can be unstable, and loops shorter than three bases long may not be sterically possible. In some embodiments, a stem loop structure with a longer stem portion can be more stable than a stem loop structure having the same loop and a shorter stem. In some circumstances, a stem loop structure with a longer loop can be less stable than a stem loop structure having the same stem and a shorter loop.

An illustrative embodiment of a method of generating a concatemer is shown in FIG. 1. A first primer comprising a first 3' end that specifically hybridizes to the target polynucleotide via sequence complementarity and a first 5' end comprising a first common sequence, 5'-TACGCA-3', that does not specifically hybridize to the target polynucleotide via sequence complementarity is extended by rolling circle amplification (RCA). Next, generating a plurality of extension products containing one or more copies of the target polynucleotide comprises extension of a second primer comprising a second 3' end that specifically hybridizes to the concatemer via sequence complementarity and a second 5' end comprising a second common sequence, 5'-TACGCA-3'(identical to the first common sequence), that does not specifically hybridize to the concatemer via sequence complementarity. Extension products can form stem loop structures as a result of intramolecular hybridization between the second common sequence and complement of the first common sequence. Stem loop structures can comprise a variable number of copies of the target polynucleotide. The length of the stem in base pairs can vary. In some embodiments, the stem is at least 6, 9, 15, 20, 25, 30, or more base pairs in length. In some embodiments, the stem loop structures comprise intramolecular hybridization of between 5 and 30 base pairs. In some embodiments, the stem loop structures comprise intramolecular hybridization of between 10 and 20 base pairs. Non-limiting examples of sequences that can be used as first or second common sequences are provided in Table 1.

TABLE 1

Non-limiting examples of candidate common sequences.

| Candidate Common Sequences | Sequences | SEQ ID NOS |
|---|---|---|
| Common_001 | CCATCTAATTCAACAAGAATTGGGACAAC | 1 |
| Common_002 | ACATGGGTGGTGGTATAGCGCTTGCG | 2 |
| Common_003 | CAATTTACATCTTTATTTATTAACG | 3 |
| Common_004 | AGCTCGTTTAGTGAACCGTCAGATC | 4 |
| Common_005 | GAGTCACTTTAAAATTTGTATACAC | 5 |
| Common_006 | CAAGGCTGTTAGAGAGATAATTGGA | 6 |
| Common_007 | GTGAGTGATGGTTGAGGTAGTGTGGAG | 7 |
| Common_008 | AGCTGGACATCACCTCCCACAACG | 8 |
| Common_009 | CTCTGAATACTTTCAACAAGTTAC | 9 |
| Common_010 | AATATACCTCTATACTTTAACGTC | 10 |
| Common_011 | GATGAAGCCCTGAAAGACGCGCAG | 11 |
| Common_012 | GCATCAATGCAGAAGCTGATCTCA | 12 |
| Common_013 | GACGGCATCGCAGCTTGGATACAC | 13 |
| Common_014 | CTTAGCATGTCCGTGGGGTTTGAAT | 14 |
| Common_015 | GAGCGGATAACAATTTCACACAGG | 15 |
| Common_016 | CGGTAGGTATTGATTGTAATTCTG | 16 |
| Common_017 | CCCAGTCACGACGTTGTAAAACG | 17 |
| Common_018 | AGCGGATAACAATTTCACACAGG | 18 |
| Common_019 | CCCTTGAACCTCCTCGTTCGACC | 19 |
| Common_020 | CCCTTGAACCTCCTCGTTCGACC | 19 |
| Common_021 | CAGCGGGGCTGCTAAAGCGCATGC | 20 |
| Common_022 | CTACAAACTCTTCCTGTTAGTTAG | 21 |

The number of base pairs involved in intramolecular hybridization can depend on the number of contiguous nucleotides of the first common sequence and the second common sequence, or the number of contiguous nucleotides of the second common sequence and complement of the first common sequence. The number of base pairs involved in intramolecular hybridization can also depend on the percentage identity of the first common sequence and the second common sequence, where percentage identity refers to percentage of identical bases between the first and second common sequence when the first and second common sequence are optimally aligned. In some embodiments, the first common sequence and the second common sequence each comprise at least 10 contiguous nucleotides at a 5' end and are at least 90% identical when optimally aligned. In some embodiments, the first common sequence and the second common sequence each comprise at least 5, 6, 7, 8, 9, 10, 11, 12, 13, 14, 15, 20, 25, 30, 35, 40, 45, or 50 contiguous nucleotides at a 5' end. In some embodiments, the first common sequence and the second common sequence each comprise between 5 and 25 contiguous nucleotides at a 5' end. In some embodiments, the first common sequence and the second common sequence are at least 60%, 65%, 70%, 75%, 80%, 85%, 90%, 95%, 96%, 97%, 98%, or 99% identical when optimally aligned. In some embodiments, the first common sequence and the second common sequence are between 60% and 100% identical when optimally aligned. In some embodiments, the first and second common sequence comprise between 5 and 25 contiguous nucleotides at a 5' end and are between 60% and 100% identical when optically aligned.

Amplifying the plurality of extension products of the first and second primers can comprise primer extension of a third primer. In some embodiments, the third primer comprises a sequence that specifically hybridizes to the first common sequence and/or the second common sequence via sequence complementarity. A third primer for nucleic acid amplification can be of any suitable length, such as at least 5, 6, 7, 8, 9, 10, 15, 20, 25, 30, 35, 40, 45, 50, 55, 60, 65, 70, 75, 80, 90, or 100 nucleotides, any portion or all of which may be complementary to the corresponding target sequence (e.g. about 5, 10, 15, 20, 25, 30, 35, 40, 45, 50 nucleotides or more). A third primer can comprise a segment comprising one or more amplification primer annealing sequences or complements thereof; one or more sequencing primer annealing sequences or complements thereof; one or more barcode sequences; one or more common sequences shared among multiple different primers; one or more restriction enzyme recognition sites; one or more probe binding sites or sequencing adapters (e.g., for attachment to a sequencing platform, such as a flow cell for massive parallel sequencing); one or more random or near-random sequences (e.g. one or more nucleotides selected at random from a set of two or more different nucleotides at one or more positions); and combinations thereof. An amplification primer annealing sequence may also serve as a sequencing primer annealing sequence.

Stem loop structures can be amplified with variable efficiencies depending on the stability of the stem loop structure. In general, among a plurality of stem loop structures comprising stems of the same length and loops of variable lengths, stem loop structures comprising longer loops are less thermodynamically stable, are more readily accessible as templates, and can be more efficiently amplified. Accordingly, in some embodiments, amplification of target sequences flanked by hybridizable common sequences enriches for amplicons comprising at least 2 or more copies of the target sequence. Amplicons resulting from primer extension of a third primer may comprise a variable number of copies of a target polynucleotide. In some embodiments, the percentage of amplicons having two or more copies of the target polynucleotide is at least 50% (e.g. at least 60%, 70%, 80%, 90%, or more). In some embodiments, the percentage of amplicons having two or more copies of the target polynucleotide is between 10% and 100% (e.g. between 20%-90%, 30%-80%, or 40%-60%).

In practicing the subject methods, the formation of stem loop products and enrichment of amplicons comprising at least 2 or more copies of the target polynucleotide can be optimized by one or more of specifying the melting temperatures of the first common sequence, the second common sequence, and the hybridizing sequence of the third primer sequence and adjusting the temperature at which amplification is conducted. For embodiments in which the amplification of primer extension products comprises primer extension of a third primer that specifically hybridizes to the first common sequence and/or the second common sequence, the efficiency of primer binding of the third primer can depend on one or more of the melting temperatures of the first common sequence, the second common sequence, and the hybridizing sequence of the third primer. In some embodiments, the first common sequence, the second common sequence, and the hybridizing sequence of the third primer all have melting temperatures (Tm's) within ±15° C. of one another (e.g. within ±10° C., ±5° C., or ±1° C.). In some embodiments, the first common sequence, the second common sequence, and the hybridizing sequence of the third primer all have melting temperatures (Tm's) within ±5° C. of one another. In general, a Tm generally represents the temperature at which 50% of an oligonucleotide consisting of a reference sequence (which may in fact be a subsequence within a larger polynucleotide) and its complementary sequence are hybridized (or separated). Tm may be based on a standard calculation, algorithm, or measurement, available in the art. An example tool for measuring Tm, OligoAnalyzer, is made available by Integrated DNA Technologies at www.idtdna.com/calc/analyzer, which may be set to use default parameters. Other similar tools are available.

The temperature at which amplification is conducted can also effect the efficiency of primer binding and extension for long stem loop products and short stem loop products. In certain embodiments, the formation of the stem loop structure can be effected by performing the amplifying step of (c) with an annealing step held at a temperature within ±15° C. of a melting temperature of the third primer (e.g. within ±10° C., ±5° C., or ±1° C.). In some embodiments, the formation of the stem loop products is effected by performing the amplifying step of (c) with an annealing step held at a temperature of less than 75° C. (e.g. less than 70° C., 65° C., 60° C., or lower). In some embodiments, the formation of the stem loop products is effected by performing the amplifying step of (c) with an annealing step held at a temperature between 55° C. and 75° C. (e.g. between 60° C. and 70° C.).

In some embodiments, the circular target polynucleotide or the circular polynucleotide is circularized cell free polynucleotide (e.g. cell free DNA, cDNA, or RNA). In some embodiments, the circular target polynucleotide or the circular polynucleotide is a circularized fragment of genomic DNA. In some embodiments, the circular target polynucleotide or a circular polynucleotide comprises sequences resulting from a chromosomal rearrangement. In certain embodiments, the chromosomal rearrangement is at least one of a deletion, duplication, inversion, and translocation. In some embodiments, circular target polynucleotides or circular polynucleotides of the subject methods are single-stranded. In some embodiments, circular target polynucleotides or circular polynucleotides of the subject methods are double-stranded. In certain embodiments, a combined length of sequence portions of the target polynucleotide corresponding to, from 5' to 3' along the target polynucleotide, (i) sequence complementary to the first 3' end, (ii) sequence identical to the second 3' end, and (iii) intervening sequence between (i) and (ii) is 75 nucleotides or less. In some embodiments, the combined length of sequence portions is 60 nucleotides or less. In some embodiments, the combined length of the sequence portions is 50 nucleotides or less. In some embodiments, the combined length of the sequence portions is 40 nucleotides or less. In some cases, the combined length of the sequence portions is 30 nucleotides or less.

Figure 2:
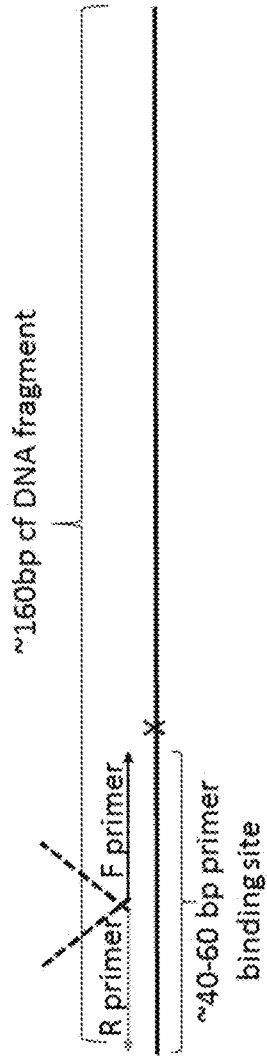
FIG. 2 illustrates back-to-back (B2B) primer designs, in which the forward and reverse primers are designed with neighboring 5' ends for RCA amplification, in accordance with an embodiment.
Figure 2:
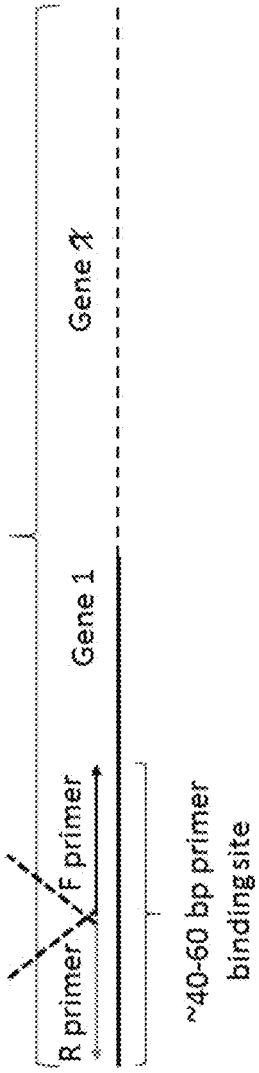

In one illustrative embodiment, a first primer and second primer are arranged as shown in FIG. 2. For simplicity, the relative hybridizing locations of the first and second primers are illustrated with respect to a single strand of the target polynucleotide. However, as noted below, one primer hybridizes to the strand comprising the target sequence, and the other hybridizes to the strand comprising a complement of the target sequence. A first 3' end of a first primer, forward primer (F primer), specifically hybridizes to the target polynucleotide via sequence complementarity and a first 5' end does not specifically hybridize to the target polynucleotide. A second 3' end of a second primer, reverse primer (R primer), specifically hybridizes to the complement of the target polynucleotide via sequence complementarity and a second 5' end does not specifically hybridize to the complement of the target polynucleotide. Given the orientation of the forward primer (F primer) and the reverse primer (R primer) with respect to a monomer of the target sequence, this arrangement may be referred to as a "back-to-back" (B2B) or "inverted" primers. Such a primer design has a reduced primer foot print (total distance spanned by a pair of primers) as compared to a traditional head-to-head design. In FIG. 2, a combined length of sequence portions of the target polynucleotide corresponding to, from a 5' to 3' end along the target polynucleotide, (i) sequence complementary to the first 3' end, (ii) sequence identical to the second 3' end, and intervening sequence between (i) and (ii) is about 30-100 nucleotides (e.g. 40-80, or 50-70 nucleotides). This combined length is also referred to as the "primer footprint." In some embodiments, the primer footprint is less than 100 nucleotides in length (e.g. less than 90, 80, 70, 60, 50, or fewer nucleotides in length). In some embodiments, a circularized target polynucleotide or a circular polynucleotide comprising a point mutation, indel (insertion/deletion), or gene fusion can be amplified using a first primer and second primer having a back-to-back arrangement. The reduced primer foot print of such a primer pair permits amplification of a wider variety of fragmentation events around a target sequence as a junction, for example a fusion junction, is less likely to occur between B2B primers than in the arrangement of primers found in a typical amplification reaction (facing one another, spanning a target sequence).

Figure 3:
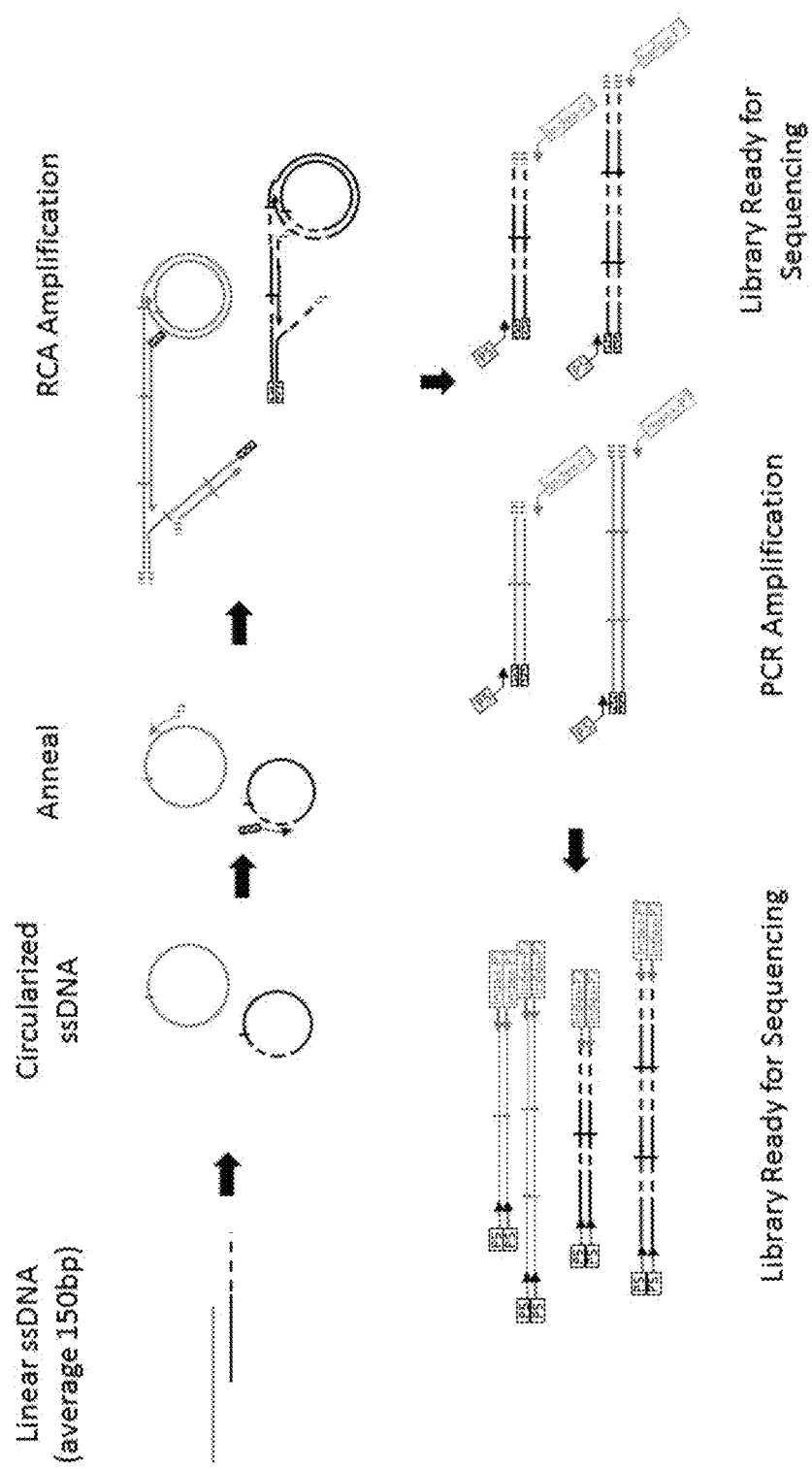
FIG. 3 illustrates a method for constructing a sequencing library using back-to-back primers, in accordance with an embodiment.

In one illustrative embodiment, a sequencing library is constructed as shown in FIG. 3. Linear DNA molecules are first circularized to form templates for RCA. Back-to-back primers with common sequencing adaptors at 5' ends bind the target molecules while a polymerase with strand-displacement activity amplifies the targets during RCA. The library can be sequenced or further amplified by PCR amplification before sequencing for the detection of sequence variants, for example point mutations, SNPs, and fusion genes.

In some embodiments, a plurality of concatemers can be generated from a plurality of target polynucleotides in a sample. The sample can contain one or more target sequences. Each target sequence may have one or more corresponding concatemers. Each concatemer corresponding to a unique target polynucleotide can contain a variable number of copies of a target polynucleotide. In some embodiments, the subject methods can be optimized to generate concatemers of variable lengths. Variability in concatemer length can result from variations in target polynucleotide lengths and/or number of copies of target polynucleotide per concatemer. In some embodiments, at least 50% (e.g. at least 60%, 70%, 80%, 90% or more) of concatemers comprise a target polynucleotide of at least 75 nucleotides in length (e.g. at least 100, 150, 200, or more nucleotides in length). In some embodiments, at least 80% of concatemers comprise a target polynucleotide of at least 75 nucleotides in length. In some embodiments, at least 60% of concatemers comprise a target polynucleotide of at least 100 nucleotides in length. In some embodiments, at least 50% of concatemers comprise a target polynucleotide of at least 150 nucleotides in length.

In some embodiments, a method of the present disclosure comprises sequencing the plurality of amplicons produced in step (c). In some embodiments, the sequencing is performed without selectively purifying amplicons comprising two or more copies of the target polynucleotide from amplicons comprising only one copy of the target polynucleotide. In some embodiments, a method of the present disclosure comprises purifying the amplicons in the plurality of amplicons produced in step (c) that comprise two or more copies of the target polynucleotide. In some embodiments, purified amplicons of the subject methods are sequenced. In certain embodiments, a method of the present disclosure comprises amplifying a plurality of different target polynucleotides in the same reaction mixture. The constituents of the plurality of target polynucleotides can be of variable lengths. In some embodiments, the target polynucleotides are between 30 nucleotides and 1000 nucleotides in length (e.g. 50-600, 75-500, 100-400, or 200-300 nucleotides in length). In some embodiments, the target polynucleotides are circularized by ligation in single reaction mixture.

Figure 4:
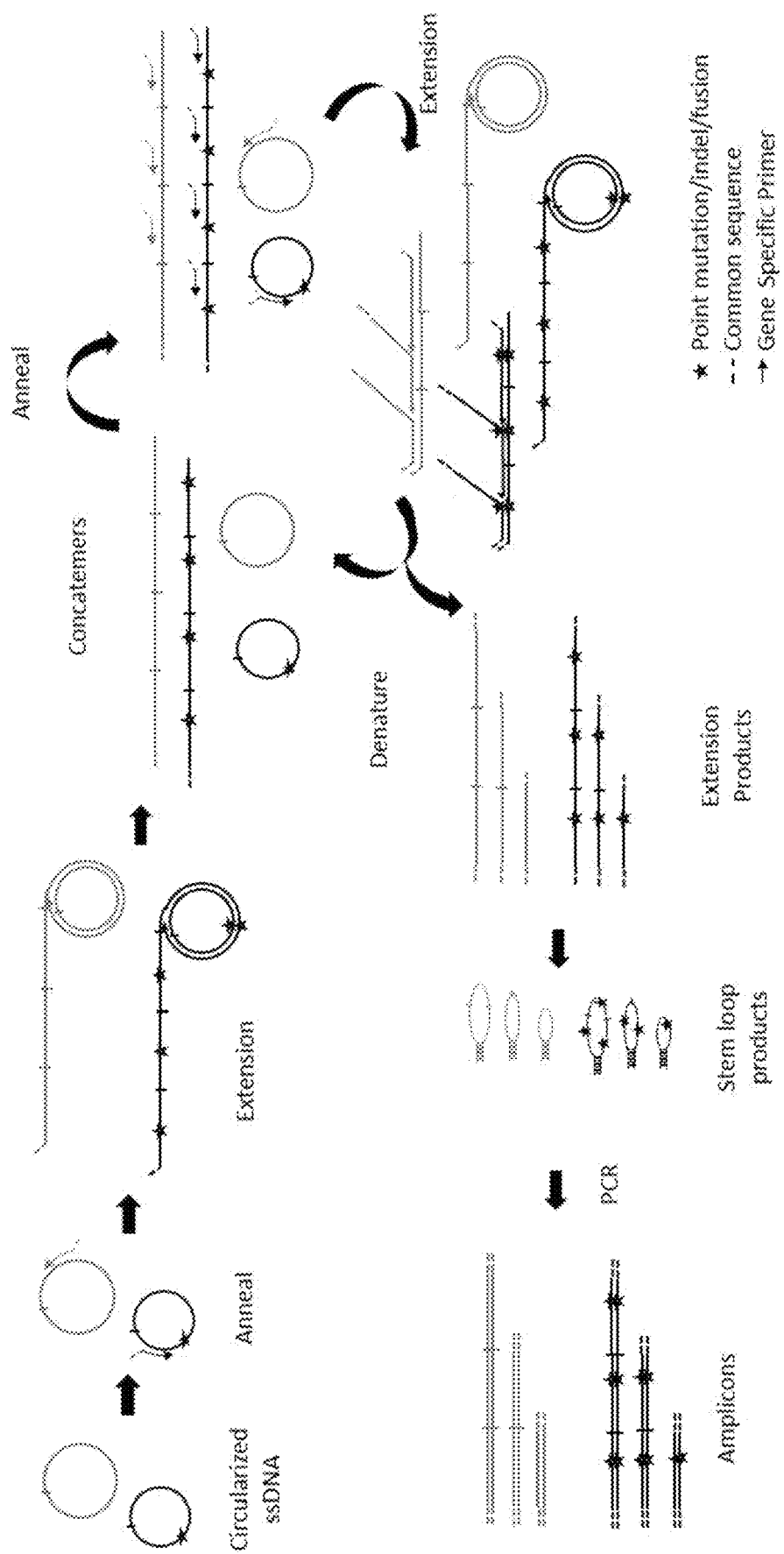
FIG. 4 illustrates a method for enriching amplicons in accordance with an embodiment.

In an illustrative embodiment, a nucleic acid sample containing a mixture of cell free polynucleotides is amplified as shown in FIG. 4. Polynucleotides in a mixture (e.g. single-stranded DNA, "ssDNA") can be circularized to form circular target polynucleotides or circular polynucleotides. Primer binding in a first temperature phase of non-isothermal RCA, such as 55° C., and primer extension of one or more first primers in a second temperature phase of non-isothermal RCA, such as 70° C., generates a mixture of concatemers. A temperature selected for primer extension that is higher than a temperature selected for primer binding can minimize additional primer binding during primer extension. Each target polynucleotide may have one or more corresponding concatemers. Each concatemer corresponding to a unique target polynucleotide can contain a variable number of copies of the target polynucleotide. According to the illustration, the one or more first primers comprise a first 3' end that specifically hybridize to the target polynucleotides via sequence complementarity and a first 5' end comprising a first common sequence that does not specifically hybridize to the target polynucleotides via sequence complementarity. In the following cycles of non-isothermal amplification, a plurality of second extension products are generated concurrently with the generation of concatemers, the extension products resulting from primer extension of one or more second primers in the second temperature phase, the one or more second primers having hybridized to a linear concatemeric template generated as an extension product of a first primer in a first temperature phase and not hybridized to the circular template due to denaturation during a third temperature phase, such as 94° C., in a previous cycle. New hybridization sites for the second primer are also exposed upon displacement by the progressing polymerase around the circular template. The one or more second primers comprise a second 3' end that specifically hybridize to the concatemers via sequence complementarity and a second 5' end comprising a second common sequence that does not specifically hybridize to the concatemers via sequence complementarity. Extension products can comprise various numbers of copies of a target polynucleotide. In a mixed sample, target polynucleotides can be of various lengths and the resulting extension products may also be of various lengths. Stem loop structures of various sizes can form as a result of intramolecular hybridization of the first common sequence and the complement of the second common sequence, or from intramolecular hybridization of the complement of the first common sequence and the sequence common sequence. Stem loop structures may form during one or more phases of amplification, such as annealing, extension, or a fourth temperature phase for stem-loop formation (e.g. 58° C.). Stem-loop structures may also form during a subsequent amplification reaction following RCA. Extension products can serve as the template for amplification reactions to generate amplicons, and the stability of the stem loop structures can affect primer binding and extension. During subsequent amplification reactions, extension products containing either longer target polynucleotide sequences or more copies can be preferentially enriched compared to extension products in which the stem loop structures have a smaller loop. In some embodiments, amplicons comprising two or more copies of target polynucleotide are enriched. In some embodiments, the percentage of amplicons having two or more copies of the target polynucleotide is at least 50% (e.g. at least 60%, 70%, 80%, 90%, or more). In some embodiments, the percentage of amplicons having two or more copies of the target polynucleotide is between 10% and 100% (e.g. between 20%-90%, 30%-80%, or 40%-60%). In some embodiments, amplicons comprising longer target polynucleotides are enriched. In some embodiments, at least 50% (e.g. at least 60%, 70%, 80%, 90% or more) of concatemers comprise a target polynucleotide of at least 75 nucleotides in length (e.g. at least 100, 150, 200, or more nucleotides in length). In some embodiments, at least 80% of concatemers comprise a target polynucleotide of at least 75 nucleotides in length. In some embodiments, at least 60% of concatemers comprise a target polynucleotide of at least 100 nucleotides in length. In some embodiments, at least 50% of concatemers comprise a target polynucleotide of at least 150 nucleotides in length.

In another aspect, the disclosure provides a reaction mixture for performing a method in accordance with methods of the disclosure. A reaction mixture can comprise one or more of the various components as described herein with respect to any of the various aspects and methods. In some embodiments, the disclosure provides a reaction mixture for enriching amplicons comprising a concatemer of at least two or more copies of a target polynucleotide. In one embodiment, the reaction mixture comprises (a) a circular target polynucleotide, (b) a first primer comprising a first 3' end that specifically hybridizes to the target polynucleotide via sequence complementarity and a first 5' end comprising a first common sequence that does not specifically hybridize to the target polynucleotide via sequence complementarity, and (c) a second primer comprising a second 3' end that specifically hybridizes to the concatemer via sequence complementarity and a second 5' end comprising a second common sequence that does not specifically hybridize to the concatemer via sequence complementarity, wherein the first common sequence and the second common sequence each comprise at least 10 contiguous nucleotides at a 5' end and are at least 90% identical when optimally aligned.

In some embodiments, a reaction mixture of the present disclosure is contained in a container. Each component may be packaged into different containers or where cross-reactivity and shelf-life permit, combinations of components can be provided in containers. A container can be a well, a plate, a tube, a chamber, a flow cell, or a chip.

In some embodiments, a reaction mixture comprises a third primer having a sequence that specifically hybridizes to the first common sequence or the second common sequence via sequence complementarity. In some embodiments, a third primer can be used to amplify a plurality of extension products. A third primer for nucleic acid amplification can be of any suitable length, such as at least 5, 6, 7, 8, 9, 10, 15, 20, 25, 30, 35, 40, 45, 50, 55, 60, 65, 70, 75, 80, 90, or 100 nucleotides, any portion or all of which may be complementary to the corresponding target sequence (e.g. about 5, 10, 15, 20, 25, 30, 35, 40, 45, 50 nucleotides or more). A third primer can comprise a segment comprising one or more amplification primer annealing sequences or complements thereof; one or more sequencing primer annealing sequences or complements thereof; one or more barcode sequences; one or more common sequences shared among multiple different primers; one or more restriction enzyme recognition sites; one or more probe binding sites or sequencing adapters (e.g., for attachment to a sequencing platform, such as a flow cell for massive parallel sequencing); one or more random or near-random sequences (e.g. one or more nucleotides selected at random from a set of two or more different nucleotides at one or more positions); and combinations thereof. An amplification primer annealing sequence may also serve as a sequencing primer annealing sequence.

In certain embodiments, extension products may form stem loop products and the amplicon yield from primer extension of a third primer can be optimized by optimizing properties of the first common sequence, the second common sequence, and the third hybridizing sequence of the third primer, for example by optimizing their melting temperatures. In some embodiments, the first common sequence, the second common sequence, and the hybridizing sequence of the third primer all have melting temperatures (Tm's) within ±15° C. of one another. In some embodiments, the first common sequence, the second common sequence, and the hybridizing sequence of the third primer all have melting temperatures (Tm's) within ±10° C. of one another. In some embodiments, the first common sequence, the second common sequence, and the hybridizing sequence of the third primer all have melting temperatures (Tm's) within ±5° C. of one another. In some embodiments, the first common sequence, the second common sequence, and the hybridizing sequence of the third primer all have melting temperatures (Tm's) within ±1° C. of one another.

In some embodiments, a reaction mixture of the present disclosure comprises a circularized cell free DNA as a circular target polynucleotide or a circular polynucleotide. In some embodiments, a reaction mixture of the present disclosure comprises a circularized fragment of genomic DNA as a circular target polynucleotide or a circular polynucleotide. In some embodiments, the circular target polynucleotide or the circular polynucleotide comprises sequences resulting from a chromosomal rearrangement. In certain embodiments, the chromosomal rearrangement is at least one of a deletion, duplication, inversion, and translocation. In some embodiments, circular target polynucleotides or circular polynucleotides of the subject methods are single-stranded. In some embodiments, circular target polynucleotides or circular polynucleotides of the subject methods are double-stranded.

In some embodiments, a reaction mixture of the present disclosure comprises a combined length of sequence portions of the target polynucleotide corresponding to, from 5' to 3' along the target polynucleotide, (i) sequence complementary to the first 3' end, (ii) sequence identical to the second 3' end, and (iii) intervening sequence between (i) and (ii) is 75 nucleotides or less. In some embodiments, the combined length of sequence portions of the target polynucleotide is 60 nucleotides or less. In some embodiments, the combined length of the sequence portions of the target polynucleotide is 50 nucleotides or less. In some embodiments, the combined length of the sequence portions of the target polynucleotide is 40 nucleotides or less. In some embodiments, the combined length of the sequence portions of the target polynucleotide is 30 nucleotides or less.

In some embodiments of the various aspects described herein, including the methods and reaction mixtures of the present disclosure, a circular target polynucleotide or a circular polynucleotide is formed from ligating a linear target polynucleotide. A circularized target polynucleotide formed from a linear target polynucleotide can comprise a sequence to be characterized, for example, a rare sequence variant or fusion gene. In some embodiments, a linear target polynucleotide is single-stranded. In other embodiments, a linear target polynucleotide is double-stranded. Non-limiting examples of target polynucleotide include DNA, RNA, cDNA, dsDNA, ssDNA, plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA (e.g., retroviral RNA).

In some embodiments of any of the various aspects, a circular target polynucleotide or a circular polynucleotide comprises a cell free polynucleotide, including but not limited to a cell free DNA or RNA (cfDNA or cfRNA). In some embodiments, a cell free polynucleotide is a circulating tumor DNA or RNA (ctDNA or ctRNA). In some embodiments, a cell free polynucleotide comprises fetal DNA or RNA. In some embodiments, cell free polynucleotides are polynucleotides originating from a cell but not directly obtained from a cellular source, such as a tissue sample. Non-limiting examples of sources from which cell free polynucleotides may originate are normal cells and tissue, abnormal cells and tissue (e.g., cancerous cells or tissue), fetal cells and tissue, and pathogens. A cell free polynucleotide present in a non-cellular source can result from cell death (e.g., apoptosis or necrosis) or cell shedding. Sequence analysis of cell free polynucleotides can be used to characterize the cell or population of cells from which the cell free DNA is derived, such as tumor cells (e.g. in cancer detection), fetal cells (e.g. in prenatal diagnostics), cells from transplanted tissue (e.g. in early detection of transplant failure), or a pathogen (e.g., bacteria or virus).

Any cell free polynucleotide can be used by embodiments of the present disclosure. Cell free polynucleotides can be obtained from a subject, such as any animal or living organism. Non-limiting examples of subjects are mammals, such as humans, non-human primates, rodents such as mice and rats, dogs, cats, pigs, sheep, rabbits and others. In some embodiments, a subject is healthy, and cell free polynucleotides obtained from the subject may not comprise a sequence variant associated with a disease or disorder. In some embodiments, a subject is suspected of having a disease or disorder, and cell free polynucleotides obtained from the subject may comprise a sequence variant associated with the disease or disorder. In some embodiments, a subject is pregnant, and cell free polynucleotides obtained from the subject comprises fetal polynucleotides.

Cell free polynucleotides can be obtained from various non-cellular sources. Non-limiting examples of non-cellular sources from which cell free polynucleotides can be obtained are serum, plasma, blood, perspiration, saliva, urine, stool, semen, mucosal excretions, spinal fluid, amniotic fluid, and lymph fluid. Various methods for collecting samples of non-cellular sources from which cell free polynucleotides can be obtained are available. In some embodiments, samples of non-cellular sources from which cell free polynucleotides can be obtained are obtained from a subject. In some embodiments, samples are obtained by venipuncture. In some embodiments, samples are obtained by aspiration.

Various methods and commercial kits are available for obtaining cell free polynucleotides, such as cell free DNA, from a sample. Examples of methods and kits for extracting and isolating cell free polynucleotides, including cell free DNA, are phenol/chloroform extraction, phenol/chloroform/isoamyl alcohol (PCI)-glycogen extraction, NaI (sodium iodide) extraction, guanidine-resin extraction, the QIAmp DNA Blood Midi kit with carrier RNA, the ChargeSwitch serum kit, the ZR serum DNA kit, Qiagen Qubit™ dsDNA HS Assay kit, Agilent™ DNA 1000 kit, TruSeq™ Sequencing Library Preparation, and the Puregene DNA purification system Blood Kit.

Cell free polynucleotides, including cell free DNA, can be extracted and isolated from bodily fluids through a partitioning step in which cell free polynucleotides are separated from cells and other non-soluble components of the bodily fluid. Examples of partitioning techniques are centrifugation and filtration. In some embodiments, cells are not partitioned from cell free polynucleotides first, but rather lysed. In some embodiments, the genomic DNA of intact cells is partitioned through selective precipitation. Cell free polynucleotides, including DNA, may remain soluble and may be separated from insoluble genomic DNA and extracted. According to some procedures, after addition of buffers and other wash steps specific to different kits, DNA may be precipitated using isopropanol precipitation. Further clean up steps may be used such as silica based columns to remove contaminants or salts. General steps may be optimized for specific applications. Non-specific bulk carrier polynucleotides, for example, may be added throughout the reaction to optimize certain aspects of the procedure such as yield.

In some embodiments of any of the various aspects disclosed herein, a circular target polynucleotide or a circular polynucleotide comprises genomic DNA. In some embodiments, a circular target polynucleotide or a circular polynucleotide is derived from genomic DNA. Genomic DNA can be obtained from a cell sample using various methods and commercial kits available, such as a Qiagen DNeasy Tissue Kit. Genomic DNA can be obtained and purified from a sample using any extraction, isolation, and purification method previously described elsewhere herein. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). For example, nucleic acids can be isolated and purified using solid phase reversible immobilisation (SPRI) beads (Agencourt AMPure XP). In some embodiments, the above isolation methods may be preceded by an enzyme digestion step to help eliminate unwanted protein from the sample, e.g., digestion with proteinase K, or other like proteases. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic acid isolation step, purification of nucleic acids can be performed after any step in the disclosed methods, such as to remove excess or unwanted reagents, reactants, or products. A variety of methods for determining the amount and/or purity of nucleic acids in a sample are available, such as by absorbance (e.g. absorbance of light at 260 nm, 280 nm, and a ratio of these) and detection of a label (e.g. fluorescent dyes and intercalating agents, such as SYBR green, SYBR blue, DAPI, propidium iodide, Hoechst stain, SYBR gold, ethidium bromide).

In some embodiments, a circular target polynucleotide or a circular polynucleotide comprises fragmented cell free DNA or fragmented genomic DNA. Various methods are available for fragmenting polynucleotides, including but not limited to chemical, enzymatic, and mechanical methods such as sonication, shearing, and contacting with restriction enzymes. In some embodiments, cell free DNA fragments are approximately uniform in length. In some embodiments, cell free DNA fragments are not approximately uniform in length. In some embodiments, cell free DNA fragments have an average length from about 50 to about 1000 nucleotides in length. In some embodiments, cell free DNA fragments have an average length from about 50 to about 500 nucleotides in length. In some embodiments, cell free DNA fragments have an average length from about 50 to about 250 nucleotides in length. In some embodiments, cell free DNA fragments have an average length from about 50 to about 200 nucleotides in length. In some embodiments, cell free DNA fragments have an average length from about 50 to about 100 nucleotides in length. In some embodiments, cell free DNA fragments have an average length from about 40 to about 1000 nucleotides in length. In some embodiments, cell free DNA fragments have an average length from about 40 to about 500 nucleotides in length. In some embodiments, cell free DNA fragments have an average length from about 40 to about 250 nucleotides in length. In some embodiments, cell free DNA fragments have an average length from about 40 to about 200 nucleotides in length. In some embodiments, cell free DNA fragments have an average length from about 40 to about 100 nucleotides in length. In some embodiments, genomic DNA is fragmented into polynucleotides of shorter lengths. In some embodiments, genomic DNA fragments are approximately uniform in length. In some embodiments, genomic DNA fragments are not approximately uniform in length. In some embodiments, genomic DNA fragments have an average length from about 50 to about 100 nucleotides in length. In some embodiments, genomic DNA fragments have an average length from about 50 and 250 nucleotides in length. In some embodiments, genomic DNA fragments have an average length from about 50 and 500 nucleotides in length. In some embodiments, genomic DNA fragments have an average length from about 50 and 750 nucleotides in length. In some embodiments, genomic DNA fragments have an average length from about 100 and 1000 nucleotides in length.

Circular target polynucleotides or circular polynucleotides may be formed from linear target polynucleotides by various methods. In some embodiments, a single linear target polynucleotide is circularized by end-joining. In some embodiments, a first linear target polynucleotide is joined to a second linear target polynucleotide, and then the unjoined end of the first target polynucleotide is joined to the unjoined end of the second linear target polynucleotide to form a circular target polynucleotide or a circular polynucleotide comprising the first and second target polynucleotides. Polynucleotides to be circularized may be single-stranded or double-stranded. Where single-stranded circles are desired, the polynucleotide may be a single-stranded polynucleotide as originally isolated, or may be treated to render the polynucleotide single-stranded (e.g. by denaturation). In some embodiments, a method for circularizing a polynucleotide involves an enzyme, such as use of a ligase (e.g., an RNA ligase or a DNA ligase). Non-limiting examples of enzymes that can be used to ligate a linear target polynucleotide into a circular target polynucleotide or a circular polynucleotide are ATP-dependent double-stranded polynucleotide ligases, NAD+ dependent DNA or RNA ligases, and single-strand polynucleotide ligases. Non-limiting examples of ligases are CircLigase I and CircLigase II (Epicentre; Madison, Wis.), *Escherichia coli* DNA ligase, *Thermus filiformis* DNA ligase, Tth DNA ligase, *Thermus scotoductus* DNA ligase (I and II), T3 DNA ligase, T4 DNA ligase, T4 RNA ligase, T7 DNA ligase, Taq ligase, Ampligase (Epicentre® Technologies Corp.), VanC-type ligase, 9° N DNA Ligase, Tsp DNA ligase, DNA ligase I, DNA ligase III, DNA ligase IV, Sso7-T3 DNA ligase, Sso7-T4 DNA ligase, Sso7-T7 DNA ligase, Sso7-Taq DNA ligase, Sso7-*E. coli* DNA ligase, Sso7-Ampligase DNA ligase, and thermostable ligases. Ligase enzymes may be wild-type, mutant isoforms, and genetically engineered variants. Ligation reactions may contain a buffer component, small molecule ligation enhancers, and other reaction components. In some embodiments, the concentration of polynucleotides and enzyme is adjusted to facilitate intermolecular ligation rather than intramolecular ligation. In some embodiments, the reaction temperature and reaction time, or length of the reaction, is adjusted. Reaction temperatures and times can be adjusted as well. In some embodiments, 60° C. is used to facilitate intramolecular circles. In some embodiments, reaction times are between 12-16 hours. Reaction conditions may be those specified by the manufacturer of the selected enzyme. In some embodiments, joining the ends of a polynucleotide to form a circular polynucleotide (either directly to itself or to one or more other polynucleotides, e.g., a circular target polynucleotide or a circular polynucleotide comprises two target polynucleotides) produces a junction having a junction sequence. In some embodiments, an exonuclease step can be included to digest any unligated nucleic acids after the circularization reaction. That is, closed circles do not contain a free 5' or 3' end, and thus the introduction of a 5' or 3' exonuclease will not digest the closed circles but will digest the unligated components. This may find particular use in multiplex systems.

After circularization, reaction products may be purified prior to amplification or sequencing to increase the relative concentration or purity of circularized polynucleotides available for participating in subsequent steps (e.g. by isolation of circular polynucleotides or removal of one or more other molecules in the reaction). For example, a circularization reaction or components thereof may be treated to remove single-stranded (non-circularized) polynucleotides, such as by treatment with an exonuclease. As a further example, a circularization reaction or portion thereof may be subjected to size exclusion chromatography, whereby small reagents are retained and discarded, or circularization products are retained and released in a separate volume. A variety of kits for cleaning up ligation reactions are available, such as kits provided by Zymo oligo purification kits made by Zymo Research. In some embodiments, purification comprises treatment to remove or degrade ligase used in the circularization reaction, and/or to purify circularized polynucleotides away from such ligase. In some embodiments, treatment to degrade ligase comprises treatment with a protease, such as proteinase K. Proteinase K treatment may follow manufacturer protocols, or standard protocols (e.g. as provided in Sambrook and Green, Molecular Cloning: A Laboratory Manual, 4th Edition (2012)). Protease treatment may also be followed by extraction and precipitation. In one example, circularized polynucleotides are purified by proteinase K (Qiagen) treatment in the presence of 0.1% SDS and 20 mM EDTA, extracted with 1:1 phenol/chloroform and chloroform, and precipitated with ethanol or isopropanol. In some embodiments, precipitation is in ethanol.

Some embodiments of the present disclosure comprise primer extension and amplification reactions, such as one or more of generating concatemers, generating a plurality of extension products, and amplifying a plurality of extension products. Primer extension reactions can involve changes in temperature (thermocycling) or a constant temperature (isothermal). In some embodiments, primer extension reactions comprise polymerase chain reaction (PCR). PCR involves cycling through multiple stages of denaturation, annealing of primer pairs to opposite strands, and primer extension to exponentially increase copy numbers of the target sequence, at least some of these stages generally occurring at different reaction temperatures. Non-limiting examples of PCR amplification techniques are quantitative PCR (qPCR or realtime PCR), reverse transcription PCR (RT-PCR), digital PCR (dPCR or dePCR), target-specific PCR, and quantitative reverse transcription PCR (qRT-PCR). Examples of polymerase enzymes that can be used for PCR are thermostable polymerases, including but not limited to, *Thermus thermophilus* HB8; mutant *Thermus oshimai; Thermus scotoductus; Thermus thermophilus* 1B21; *Thermus thermophilus* GK24; *Thermus aquaticus* polymerase (AmpliTaq® FS or Taq (G46D; F667Y), Taq (G46D; F667Y; E6811), and Taq (G46D; F667Y; T664N; R660G); *Pyrococcus furiosus* polymerase; *Thermococcus gorgonarius* polymerase; *Pyrococcus* species GB-D polymerase; *Thermococcus* sp. (strain 9° N-7) polymerase; *Bacillus stearothermophilus* polymerase; Tsp polymerase; ThermalAce™ polymerase (Invitrogen); *Thermus flavus* polymerase; *Thermus litoralis* polymerase; *Thermus* Z05 polymerase; delta Z05 polymerase (e.g. delta Z05 Gold DNA polymerase); and mutants, variants, or derivatives thereof. Additional examples of polymerase enzymes that can be used for PCR are non-thermostable polymerases, including, but are not limited to DNA polymerase I; mutant DNA polymerase I, including, but not limited to, Klenow fragment and Klenow fragment (3' to 5' exonuclease minus); T4 DNA polymerase; mutant T4 DNA polymerase; T7 DNA polymerase; mutant T7 DNA polymerase; phi29 DNA polymerase; and mutant phi29 DNA polymerase. In some embodiments, a hot start polymerase is used. A hot start polymerase is a modified form of a DNA Polymerase that requires thermal activation. Such a polymerase can be used, for example, to further increase sensitivity, specificity, and yield; and/or to further improve low copy target amplification. Typically, the hot start enzyme is provided in an inactive state. Upon thermal activation the modification or modifier is released, generating active enzyme. A number of hot start polymerases are available from various commercial sources, such as Applied Biosystems; Bio-Rad; eEnzyme LLC; Eppendorf North America; Finnzymes Oy; GeneChoice, Inc.; Invitrogen; Jena Bioscience GmbH; MIDSCI; Minerva Biolabs GmbH; New England Biolabs; Novagen; Promega; QIAGEN; Roche Applied Science; Sigma-Aldrich; Stratagene; Takara Mirus Bio; USB Corp.; Yorkshire Bioscience Ltd; and the like.

In some embodiments, primer extension and amplification reactions comprise isothermal reactions. Non-limiting examples of isothermal amplification technologies are ligase chain reaction (LCR) (e.g., U.S. Pat. Nos. 5,494,810 and 5,830,711); transcription mediated amplification (TMA) (e.g., U.S. Pat. Nos. 5,399,491, 5,888,779, 5,705,365, 5,710,029); nucleic acid sequence-based amplification (NASBA) (e.g., Malek et al., U.S. Pat. No. 5,130,238); signal mediated amplification of RNA technology (SMART) (e.g., Wharam et al., *Nucleic Acids Res.* 2001, 29, e54); strand displacement amplification (SDA) (e.g., U.S. Pat. No. 5,455,166); thermophilic SDA (Spargo et al., *Mol Cell Probes* 1996, 10:247-256; European Pat. No. 0684315); rolling circle amplification (RCA) (e.g., Lizardi, "Rolling Circle Replication Reporter Systems," U.S. Pat. No. 5,854,033); loop-mediated isothermal amplification of DNA (LAMP) (e.g., Notomi et al., "Process for Synthesizing Nucleic Acid," U.S. Pat. No. 6,410,278); helicase-dependent amplification (HDA) (e.g., U.S. Pat. Appl. US 20040058378); single primer isothermal amplification (SPIA) (e.g., WO2001020035 and U.S. Pat. No. 6,251,639); and circular helicase-dependent amplification (cHDA) (e.g., U.S. patent application U.S. Ser. No. 10/594,095).

In some embodiments, primer extension reactions are effected by polymerases having strand-displacement activity, such as for RCA. In some embodiments, isothermal amplification comprises rolling circle amplification (RCA). A RCA reaction mixture can comprise one or more primers, a polymerase having strand displacement activity, and dNTPs. Strand displacement refers to the ability to displace down-stream DNA during synthesis. Polymerases having strand-displacement activity may have varying degrees of strand displacement activity. In some embodiments, a polymerase may have weak or no strand-displacement activity. In some embodiments, polymerases may have strong strand displacement activity. In some embodiments, polymerases with strand displacement activity may have different levels of strand-displacement activity at different reaction temperatures. In some embodiments, a polymerase may display strand displacement activity at moderate temperatures, e.g., 20° C.-37° C. In some embodiments, a polymerase may display strand displacement activity at elevated temperatures, e.g., 65° C. Reaction temperatures can be adjusted to favor a level of activity of a polymerase having strand-displacement activity. In some embodiments, a reaction temperature is at least 20° C., 25° C., 30° C., 35° C., 40° C., 45° C., 50° C., 55° C., 60° C., 65° C., 70° C., 75° C., 80° C., 85° C., or 90° C. In some embodiments, a reaction temperature is between 20° C. and 80° C. In some embodiments, a reaction temperature is between 20° C. and 70° C. In some embodiments, a reaction temperature is between 20° C. and 60° C. In some embodiments, a reaction temperature is between 20° C. and 50° C. In some embodiments, various reaction temperatures can be cycled through in different stages to increase or decrease the strand displacement activity of a polymerase Non-limiting examples of polymerases having strand displacement activity are Bst DNA polymerase, large fragment; Bsu DNA polymerase, large fragment; Deep Vent$_R$™ DNA polymerase; Deep Vent$_R$™ (exo-) DNA polymerase; Klenow fragment (3'-5' exo-); DNA polymerase I, large fragment; M-MuLV reverse transcriptase; phi29 DNA polymerase; PyroPhage 3173 polymerase; Vent$_R$® DNA polymerase; and Vent$_R$® (exo-) DNA polymerase.

Concatemers generated as products of amplification reactions, including thermocycling methods, isothermal methods, and combinations of these, can comprise two or more copies of a target polynucleotide. A concatemer may comprise about 2, 3, 4, 5, 6, 7, 8, 9, 10 or more copies of the target polynucleotide. In some embodiments, concatemers are generated as products of primer extension reactions from a plurality of target polynucleotides, wherein constituents of the plurality are non-uniform in length and comprise a plurality of sequences.

In some embodiments of any of the various aspects of the disclosure, a primer may comprise one or more portions. For example, a primer may comprise one or more amplification primer annealing sequences or complements thereof; one or more sequencing primer annealing sequences or complements thereof; one or more barcode sequences; one or more common sequences shared among multiple different primers; one or more restriction enzyme recognition sites; one or more probe binding sites or sequencing adapters (e.g., for attachment to a sequencing platform, such as a flow cell for massive parallel sequencing); one or more random or near-random sequences (e.g. one or more nucleotides selected at random from a set of two or more different nucleotides at one or more positions, with each of the different nucleotides selected at one or more positions represented in a pool of primers comprising the random sequence); and combinations thereof. In some embodiments, a primer such as a third primer comprises a sequencing adapter element (herein also referred to as adaptor), which generally refers to oligonucleotides incorporated at the 5' and/or 3' ends of polynucleotides to facilitate one or more steps of a polynucleotide sequencing reaction. In some embodiments, a sequencing adapter is used to bind a polynucleotide comprising the sequencing adapter to a flow cell for next generation sequencing. Non-limiting examples of next-generation sequencing methods are single-molecule real-time sequencing, ion semiconductor sequencing, pyrosequencing, sequencing by synthesis, sequencing by ligation, and chain termination. Sequencing adapters for flow cell attachment may comprise any suitable sequence compatible with next generation sequencing systems, e.g., 454 Sequencing, Ion Torrent Proton or PGM, and Illumina X10. Non-limiting examples of sequencing adapters for next generation sequencing methods include P5 and P7 adapters suitable for use with Illumina sequencing systems; TruSeq Universal Adapter; and TruSeq Indexed Adapter. In some embodiments, a sequencing adapter can be used to enrich, e.g., via amplification, such as polymerase chain reaction (PCR), for polynucleotides comprising the adapter sequence. Sequencing adapters can further comprise a barcode sequence and/or a sample index sequence.

In certain other embodiments, a primer such as a third primer comprises a barcode sequence. A barcode sequence refers to a known nucleic acid sequence that allows some feature of a polynucleotide with which the barcode is associated to be identified. Barcodes can each have a length within a range of 5 to 35 nucleotides, 6 to 30 nucleotides, or 8 to 20 nucleotides. In some embodiments, barcodes are at least 3, 4, 5, 6, 7, 8, 9, 10, 11, 12, 13, 14, or 15 nucleotides in length. In some embodiments, barcodes are less than 6 nucleotides in length. In some embodiments, barcodes associated with some target polynucleotides may be a different length than barcodes associated with other target polynucleotides. The melting temperatures of barcodes within a set can be within ±10° C. of one another, within ±5° C. of one another, or within ±2° C. of one another. Barcodes can be members of a minimally cross-hybridizing set. For example, the nucleotide sequence of each member of such a set can be sufficiently different from that of every other member of the set that no member can form a stable duplex with the complement of any other member under moderate or stringent hybridization conditions. The nucleotide sequence of each member of a minimally cross-hybridizing set can differ from those of every other member by at least two nucleotides. Some barcode technologies are described in Winzeler et al. (1999) Science 285:901; Brenner (2000) Genome Biol. 1:1 Kumar et al. (2001) Nature Rev. 2:302; Giaever et al. (2004) Proc. Natl. Acad. Sci. USA 101:793; Eason et al. (2004) Proc. Natl. Acad. Sci. USA 101:11046; and Brenner (2004) Genome Biol. 5:240, each of which is herein incorporated in its entirety by reference.

Certain of embodiments of the present disclosure comprise sequencing a plurality of amplicons. A variety of sequencing methodologies are available for sequencing the plurality of amplicons. In some embodiments, high-throughput sequencing methodologies are used. Non-limiting examples of sequencing methodologies that can be used include sequencing systems manufactured by Illumina (sequencing systems such as HiSeq® and MiSeq®), Life Technologies (Ion Torrent®, SOLiD®, etc.), Roche's 454 Life Sciences systems, Pacific Biosciences systems, etc. In some embodiments, sequencing comprises use of HiSeq® and MiSeq® systems to produce reads of about or more than about 50, 75, 100, 125, 150, 175, 200, 250, 300 nucleotides or more in length. In some embodiments, sequencing comprises a sequencing-by-synthesis process, where individual nucleotides are identified iteratively, as they are added to the growing primer extension product. Pyrosequencing is an example of a sequence by synthesis process that identifies the incorporation of a nucleotide by assaying the resulting synthesis mixture for the presence of by-products of the sequencing reaction, namely pyrophosphate. In particular, a primer/template/polymerase complex is contacted with a single type of nucleotide. If that nucleotide is incorporated, the polymerization reaction cleaves the nucleoside triphosphate between the $\alpha$ and $\beta$ phosphates of the triphosphate chain, releasing pyrophosphate. The presence of released pyrophosphate is then identified using a chemiluminescent enzyme reporter system that converts the pyrophosphate, with AMP, into ATP, then measures ATP using a luciferase enzyme to produce measurable light signals. Where light is detected, the base is incorporated, where no light is detected, the base is not incorporated. Following appropriate washing steps, the various bases are cyclically contacted with the complex to sequentially identify subsequent bases in the template sequence. See, e.g., U.S. Pat. No. 6,210,891.

In some embodiments, the amplicons are sequenced to detect a sequence variant, e.g., inversion, deletion, duplication, translocation, and rare somatic mutations, with respect to a reference sequence or in a background of no mutations. In some embodiments, the sequence variant is correlated with disease. In some embodiments, the sequence variant is not correlated with disease. In general, sequence variants for which there is statistical, biological, and/or functional evidence of association with a disease or trait are referred to as "causal genetic variants." A single causal genetic variant can be associated with more than one disease or trait. In some cases, a causal genetic variant can be associated with a Mendelian trait, a non-Mendelian trait, or both. Causal genetic variants can manifest as variations in a polynucleotide, such 1, 2, 3, 4, 5, 6, 7, 8, 9, 10, 20, 50, or more sequence differences (such as between a polynucleotide comprising the causal genetic variant and a polynucleotide lacking the causal genetic variant at the same relative genomic position). Non-limiting examples of types of causal genetic variants include single nucleotide polymorphisms (SNP), deletion/insertion polymorphisms (DIP), copy number variants (CNV), short tandem repeats (STR), restriction fragment length polymorphisms (RFLP), simple sequence repeats (SSR), variable number of tandem repeats (VNTR), randomly amplified polymorphic DNA (RAPD), amplified fragment length polymorphisms (AFLP), inter-retrotransposon amplified polymorphisms (IRAP), long and short interspersed elements (LINE/SINE), long tandem repeats (LTR), mobile elements, retrotransposon microsatellite amplified polymorphisms, retrotransposon-based insertion polymorphisms, sequence specific amplified polymorphism, and heritable epigenetic modification (for example, DNA methylation). A causal genetic variant may also be a set of closely related causal genetic variants. Some causal genetic variants may exert influence as sequence variations in RNA polynucleotides. At this level, some causal genetic variants are also indicated by the presence or absence of a species of RNA polynucleotides. Also, some causal genetic variants result in sequence variations in protein polypeptides. A number of causal genetic variants have been reported. An example of a causal genetic variant that is a SNP is the Hb S variant of hemoglobin that causes sickle cell anemia. An example of a causal genetic variant that is a DIP is the delta508 mutation of the CFTR gene which causes cystic fibrosis. An example of a causal genetic variant that is a CNV is trisomy 21, which causes Down's syndrome. An example of a causal genetic variant that is an STR is tandem repeat that causes Huntington's disease. Additional non-limiting examples of causal genetic variants are described in WO2014015084. Additional non-limiting examples of methods for the identification of rare sequence variants are described in WO2015089333.

In certain embodiments of any of the various aspects of the present disclosure, amplicons are purified prior to sequencing. Amplicons can be purified by various methods. Amplicons may be purified to remove excess or unwanted reagents, reactants, or products. Amplicons may further be purified by size, sequence, or other physical or chemical characteristic. In some embodiments, amplicons may be subjected to size exclusion chromatography, whereby amplicons comprising only one copy of the target polynucleotide and/or small reagents (e.g., primers) are retained and discarded, or amplicons comprising two or more copies of the target polynucleotide are retained and released in a separate volume. In some embodiments, amplicons may be subjected to fragment excision from gels and gel filtration (e.g. to enrich for fragments larger than about 300, 400, 500, or more nucleotides in length); as well as SPRI beads (Agencourt AMPure XP) for size selection by fine-tuning the binding buffer concentration. For example, the use of 0.6× binding buffer during mixing with DNA fragments may be used to preferentially bind DNA fragments larger than about 500 base pairs (bp). In some embodiments, particularly where amplification with B2B primers has been performed, amplification products are treated to filter the resulting amplicons on the basis of size to reduce and/or eliminate the number of monomers a mixture comprising concatemers. This can be done using any purification technique as described elsewhere herein.

Embodiments of the disclosure provided herein can be used to enrich for amplicons comprising a variety of sequence variants associated with one or more kinds of cancer. Suitable target sequences of oncological significance that find use in the methods of the disclosure include, but are not limited to, alterations in the TP53 gene, the ALK gene, the KRAS gene, the PIK3CA gene, the BRAF gene, the EGFR gene, and the KIT gene. A target sequence the may be specifically amplified, and/or specifically analyzed for sequence variants may be all or part of a cancer-associated gene. In some embodiments, one or more sequence variants are identified in the TP53 gene. TP53 is one of the most frequently mutated genes in human cancers, for example, TP53 mutations are found in 45% of ovarian cancers, 43% of large intestinal cancers, and 42% of cancers of the upper aerodigestive track (see e.g. M. Olivier, et, al. TP53 Mutations in Human Cancers: Origins, Consequences, and Clinical Use. Cold Spring Harb Perspect Biol. 2010 January; 2(1). Characterization of the mutation status of TP53 can aid in clinical diagnosis, provide prognostic value, and influence treatment for cancer patients. For example, TP53 mutations may be used as a predictor of a poor prognosis for patients in CNS tumors derived from glial cells and a predictor of rapid disease progression in patients with chronic lymphocytic leukemia (see e.g. McLendon R E, et al. Cancer. 2005 Oct. 15; 1 04(8): 1693-9; Dicker F, et al. Leukemia. 2009 January; 23(1):117-24). Sequence variation can occur anywhere within the gene. Thus, all or part of the TP53 gene can be evaluated herein. That is, as described elsewhere herein, when target specific components (e.g. target specific primers) are used, a plurality of TP53 specific sequences can be used, for example to amplify and detect fragments spanning the gene, rather than just one or more selected subsequences (such as mutation "hot spots") as may be used for selected targets. Alternatively, target-specific primers may be designed that hybridize upstream or downstream of one or more selected subsequences (such a nucleotide or nucleotide region associated with an increased rate of mutation among a class of subjects, also encompassed by the term "hot spot"). Standard primers spanning such a subsequence may be designed, and/or B2B primers that hybridize upstream or downstream of such a subsequence may be designed.

In some embodiments, one or more sequence variants are identified in all or part of the ALK gene. ALK fusions have been reported in as many as 7% of lung tumors, some of which are associated with EGFR tyrosine kinase inhibitor (TKI) resistance (see e.g. Shaw et al., J Clin Oncol. Sep. 10, 2009; 27(26): 4247-4253). Up to 2013, several different point mutations spanning across the entire ALK tyrosine kinase domain have been found in patients with secondary resistance to the ALK tyrosine kinase inhibitor (TKI) (Katayama R 2012 Sci Transl Med. 2012 Feb. 8; 4(120)). Thus, mutation detection in ALK gene can be used to aid cancer therapy decisions.

In some embodiments, one or more sequence variants are identified in all or part of the KRAS gene. Approximately 15-25% of patients with lung adenocarcinoma and 40% of patients with colorectal cancer have been reported as harboring tumor associated KRAS mutations (see e.g. Neuman 2009, Pathol Res Pract. 2009; 205(12):858-62). Most of the mutations are located at codons 12, 13, and 61 of the KRAS gene. These mutations activate KRAS signaling pathways, which trigger growth and proliferation of tumor cells. Some studies indicate that patients with tumors harboring mutations in KRAS are unlikely to benefit from anti-EGFR antibody therapy alone or in combination with chemotherapy (see e.g. Amado et al. 2008 J Clin Oncol. 2008 Apr. 1; 26(1 0): 1626-34, Bokemeyer et al. 2009 J Clin Oncol. 2009 Feb. 10; 27(5):663-71). One particular "hot spot" for sequence variation that may be targeted for identifying sequence variation is at position 35 of the gene. Identification of KRAS sequence variants can be used in treatment selection, such as in treatment selection for a subject with colorectal cancer.

In some embodiments, one or more sequence variants are identified in all or part of the PIK3CA gene. Somatic mutations in PIK3CA have been frequently found in various type of cancers, for example, in 10-30% of colorectal cancers (see e.g. Samuels et al. 2004 Science. 2004 Apr. 23; 304(5670):554.). These mutations are most commonly located within two "hotspot" areas within exon 9 (the helical domain) and exon 20 (the kinase domain), which may be specifically targeted for amplification and/or analysis for the detection sequence variants. Position 3140 may also be specifically targeted.

In some embodiments, one or more sequence variants are identified in all or part of the BRAF gene. Near 50% of all malignant melanomas have been reported as harboring somatic mutations in BRAF (see e.g. Maldonado et al., J Natl Cancer Inst. 2003 Dec. 17; 95(24):1878-90). BRAF mutations are found in all melanoma subtypes but are most frequent in melanomas derived from skin without chronic sun-induced damage. Among the most common BRAF mutations in melanoma are missense mutations V600E, which substitutes valine at position 600 with glutamine. BRAF V600E mutations are associated with clinical benefit of BRAF inhibitor therapy. Detection of BRAF mutation can be used in melanoma treatment selection and studies of the resistance to the targeted therapy.

In some embodiments, one or more sequence variants are identified in all or part of the EGFR gene. EGFR mutations are frequently associated with Non-Small Cell Lung Cancer (about 10% in the US and 35% in East Asia; see e.g. Pao et al., Proc Natl Acad Sci USA. 2004 Sep. 7; 101(36):13306-11). These mutations typically occur within EGFR exons 18-21, and are usually heterozygous. Approximately 90% of these mutations are exon 19 deletions or exon 21 L858R point mutations.

In some embodiments, one or more sequence variants are identified in all or part of the KIT gene. Near 85% of Gastrointestinal Stromal Tumor (GIST) have been reported as harboring KIT mutations (see e.g. Heinrich et al. 2003 J Clin Oncol. 2003 December I; 21 (23):4342-9). The majority of KIT mutations are found in juxtamembrane domain (exon 11, 70%), extracellular dimerization motif (exon 9, 10-15%), tyrosine kinase I (TKI) domain (exon 13, 1-3%), and tyrosine kinase 2 (TK2) domain and activation loop (exon 17, 1-3%). Secondary KIT mutations are commonly identified after target therapy imatinib and after patients have developed resistance to the therapy.

Additional non-limiting examples of genes associated with cancer, all or a portion of which may be analyzed for sequence variants according to a method described herein include, but are not limited to PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR; (Androgen Receptor); TSG101; IGF; IGF Receptor; Igf1 (4 variants); Igf2 (3 variants); Igf 1

Receptor; Igf 2 Receptor; Bax; Bcl2; caspases family (9 members: 1, 2, 3, 4, 6, 7, 8, 9, 12); Kras; and Apc. Further examples are provided elsewhere herein. Examples of cancers that may be diagnosed based on calling one or more sequence variants in accordance with a method disclosed herein include, without limitation, Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, and combinations thereof.

Further non-limiting examples of genes associated with cancer, all or a portion of which (e.g., promoter region, intron, exon, etc.) which can be analyzed for sequence variants according to a method described herein are provided in Table 2.

TABLE 2

| Gene | Description |
| --- | --- |
| ABCC6 | ATP-binding cassette, sub-family C (CFTR/MRP), member 6 |
| ABI1 | abl-interactor 1 |
| ABL1 | c-abl oncogene 1, non-receptor tyrosine kinase |
| ABL2 | v-abl Abelson murine leukemia viral oncogene homolog 2 |
| ACSL3 | acyl-CoA synthetase long-chain family member 3 |
| ACSL6 | acyl-CoA synthetase long-chain family member 6 |
| AFF1 | AF4/FMR2 family, member 1 |
| AFF3 | AF4/FMR2 family, member 3 |
| AFF4 | AF4/FMR2 family, member 4 |
| AIP | aryl hydrocarbon receptor interacting protein |
| AKAP9 | A kinase (PRKA) anchor protein (yotiao) 9 |
| AKT1 | v-akt murine thymoma viral oncogene homolog 1 |
| AKT2 | v-akt murine thymoma viral oncogene homolog 2 |
| AKT3 | v-akt murine thymoma viral oncogene homolog 3 (protein kinase B, gamma) |
| ALDH2 | aldehyde dehydrogenase 2 family (mitochondrial) |
| ALK | anaplastic lymphoma receptor tyrosine kinase |
| APC | adenomatous polyposis coli |
| AR | androgen receptor |
| ARHGAP26 | Rho GTPase activating protein 26 |
| ARHGEF12 | Rho guanine nucleotide exchange factor (GEF) 12 |
| ARID1A | AT rich interactive domain 1A (SWI-like) |
| ARID1B | AT rich interactive domain 1B (SWI1-like) |
| ARID2 | AT rich interactive domain 2 (ARID, RFX-like) |
| ARID3A | AT rich interactive domain 3A (BRIGHT-like) |
| ARID3B | AT rich interactive domain 3B (BRIGHT-like) |
| ARID4A | AT rich interactive domain 4A (RBP1-like) |
| ARID4B | AT rich interactive domain 4B (RBP1-like) |
| ARID5A | AT rich interactive domain 5A (MRF1-like) |
| ARID5B | AT rich interactive domain 5B (MRF1-like) |
| ARNT | aryl hydrocarbon receptor nuclear translocator |
| ASPSCR1 | alveolar soft part sarcoma chromosome region, candidate 1 |
| ASXL1 | additional sex combs like 1 (*Drosophila*) |
| ATF1 | activating transcription factor 1 |
| ATIC | 5-aminoimidazole-4-carboxamide ribonucleotide formyltransferase/IMP cyclohydrolase |
| ATM | ataxia telangiectasia mutated |
| ATR | ataxia telangiectasia and Rad3 related |
| ATRX | alpha thalassemia/mental retardation syndrome X-linked |
| AURKA | aurora kinase A |
| AXIN2 | axin 2 |
| BAP1 | BRCA1 associated protein-1 (ubiquitin carboxy-terminal hydrolase) |
| BCL10 | B-cell CLL/lymphoma 10 |
| BCL11A | B-cell CLL/lymphoma 11A (zinc finger protein) |
| BCL11B | B-cell CLL/lymphoma 11B (zinc finger protein) |
| BCL2 | B-cell CLL/lymphoma 2 |
| BCL3 | B-cell CLL/lymphoma 3 |
| BCL6 | B-cell CLL/lymphoma 6 |
| BCL7A | B-cell CLL/lymphoma 7A |
| BCL9 | B-cell CLL/lymphoma 9 |
| BCOR | BCL6 corepressor |
| BCR | breakpoint cluster region |
| BIRC3 | baculoviral IAP repeat containing 3 |
| BLID | BH3-like motif containing, cell death inducer |
| BLM | Bloom syndrome, RecQhelicase-like |

TABLE 2-continued

| Gene | Description |
| --- | --- |
| BMPR1A | bone morphogenetic protein receptor, type IA |
| BRAF | v-raf murine sarcoma viral oncogene homolog B1 |
| BRCA1 | breast cancer 1, early onset |
| BRCA2 | breast cancer 2, early onset |
| BRD3 | bromodomain containing 3 |
| BRD4 | bromodomain containing 4 |
| BRIP1 | BRCA1 interacting protein C-terminal helicase 1 |
| BTG1 | B-cell translocation gene 1, anti-proliferative |
| BUB1B | budding uninhibited by benzimidazoles 1 homolog beta (yeast) |
| C15orf55 | chromosome 15 open reading frame 55 |
| CANT1 | calcium activated nucleotidase 1 |
| CARD11 | caspase recruitment domain family, member 11 |
| CARS | cysteinyl-tRNA synthetase |
| CASC5 | cancer susceptibility candidate 5 |
| CBFA2T3 | core-binding factor, runt domain, alpha subunit 2; translocated to, 3 |
| CBFB | core-binding factor, beta subunit |
| CBL | Cbl proto-oncogene, E3 ubiquitin protein ligase |
| CBLB | Cbl proto-oncogene, E3 ubiquitin protein ligase B |
| CBLC | Cbl proto-oncogene, E3 ubiquitin protein ligase C |
| CCDC6 | coiled-coil domain containing 6 |
| CCNB1IP1 | cyclin B1 interacting protein 1, E3 ubiquitin protein ligase |
| CCND1 | cyclin D1 |
| CCND2 | cyclin D2 |
| CCND3 | cyclin D3 |
| CCNE1 | cyclin E1 |
| CD274 | CD274 molecule |
| CD74 | CD74 molecule, major histocompatibility complex, class II invariant chain |
| CD79A | CD79a molecule, immunoglobulin-associated alpha |
| CD79B | CD79b molecule, immunoglobulin-associated beta |
| CDC73 | cell division cycle 73, Paf1/RNA polymerase II complex component, homolog (*S. cerevisiae*) |
| CDH1 | cadherin 1, type 1, E-cadherin (epithelial) |
| CDH11 | cadherin 11, type 2, OB-cadherin (osteoblast) |
| CDH6 | cadherin 6, type 2, K-cadherin (fetal kidney) |
| CDK12 | cyclin-dependent kinase 12 |
| CDK2AP2 | cyclin-dependent kinase 2 associated protein 2 |
| CDK4 | cyclin-dependent kinase 4 |
| CDK6 | cyclin-dependent kinase 6 |
| CDK8 | cyclin-dependent kinase 8 |
| CDKN1A | cyclin-dependent kinase inhibitor 1A (p21, Cip1) |
| CDKN1B | cyclin-dependent kinase inhibitor 1B (p27, Kip1) |
| CDKN2A | cyclin-dependent kinase inhibitor 2A |
| CDKN2B | cyclin-dependent kinase inhibitor 2B (p15, inhibits CDK4) |
| CDKN2C | cyclin-dependent kinase inhibitor 2C (p18, inhibits CDK4) |
| CDKN2D | cyclin-dependent kinase inhibitor 2D (p19, inhibits CDK4) |
| CDX2 | caudal type homeobox 2 |
| CEBPA | CCAAT/enhancer binding protein (C/EBP), alpha |
| CHCHD7 | coiled-coil-helix-coiled-coil-helix domain containing 7 |
| CHD5 | chromodomain helicase DNA binding protein 5 |
| CHD6 | chromodomain helicase DNA binding protein 6 |
| CHEK1 | checkpoint kinase 1 |
| CHEK2 | checkpoint kinase 2 |
| CHIC2 | cysteine-rich hydrophobic domain 2 |
| CHN1 | chimerin (chimaerin) 1 |
| CIC | capicua homolog (*Drosophila*) |
| CIITA | class II, major histocompatibility complex, transactivator |
| CLP1 | CLP1, cleavage and polyadenylation factor I subunit, homolog (*S. cerevisiae*) |
| CLTC | clathrin, heavy chain (Hc) |
| CLTCL1 | clathrin, heavy chain-like 1 |
| CNBP | CCHC-type zinc finger, nucleic acid binding protein |
| CNTRL | centriolin |
| COL1A1 | collagen, type I, alpha 1 |
| COX6C | cytochrome c oxidase subunit VIc |
| CREB1 | cAMP responsive element binding protein 1 |
| CREB3L1 | cAMP responsive element binding protein 3-like 1 |
| CREB3L2 | cAMP responsive element binding protein 3-like 2 |
| CREBBP | CREB binding protein |
| CRKL | v-crk sarcoma virus CT10 oncogene homolog (avian)-like |
| CRLF2 | cytokine receptor-like factor 2 |

TABLE 2-continued

| Gene | Description |
|---|---|
| CRTC1 | CREB regulated transcription coactivator 1 |
| CRTC3 | CREB regulated transcription coactivator 3 |
| CSF1R | colony stimulating factor 1 receptor |
| CTNNB1 | catenin (cadherin-associated protein), beta 1, 88 kDa |
| CXCR7 | chemokine (C-X-C motif) receptor 7 |
| CYLD | cylindromatosis (turban tumor syndrome) |
| CYP1B1 | cytochrome P450, family 1, subfamily B, polypeptide 1 |
| DAXX | death-domain associated protein |
| DDB2 | damage-specific DNA binding protein 2, 48 kDa |
| DDIT3 | DNA-damage-inducible transcript 3 |
| DDX10 | DEAD (Asp-Glu-Ala-Asp) box polypeptide 10 ("DEAD" disclosed as SEQ ID NO: 86) |
| DDX5 | DEAD (Asp-Glu-Ala-Asp) box helicase 5 ("DEAD" disclosed as SEQ ID NO: 86) |
| DDX6 | DEAD (Asp-Glu-Ala-Asp) box helicase 6 ("DEAD" disclosed as SEQ ID NO: 86) |
| DEK | DEK oncogene |
| DICER1 | dicer 1, ribonuclease type III |
| DNMT3A | DNA (cytosine-5-)-methyltransferase 3 alpha |
| DUX4 | double homeobox 4 |
| EBF1 | early B-cell factor 1 |
| EGFR | epidermal growth factor receptor |
| EIF4A2 | eukaryotic translation initiation factor 4A2 |
| ELAC2 | elaC homolog 2 (*E. coli*) |
| ELF4 | E74-like factor 4 (ets domain transcription factor) |
| ELK4 | ELK4, ETS-domain protein (SRF accessory protein 1) |
| ELL | elongation factor RNA polymerase II |
| ELN | elastin |
| EML4 | echinoderm microtubule associated protein like 4 |
| EP300 | E1A binding protein p300 |
| EPCAM | epithelial cell adhesion molecule |
| EPHA10 | EPH receptor A10 |
| EPHA3 | EPH receptor A3 |
| EPHA5 | EPH receptor A5 |
| EPHA6 | EPH receptor A6 |
| EPHB6 | EPH receptor B6 |
| EPS15 | epidermal growth factor receptor pathway substrate 15 |
| ERBB2 | v-erb-b2 erythroblastic leukemia viral oncogene homolog 2, neuro/glioblastoma derived oncogene homolog (avian) |
| ERBB3 | v-erb-b2 erythroblastic leukemia viral oncogene homolog 3 (avian) |
| ERBB4 | v-erb-a erythroblastic leukemia viral oncogene homolog 4 (avian) |
| ERC1 | ELKS/RAB6-interacting/CAST family member 1 |
| ERCC1 | excision repair cross-complementing rodent repair deficiency, complementation group 1 (includes overlapping antisense sequence) |
| ERCC2 | excision repair cross-complementing rodent repair deficiency, complementation group 2 |
| ERCC3 | excision repair cross-complementing rodent repair deficiency, complementation group 3 |
| ERCC4 | excision repair cross-complementing rodent repair deficiency, complementation group 4 |
| ERCC5 | excision repair cross-complementing rodent repair deficiency, complementation group 5 |
| ERG | v-ets erythroblastosis virus E26 oncogene homolog (avian) |
| ETV1 | ets variant 1 |
| ETV4 | ets variant 4 |
| ETV5 | ets variant 5 |
| ETV6 | ets variant 6 |
| EWSR1 | Ewing sarcoma breakpoint region 1 |
| EXT1 | exostosin 1 |
| EXT2 | exostosin 2 |
| EZH2 | enhancer of zeste homolog 2 (*Drosophila*) |
| FAM123B | family with sequence similarity 123B |
| FAM22A | family with sequence similarity 22, member A |
| FAM22B | family with sequence similarity 22, member B |
| FAM46C | family with sequence similarity 46, member C |
| FANCA | Fanconi anemia, complementation group A |
| FANCC | Fanconi anemia, complementation group C |
| FANCD2 | Fanconi anemia, complementation group D2 |
| FANCE | Fanconi anemia, complementation group E |
| FANCF | Fanconi anemia, complementation group F |
| FANCG | Fanconi anemia, complementation group G |
| FAS | Fas (TNF receptor superfamily, member 6) |
| FBXO11 | F-box protein 11 |
| FBXW7 | F-box and WD repeat domain containing 7, E3 ubiquitin protein ligase |
| FCGR2B | Fc fragment of IgG, low affinity IIb, receptor (CD32) |
| FCRL4 | Fc receptor-like 4 |
| FEV | FEV (ETS oncogene family) |
| FGF23 | fibroblast growth factor 23 |
| FGFR1 | fibroblast growth factor receptor 1 |
| FGFR1OP | FGFR1 oncogene partner |
| FGFR2 | fibroblast growth factor receptor 2 |
| FGFR3 | fibroblast growth factor receptor 3 |
| FGFR4 | fibroblast growth factor receptor 4 |
| FH | fumarate hydratase |
| FHIT | fragile histidine triad |
| FHL1 | four and a half LIM domains 1 |
| FIP1L1 | FIP1 like 1 (*S. cerevisiae*) |
| FKBP1B | FK506 binding protein 1B, 12.6 kDa |
| FKBP9 | FK506 binding protein 9, 63 kDa |
| FLCN | folliculin |
| FLI1 | Friend leukemia virus integration 1 |
| FLT | uncharacterized protein LOC145788 |
| FLT3 | fms-related tyrosine kinase 3 |
| FLT4 | fms-related tyrosine kinase 4 |
| FNBP1 | formin binding protein 1 |
| FOLR1 | folate receptor 1 (adult) |
| FOXC1 | forkhead box C1 |
| FOXL2 | forkhead box L2 |
| FOXO1 | forkhead box O1 |
| FOXO3 | forkhead box O3 |
| FOXO4 | forkhead box O4 |
| FOXP1 | forkhead box P1 |
| FSTL3 | follistatin-like 3 (secreted glycoprotein) |
| FUBP1 | far upstream element (FUSE) binding protein 1 |
| FUS | fused in sarcoma |
| GALNT3 | UDP-N-acetyl-alpha-D-galactosamine: polypeptide N-acetylgalactosaminyltransferase 3 (GalNAc-T3) |
| GAS7 | growth arrest-specific 7 |
| GATA1 | GATA binding protein 1 (globin transcription factor 1) |
| GATA2 | GATA binding protein 2 |
| GATA3 | GATA binding protein 3 |
| GLMN | glomulin, FKBP associated protein |
| GMPS | guanine monophosphate synthetase |
| GNA11 | guanine nucleotide binding protein (G protein), alpha 11 (Gq class) |
| GNAQ | guanine nucleotide binding protein (G protein), q polypeptide |
| GNAS | GNAS complex locus |
| GOLGA5 | golgin A5 |
| GOPC | golgi-associated PDZ and coiled-coil motif containing |
| GPC3 | glypican 3 |
| GPHN | gephyrin |
| GSTM1 | glutathione S-transferase mu 1 |
| GUCY1A2 | guanylate cyclase 1, soluble, alpha 2 |
| HECW1 | HECT, C2 and WW domain containing E3 ubiquitin protein ligase 1 |
| HERPUD1 | homocysteine-inducible, endoplasmic reticulum stress-inducible, ubiquitin-like domain like domain member 1 |
| HEY1 | hairy/enhancer-of-split related with YRPW motif 1 |
| HIP1 | huntingtin interacting protein 1 |
| HIST1H4I | histone cluster 1, H4i |
| HLF | hepatic leukemia factor |
| HMGA1 | high mobility group AT-hook 1 |
| HMGA2 | high mobility group AT-hook 2 |
| HMGN2P46 | high mobility group nucleosomal binding domain 2 pseudogene 46 |
| HNF1A | HNF1 homeobox A |
| HNRNPA2B1 | heterogeneous nuclear ribonucleoprotein A2/B1 |
| HOOK3 | hook homolog 3 (*Drosophila*) |
| HOXA11 | homeobox A11 |
| HOXA13 | homeobox A13 |
| HOXA9 | homeobox A9 |
| HOXC11 | homeobox C11 |
| HOXC13 | homeobox C13 |
| HOXD11 | homeobox D11 |
| HOXD13 | homeobox D13 |
| HRAS | v-Ha-ras Harvey rat sarcoma viral oncogene homolog |
| HSD17B3 | hydroxysteroid (17-beta) dehydrogenase 3 |
| HSD3B2 | hydroxy-delta-5-steroid dehydrogenase, 3 beta- and steroid delta-isomerase 2 |

TABLE 2-continued

| Gene | Description |
|---|---|
| HSP90AA1 | heat shock protein 90 kDa alpha (cytosolic), class A member 1 |
| HSP90AB1 | heat shock protein 90 kDa alpha (cytosolic), class B member 1 |
| IDH1 | isocitrate dehydrogenase 1 (NADP+), soluble |
| IDH2 | isocitrate dehydrogenase 2 (NADP+), mitochondrial |
| IGF1R | insulin-like growth factor 1 receptor |
| IKBKE | inhibitor of kappa light polypeptide gene enhancer in B-cells, kinase epsilon |
| IKZF1 | IKAROS family zinc finger 1 (Ikaros) |
| IL2 | interleukin 2 |
| IL21R | interleukin 21 receptor |
| IL6ST | interleukin 6 signal transducer (gp130, oncostatin M receptor) |
| IL7R | interleukin 7 receptor |
| IRF4 | interferon regulatory factor 4 |
| ITK | IL2-inducible T-cell kinase |
| JAK1 | Janus kinase 1 |
| JAK2 | Janus kinase 2 |
| JAK3 | Janus kinase 3 |
| JAZF1 | JAZF zinc finger 1 |
| JUN | jun proto-oncogene |
| KAT6A | K(lysine) acetyltransferase 6A |
| KAT6B | K(lysine) acetyltransferase 6B |
| KDM5A | lysine (K)-specific demethylase 5A |
| KDM5C | lysine (K)-specific demethylase 5C |
| KDM6A | lysine (K)-specific demethylase 6A |
| KDR | kinase insert domain receptor (a type III receptor tyrosine kinase) |
| KDSR | 3-ketodihydrosphingosine reductase |
| KEAP1 | kelch-like ECH-associated protein 1 |
| KIAA1549 | KIAA1549 |
| KIF1B | kinesin family member 1B |
| KIT | v-kit Hardy-Zuckerman 4 feline sarcoma viral oncogene homolog |
| KL | klotho |
| KLF6 | Kruppel-like factor 6 |
| KLK2 | kallikrein-related peptidase 2 |
| KRAS | v-Ki-ras2 Kirsten rat sarcoma viral oncogene homolog |
| KRT17 | keratin 17 |
| KTN1 | kinectin 1 (kinesin receptor) |
| LASP1 | LIM and SH3 protein 1 |
| LCK | lymphocyte-specific protein tyrosine kinase |
| LCP1 | lymphocyte cytosolic protein 1 (L-plastin) |
| LHFP | lipoma HMGIC fusion partner |
| LIFR | leukemia inhibitory factor receptor alpha |
| LMO1 | LIM domain only 1 (rhombotin 1) |
| LMO2 | LIM domain only 2 (rhombotin-like 1) |
| LPP | LIM domain containing preferred translocation partner in lipoma |
| LRP5 | low density lipoprotein receptor-related protein 5 |
| LTBP2 | latent transforming growth factor beta binding protein 2 |
| LTBP3 | latent transforming growth factor beta binding protein 3 |
| LYL1 | lymphoblastic leukemia derived sequence 1 |
| MAD2L1BP | MAD2L1 binding protein |
| MAF | v-maf musculoaponeurotic fibrosarcoma oncogene homolog (avian) |
| MAFB | v-maf musculoaponeurotic fibrosarcoma oncogene homolog B (avian) |
| MALAT1 | metastasis associated lung adenocarcinoma transcript 1 (non-protein coding) |
| MALT1 | mucosa associated lymphoid tissue lymphoma translocation gene 1 |
| MAML2 | mastermind-like 2 (Drosophila) |
| MAP2K1 | mitogen-activated protein kinase kinase 1 |
| MAP2K2 | mitogen-activated protein kinase kinase 2 |
| MAP2K4 | mitogen-activated protein kinase kinase 4 |
| MAP3K1 | mitogen-activated protein kinase kinase kinase 1, E3 ubiquitin protein ligase |
| MAP3K8 | mitogen-activated protein kinase kinase kinase 8 |
| MAX | MYC associated factor X |
| MC1R | melanocortin 1 receptor (alpha melanocyte stimulating hormone receptor) |
| MCL1 | myeloid cell leukemia sequence 1 (BCL2-related) |
| MDM2 | Mdm2, p53 E3 ubiquitin protein ligase homolog (mouse) |
| MDM4 | Mdm4 p53 binding protein homolog (mouse) |
| MDS2 | myelodysplastic syndrome 2 translocation associated |
| MECOM | MDS1 and EVI1 complex locus |
| MED12 | mediator complex subunit 12 |
| MEN1 | multiple endocrine neoplasia I |
| MET | met proto-oncogene (hepatocyte growth factor receptor) |
| MITF | microphthalmia-associated transcription factor |
| MKL1 | mega karyoblastic leukemia (translocation) 1 |
| MLF1 | myeloid leukemia factor 1 |
| MLH1 | mutL homolog 1, colon cancer, nonpolyposis type 2 (E. coli) |
| MLL | myeloid/lymphoid or mixed-lineage leukemia (trithorax homolog, Drosophila) |
| MLL2 | myeloid/lymphoid or mixed-lineage leukemia 2 |
| MLL3 | myeloid/lymphoid or mixed-lineage leukemia 3 |
| MLLT1 | myeloid/lymphoid or mixed-lineage leukemia (trithorax homolog, Drosophila); translocated to, 1 |
| MLLT10 | myeloid/lymphoid or mixed-lineage leukemia (trithorax homolog, Drosophila); translocated to, 10 |
| MLLT11 | myeloid/lymphoid or mixed-lineage leukemia (trithorax homolog, Drosophila); translocated to, 11 |
| MLLT3 | myeloid/lymphoid or mixed-lineage leukemia (trithorax homolog, Drosophila); translocated to, 3 |
| MLLT4 | myeloid/lymphoid or mixed-lineage leukemia (trithorax homolog, Drosophila); translocated to, 4 |
| MLLT6 | myeloid/lymphoid or mixed-lineage leukemia (trithorax homolog, Drosophila); translocated to, 6 |
| MN1 | meningioma (disrupted in balanced translocation) 1 |
| MNX1 | motor neuron and pancreas homeobox 1 |
| MPL | myeloproliferative leukemia virus oncogene |
| MRE11A | MRE11 meiotic recombination 11 homolog A (S. cerevisiae) |
| MSH2 | mutS homolog 2, colon cancer, nonpolyposis type 1 (E. coli) |
| MSH6 | mutS homolog 6 (E. coli) |
| MSI2 | musashi homolog 2 (Drosophila) |
| MSN | moesin |
| MTCP1 | mature T-cell proliferation 1 |
| MTCP1NB | mature T-cell proliferation 1 neighbor |
| MTOR | mechanistic target of rapamycin (serine/threonine kinase) |
| MTUS2 | microtubule associated tumor suppressor candidate 2 |
| MUC1 | mucin 1, cell surface associated |
| MUTYH | mutY homolog (E. coli) |
| MYB | v-myb myeloblastosis viral oncogene homolog (avian) |
| MYC | v-myc myelocytomatosis viral oncogene homolog (avian) |
| MYCL1 | v-myc myelocytomatosis viral oncogene homolog 1, lung carcinoma derived (avian) |
| MYCN | v-myc myelocytomatosis viral related oncogene, neuroblastoma derived (avian) |
| MYD88 | myeloid differentiation primary response gene (88) |
| MYH11 | myosin, heavy chain 11, smooth muscle |
| MYH9 | myosin, heavy chain 9, non-muscle |
| MYOC | myocilin, trabecular meshwork inducible glucocorticoid response |
| NACA | nascent polypeptide-associated complex alpha subunit |
| NBN | nibrin |
| NCKIPSD | NCK interacting protein with SH3 domain |
| NCOA1 | nuclear receptor coactivator 1 |
| NCOA2 | nuclear receptor coactivator 2 |
| NCOA4 | nuclear receptor coactivator 4 |
| NDRG1 | N-myc downstream regulated 1 |
| NF1 | neurofibromin 1 |
| NF2 | neurofibromin 2 (merlin) |
| NFE2L2 | nuclear factor (erythroid-derived 2)-like 2 |
| NFIB | nuclear factor I/B |
| NFKB2 | nuclear factor of kappa light polypeptide gene enhancer in B-cells 2 (p49/p100) |
| NIN | ninein (GSK3B interacting protein) |
| NKX2-1 | NK2 homeobox 1 |
| NONO | non-POU domain containing, octamer-binding |
| NOTCH1 | notch 1 |
| NOTCH2 | notch 2 |
| NOTCH3 | notch 3 |
| NOTCH4 | notch 4 |
| NPM1 | nucleophosmin (nucleolar phosphoprotein B23, numatrin) |
| NR4A3 | nuclear receptor subfamily 4, group A, member 3 |
| NRAS | neuroblastoma RAS viral (v-ras) oncogene homolog |
| NSD1 | nuclear receptor binding SET domain protein 1 |

TABLE 2-continued

| Gene | Description |
|---|---|
| NTRK1 | neurotrophic tyrosine kinase, receptor, type 1 |
| NTRK2 | neurotrophic tyrosine kinase, receptor, type 2 |
| NTRK3 | neurotrophic tyrosine kinase, receptor, type 3 |
| NUMA1 | nuclear mitotic apparatus protein 1 |
| NUP214 | nucleoporin 214 kDa |
| NUP98 | nucleoporin 98 kDa |
| OLIG2 | oligodendrocyte lineage transcription factor 2 |
| OMD | osteomodulin |
| OPTN | optineurin |
| P2RY8 | purinergic receptor P2Y, G-protein coupled, 8 |
| PAFAH1B2 | platelet-activating factor acetylhydrolase 1b, catalytic subunit 2 (30 kDa) |
| PAK7 | p21 protein (Cdc42/Rac)-activated kinase 7 |
| PALB2 | partner and localizer of BRCA2 |
| PALLD | palladin, cytoskeletal associated protein |
| PATZ1 | POZ (BTB) and AT hook containing zinc finger 1 |
| PAX2 | paired box 2 |
| PAX3 | paired box 3 |
| PAX5 | paired box 5 |
| PAX6 | paired box 6 |
| PAX7 | paired box 7 |
| PAX8 | paired box 8 |
| PBRM1 | polybromo 1 |
| PBX1 | pre-B-cell leukemia homeobox 1 |
| PCM1 | pericentriolar material 1 |
| PCSK7 | proprotein convertase subtilisin/kexin type 7 |
| PDCD1LG2 | programmed cell death 1 ligand 2 |
| PDE4DIP | phosphodiesterase 4D interacting protein |
| PDGFB | platelet-derived growth factor beta polypeptide |
| PDGFRA | platelet-derived growth factor receptor, alpha polypeptide |
| PDGFRB | platelet-derived growth factor receptor, beta polypeptide |
| PDPK1 | 3-phosphoinositide dependent protein kinase-1 |
| PER1 | period homolog 1 (Drosophila) |
| PHF6 | PHD finger protein 6 |
| PHOX2B | paired-like homeobox 2b |
| PICALM | phosphatidylinositol binding clathrin assembly protein |
| PIK3CA | phosphoinositide-3-kinase, catalytic, alpha polypeptide |
| PIK3R1 | phosphoinositide-3-kinase, regulatory subunit 1 (alpha) |
| PIM1 | pim-1 oncogene |
| PLAG1 | pleiomorphic adenoma gene 1 |
| PLK1 | polo-like kinase 1 |
| PML | promyelocytic leukemia |
| PMS1 | PMS1 postmeiotic segregation increased 1 (S. cerevisiae) |
| PMS2 | PMS2 postmeiotic segregation increased 2 (S. cerevisiae) |
| POU2AF1 | POU class 2 associating factor 1 |
| POU5F1 | POU class 5 homeobox 1 |
| PPARG | peroxisome proliferator-activated receptor gamma |
| PPP2R1A | protein phosphatase 2, regulatory subunit A, alpha |
| PRCC | papillary renal cell carcinoma (translocation-associated) |
| PRDM1 | PR domain containing 1, with ZNF domain |
| PRDM16 | PR domain containing 16 |
| PRF1 | perforin 1 (pore forming protein) |
| PRKAR1A | protein kinase, cAMP-dependent, regulatory, type I, alpha (tissue specific extinguisher 1) |
| PRKDC | protein kinase, DNA-activated, catalytic polypeptide |
| PRRX1 | paired related homeobox 1 |
| PSIP1 | PC4 and SFRS1 interacting protein 1 |
| PTCH1 | patched 1 |
| PTEN | phosphatase and tensin homolog |
| PTK2 | PTK2 protein tyrosine kinase 2 |
| PTK2B | PTK2B protein tyrosine kinase 2 beta |
| PTPN11 | protein tyrosine phosphatase, non-receptor type 11 |
| PTPRD | protein tyrosine phosphatase, receptor type, D |
| RABEP1 | rabaptin, RAB GTPase binding effector protein 1 |
| RAD51B | RAD51 homolog B (S. cerevisiae) |
| RAF1 | v-raf-1 murine leukemia viral oncogene homolog 1 |
| RALGDS | ral guanine nucleotide dissociation stimulator |
| RANBP17 | RAN binding protein 17 |
| RAP1GDS1 | RAP1, GTP-GDP dissociation stimulator 1 |
| RARA | retinoic acid receptor, alpha |
| RB1 | retinoblastoma 1 |
| RBM15 | RNA binding motif protein 15 |
| RECQL4 | RecQ protein-like 4 |
| REL | v-rel reticuloendotheliosis viral oncogene homolog (avian) |
| RET | ret proto-oncogene |
| RHOH | ras homolog family member H |
| RICTOR | RPTOR independent companion of MTOR, complex 2 |
| RMI2 | RMI2, RecQ mediated genome instability 2, homolog (S. cerevisiae) |
| RNASEL | ribonuclease L (2,5-oligoisoadenylate synthetase-dependent) |
| ROS1 | c-ros oncogene 1, receptor tyrosine kinase |
| RPL22 | ribosomal protein L22 |
| RPN1 | ribophorin I |
| RPTOR | regulatory associated protein of MTOR, complex 1 |
| RRM1 | ribonucleotide reductase M1 |
| RUNX1 | runt-related transcription factor 1 |
| RUNX1T1 | runt-related transcription factor 1; translocated to, 1 (cyclin D-related) |
| SARDH | sarcosine dehydrogenase |
| SBDS | Shwachman-Bodian-Diamond syndrome |
| SDHAF2 | succinate dehydrogenase complex assembly factor 2 |
| SDHB | succinate dehydrogenase complex, subunit B, iron sulfur (Ip) |
| SDHC | succinate dehydrogenase complex, subunit C, integral membrane protein, 15 kDa |
| SDHD | succinate dehydrogenase complex, subunit D, integral membrane protein |
| SEPT5 | septin 5 |
| SEPT6 | septin 6 |
| SEPT9 | septin 9 |
| SET | SET nuclear oncogene |
| SETD2 | SET domain containing 2 |
| SETDB1 | SET domain, bifurcated 1 |
| SF3B1 | splicing factor 3b, subunit 1, 155 kDa |
| SF3B2 | splicing factor 3b, subunit 2, 145 kDa |
| SFPQ | splicing factor proline/glutamine-rich |
| SH3GL1 | 5H3-domain GRB2-like 1 |
| SLC45A3 | solute carrier family 45, member 3 |
| SMAD2 | SMAD family member 2 |
| SMAD3 | SMAD family member 3 |
| SMAD4 | SMAD family member 4 |
| SMARCA4 | SWI/SNF related, matrix associated, actin dependent regulator of chromatin, subfamily a, member 4 |
| SMARCB1 | SWI/SNF related, matrix associated, actin dependent regulator of chromatin, subfamily b, member 1 |
| SMO | smoothened, frizzled family receptor |
| SNX29 | sorting nexin 29 |
| SOCS1 | suppressor of cytokine signaling 1 |
| SOX2 | SRY (sex determining region Y)-box 2 |
| SPECC1 | sperm antigen with calponin homology and coiled-coil domains 1 |
| SPEN | spen homolog, transcriptional regulator (Drosophila) |
| SRC | v-src sarcoma (Schmidt-Ruppin A-2) viral oncogene homolog (avian) |
| SRD5A2 | steroid-5-alpha-reductase, alpha polypeptide 2 (3-oxo-5 alpha-steroid delta 4-dehydrogenase alpha 2) |
| SRGAP3 | SLIT-ROBO Rho GTPase activating protein 3 |
| SRSF2 | serine/arginine-rich splicing factor 2 |
| SRSF3 | serine/arginine-rich splicing factor 3 |
| SS18 | synovial sarcoma translocation, chromosome 18 |
| SS18L1 | synovial sarcoma translocation gene on chromosome 18-like 1 |
| SSX1 | synovial sarcoma, X breakpoint 1 |
| SSX2 | synovial sarcoma, X breakpoint 2 |
| SSX4 | synovial sarcoma, X breakpoint 4 |
| STAT3 | signal transducer and activator of transcription 3 (acute-phase response factor) |
| STIL | SCL/TAL1 interrupting locus |
| STK11 | serine/threonine kinase 11 |
| STX11 | syntaxin 11 |
| STXBP2 | syntaxin binding protein 2 |
| SUFU | suppressor of fused homolog (Drosophila) |
| SUZ12 | suppressor of zeste 12 homolog (Drosophila) |
| SYK | spleen tyrosine kinase |
| TAF15 | TAF15 RNA polymerase II, TATA box binding protein (TBP)-associated factor, 68 kDa |
| TAL1 | T-cell acute lymphocytic leukemia 1 |
| TAL2 | T-cell acute lymphocytic leukemia 2 |
| TCEA1 | transcription elongation factor A (SII), 1 |
| TCEA1P2 | transcription elongation factor A (SII), 1 pseudogene 2 |
| TCF12 | transcription factor 12 |

TABLE 2-continued

| Gene | Description |
| --- | --- |
| TCF3 | transcription factor 3 (E2A immunoglobulin enhancer binding factors E12/E47) |
| TCF4 | transcription factor 4 |
| TCF7L2 | transcription factor 7-like 2 (T-cell specific, HMG-box) |
| TCL1A | T-cell leukemia/lymphoma 1A |
| TCL6 | T-cell leukemia/lymphoma 6 (non-protein coding) |
| TERT | telomerase reverse transcriptase |
| TET1 | tet methylcytosine dioxygenase 1 |
| TET2 | tet methylcytosine dioxygenase 2 |
| TFE3 | transcription factor binding to IGHM enhancer 3 |
| TFEB | transcription factor EB |
| TFG | TRK-fused gene |
| TFPT | TCF3 (E2A) fusion partner (in childhood Leukemia) |
| TFRC | transferrin receptor (p90, CD71) |
| TGFBR2 | transforming growth factor, beta receptor II (70/80 kDa) |
| THRAP3 | thyroid hormone receptor associated protein 3 |
| TLX1 | T-cell leukemia homeobox 1 |
| TLX3 | T-cell leukemia homeobox 3 |
| TMEM127 | transmembrane protein 127 |
| TMPRSS2 | transmembrane protease, serine 2 |
| TNFAIP3 | tumor necrosis factor, alpha-induced protein 3 |
| TNFRSF14 | tumor necrosis factor receptor superfamily, member 14 |
| TNFRSF17 | tumor necrosis factor receptor superfamily, member 17 |
| TOP1 | topoisomerase (DNA) I |
| TOP2A | topoisomerase (DNA) II alpha 170 kDa |
| TP53 | tumor protein p53 |
| TPM3 | tropomyosin 3 |
| TPM4 | tropomyosin 4 |
| TPR | translocated promoter region, nuclear basket protein |
| TRIM24 | tripartite motif containing 24 |
| TRIM27 | tripartite motif containing 27 |
| TRIM33 | tripartite motif containing 33 |
| TRIP11 | thyroid hormone receptor interactor 11 |
| TSC1 | tuberous sclerosis 1 |
| TSC2 | tuberous sclerosis 2 |
| TSHR | thyroid stimulating hormone receptor |
| TTL | tubulin tyrosine ligase |
| TYK2 | tyrosine kinase 2 |
| U2AF1 | U2 small nuclear RNA auxiliary factor 1 |
| UNC13D | unc-13 homolog D (C. elegans) |
| USP6 | ubiquitin specific peptidase 6 (Tre-2 oncogene) |
| UTY | ubiquitously transcribed tetratricopeptide repeat gene, Y-linked |
| VHL | von Hippel-Lindau tumor suppressor, E3 ubiquitin protein ligase |
| VTI1A | vesicle transport through interaction with t-SNAREs homolog 1A (yeast) |
| WAS | Wiskott-Aldrich syndrome (eczema-thrombocytopenia) |
| WDR36 | WD repeat domain 36 |
| WHSC1 | Wolf-Hirschhorn syndrome candidate 1 |
| WHSC1L1 | Wolf-Hirschhorn syndrome candidate 1-like 1 |
| WIF1 | WNT inhibitory factor 1 |
| WRN | Werner syndrome, RecQ helicase-like |
| WT1 | Wilms tumor 1 |
| XPA | xeroderma pigmentosum, complementation group A |
| XPC | xeroderma pigmentosum, complementation group C |
| XPO1 | exportin 1 (CRM1 homolog, yeast) |
| YWHAE | tyrosine 3-monooxygenase/tryptophan 5-monooxygenase activation protein, epsilon polypeptide |
| ZBTB16 | zinc finger and BTB domain containing 16 |
| ZMYM2 | zinc finger, MYM-type 2 |
| ZNF331 | zinc finger protein 331 |
| ZNF384 | zinc finger protein 384 |
| ZNF521 | zinc finger protein 521 |
| ZNF668 | zinc finger protein 668 |
| ZRSR2 | zinc finger (CCCH type), RNA-binding motif and serine/arginine rich 2 |

In one aspect, the present disclosure provides kits for enriching amplicons comprising a concatemer of at least two or more copies of a target polynucleotide. Kits can comprise one or more elements disclosed herein in relation to any of the various aspects, in any combination. In some embodiments, the kit comprises: (a) a first primer comprising a first 3' end that specifically hybridizes to the target polynucleotide via sequence complementarity and a first 5' end comprising a first common sequence that does not specifically hybridize to the target polynucleotide via sequence complementarity; (b) a second primer comprising a second 3' end that specifically hybridizes to the concatemer via sequence complementarity and a second 5' end comprising a second common sequence that does not specifically hybridize to the concatemer via sequence complementarity, wherein the first common sequence and the second common sequence each comprise at least 10 contiguous nucleotides at a 5' end and are at least 90% identical when optimally aligned, and the concatemer is an extension product of the first primer; and (c) a third primer having a sequence that specifically hybridizes to the first common sequence or the second common sequence via sequence complementarity. Reagents and other materials in a kit may be contained in any suitable container, and may be in an immediately usable form or require combination with other reagents in the kit or reagents supplied by a user (e.g. dilution of a concentrated composition or reconstitution of a lyophilized composition). A kit may provide buffers, non-limiting examples of which include sodium carbonate buffer, a sodium bicarbonate buffer, a borate buffer, a Tris buffer, a MOPS buffer, a HEPES buffer, and combinations thereof. A kit may comprise a control sample, e.g., purified DNA for use as a positive control or quantification standard. In some embodiments, the kit comprises one or more enzymes for amplifying polynucleotides, such as one or more of a reverse transcriptase and a polymerase. Where desired, a subject kit can further comprise one or more detectable markers to enable monitoring of accumulation of amplification products, such as in real-time. Non-limiting examples of detectable markers are described above and include dyes, such as SYBR green dye or BEBO dye, that preferentially or exclusively bind to double stranded DNA during an amplification step. In some embodiments, the kit comprises a probe oligonucleotide that includes a fluorophore and quencher to detect the progress or products of an amplification reaction. In some embodiments, the kit comprises instructions for use of the kit in accordance with one or more methods disclosed herein. In some embodiments, the first common sequence and the second common sequence are identical. In some embodiments, the first common sequence, the second common sequence, and the hybridizing sequence of the third primer all have melting temperatures (Tm's) within ±5° C. of one another. In some embodiments, the combined length of sequence portions of the target polynucleotide corresponding to, from 5' to 3' along the target polynucleotide, (i) sequence complementary to the first 3' end, (ii) sequence identical to the second 3' end, and (iii) intervening sequence between (i) and (ii), is 75 nucleotides or less.

In one aspect, the present disclosure provides systems for designing primers for use in enriching amplicons comprising a concatemer of at least two or more copies of a target polynucleotide. The primers may comprise any of the features described herein, in relation to any of the various aspects of the disclosure. In some embodiments, the system comprises (a) a computer configured to receive a customer request to design primers for amplifying a specified target sequence; (b) computer readable medium comprising codes that, upon execution by one or more processors, design at least three primers for the amplification of the target sequence, wherein the at least three primers comprise: (i) a first primer comprising a first 3' end that specifically hybridizes to the target polynucleotide via sequence complementarity and a first 5' end comprising a first common sequence that does not specifically hybridize to the target polynucleotide via sequence complementarity; (ii) a second primer comprising a second 3' end that specifically hybridizes to the concatemer via sequence complementarity and a second 5' end comprising a second common sequence that does not specifically hybridize to the concatemer via sequence complementarity, wherein the first common sequence and the second common sequence each comprise at least 10 contiguous nucleotides at a 5' end and are at least 90% identical when optimally aligned, and the concatemer is an extension product of the first primer; and (iii) a third primer having a sequence that specifically hybridizes to the first common sequence or the second common sequence via sequence complementarity; and (c) a report generator that sends a report to a recipient, wherein the report contains sequences of the at least three primers. In some embodiments, the first common sequence and the second common sequence are identical. In some embodiments, the first common sequence, the second common sequence, and the hybridizing sequence of the third primer all have melting temperatures (Tm's) within ±5° C. of one another. In some embodiments, the combined length of sequence portions of the target polynucleotide corresponding to, from 5' to 3' along the target polynucleotide, (i) sequence complementary to the first 3' end, (ii) sequence identical to the second 3' end, and (iii) intervening sequence between (i) and (ii), is 75 nucleotides or less.

In some embodiments, the computer comprises one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules or techniques which, in turn, may be implemented in hardware, firmware, software, or any combination thereof. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. In some embodiments, the computer is configured to receive a customer request to design primers for amplifying a specified target sequence (which may also be provided by the customer). The computer may receive the customer request directly (e.g. by way of an input device such as a keyboard, mouse, or touch screen operated by the customer or a user entering a customer request) or indirectly (e.g. through a wired or wireless connection, including over the internet).

In some embodiments, the system comprises a report generator that sends a report to a recipient, wherein the report contains sequences of the at least three primers. The report generator may send a report automatically in response to the customer request. Alternatively, the report generator may send a report in response to instructions from an operator. The report may be transmitted to a recipient at a local or remote location using any suitable communication medium. For example, the communication medium can be a network connection, a wireless connection, or an internet connection. A report can be transmitted over such networks or connections (or any other suitable means for transmitting information, including but not limited to mailing a physical report, such as a print-out) for reception and/or for review by a recipient. The recipient can be but is not limited to the customer, or electronic system (e.g. one or more computers, and/or one or more servers). In some embodiments, the report generator sends the report to a recipient's device, such as a personal computer, phone, tablet, or other device. The report may be viewed online, saved on the recipient's device, or printed.

In one aspect, the disclosure provides a computer-readable medium comprising codes that, upon execution by one or more processors, implements a method according to any of the methods disclosed herein. Computer readable medium may take many forms, including but not limited to, a tangible storage medium, a carrier wave medium, or physical transmission medium. Non-volatile storage media include, for example, optical or magnetic disks, such as any of the storage devices in any computer(s) or the like, such as may be used to implement the calculation steps, processing steps, etc. Volatile storage media include dynamic memory, such as main memory of a computer. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Comparison of Products from One Cycle of RCA Amplification and Multiple Cycles of RCA Amplification Genomic DNA was sonicated to an average fragment size of approximately 180 bp. Fragmented DNA was purified with 0.9× Ampure beads to remove fragments smaller than 100 bp. Sonicated genomic DNA was then ligated to form circular target polynucleotides. For ligation, 12 µl of purified DNA fragments (>10 ng) was denatured by heating at 95° C. for 30 seconds and chilling on ice for 2 minutes. Then, 8 µl of ligation mix containing 2 µl of 10× CircLigase buffer, 4 µl of 5M Betaine, 1 µl of 50 mM $MnCl_2$, and 1 µl of CircLigase II was added to the denatured DNA samples and the reactions are incubated at 60° C. for at least 12 hours. At the end the of ligation process, remaining linear single stranded DNA molecules were removed by an exonuclease treatment step. For exonuclease treatment, ligation products were heated at 80° C. for 45 seconds and following that was the addition of 1 µl of exonuclease mix (ExoI 20 U/µl: ExoIII 100 U/µl, at 1:2 ratio). The sample was incubated on a thermal cycler at 37° C. for 30 minutes and then at 80° C. for 20 minutes. After exonuclease treatment, 1 µl of 50 mM EDTA was added to each tube.

Circular target polynucleotides were subject to one cycle of RCA amplification or multiple RCA amplification. For both one cycle of RCA amplification and multiple cycles of RCA amplification, 10 ng of circularized DNA samples was used as starting material. For each reaction, 0.34 uL of 1M Tris-HCl (pH9.2), 1 µl of 100 mM MgSO4, 2.78 µl of 180 mM (NH4)2SO4, 0.75 uL of dNTP mix (25 mM each), 0.5 µl of 10% Tween 20, 1.20 µl of 1M KCl, 2 µl of 10 µM back-to-back forward and reverse primers, 18.28 µl of water was added to each 10 ng of DNA samples. The reactions were heated at 80° C. for 1 minute and incubated at 63° C. for 5 minutes before cooling down to 4° C. Next, 15 units of Bst 2.0 warm start DNA polymerase was added to each reaction. For one cycle of RCA amplification, the reaction was incubated at 63° C. for 2 hours. For multiple cycles of RCA amplification, the reaction was incubated in a thermal cycler with the following program: 8 cycles of 60° C. for 30 seconds; 70° C. for 4.5 minutes; 94° C. for 20 seconds; and 58° C. for 10 seconds. At the end of every two cycles, 15 units of Bst 2.0 warm start DNA polymerase was added.

All amplification products were purified by addition of 50 µl Ampure beads, following the manufacturer's instructions for the remaining wash steps. For elution, 55 µl of elution buffer was added to each tube and the beads were incubated at 65° C. for 5 minutes. After spinning briefly, the tubes were returned to the magnets. About 50 µl of eluted product was recovered from each reaction.

For adaptor attachment of the amplification products from one cycle of RCA, each 50 µl of eluent was mixed with 5.7 µl of 10× AccuPrime buffer, 1 µl of 25 µM adaptor primers that were complementary to common sequences at the 3' end of the primers used in the previous amplification reaction, and 2 units of AccuPrime HiFi Taq polymerase. Adaptors were attached by amplification using the following PCR program: 95° C. for 2 minutes; 30 cycles of 95° C. for 30 seconds, 60° C. for 30 seconds, 72° C. for 2.5 minutes; and final extension at 72° C. for 7 minutes. For amplification products from multiple cycles of RCA, sequencing adaptors were attached using KAPA hyper prep kits for Illumina. PCR amplified library products were analyzed by agarose gel or next-generation sequencing. For performing bioinformatics on sequencing data, FASTQ files were obtained from a HiSeq run. The FASTQ files were aligned to a reference file containing the target sequence. Insert size was calculated based on sequencing data.

Figure 5:
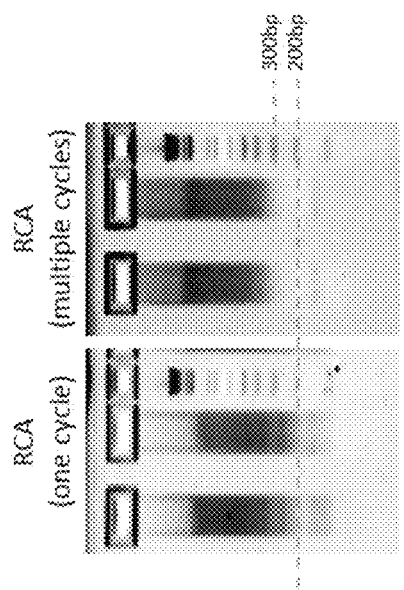
FIG. 5 shows the size distribution of amplification products generated by one cycle of rolling circle amplification and multiple cycles of rolling circle amplification by agarose gel.

Amplification with B2B primers and temperature cycling resulted in amplicons containing more polynucleotide copies, as well as amplicons with longer target polynucleotides compared to one cycle of RCA as shown qualitatively in the agarose gel of FIG. 5. In FIG. 6, the table provides a semi-quantitative comparison of the ratio of products containing one repeat (~150 bp in size), two repeats (~300 bp) or 3 repeats (~450 bp) by intentisity analysis of the agarose gel. Compared to one cycle of RCA, multiple cycles of RCA reduced the relative amount of products with only 1 repeat.

Figure 7:
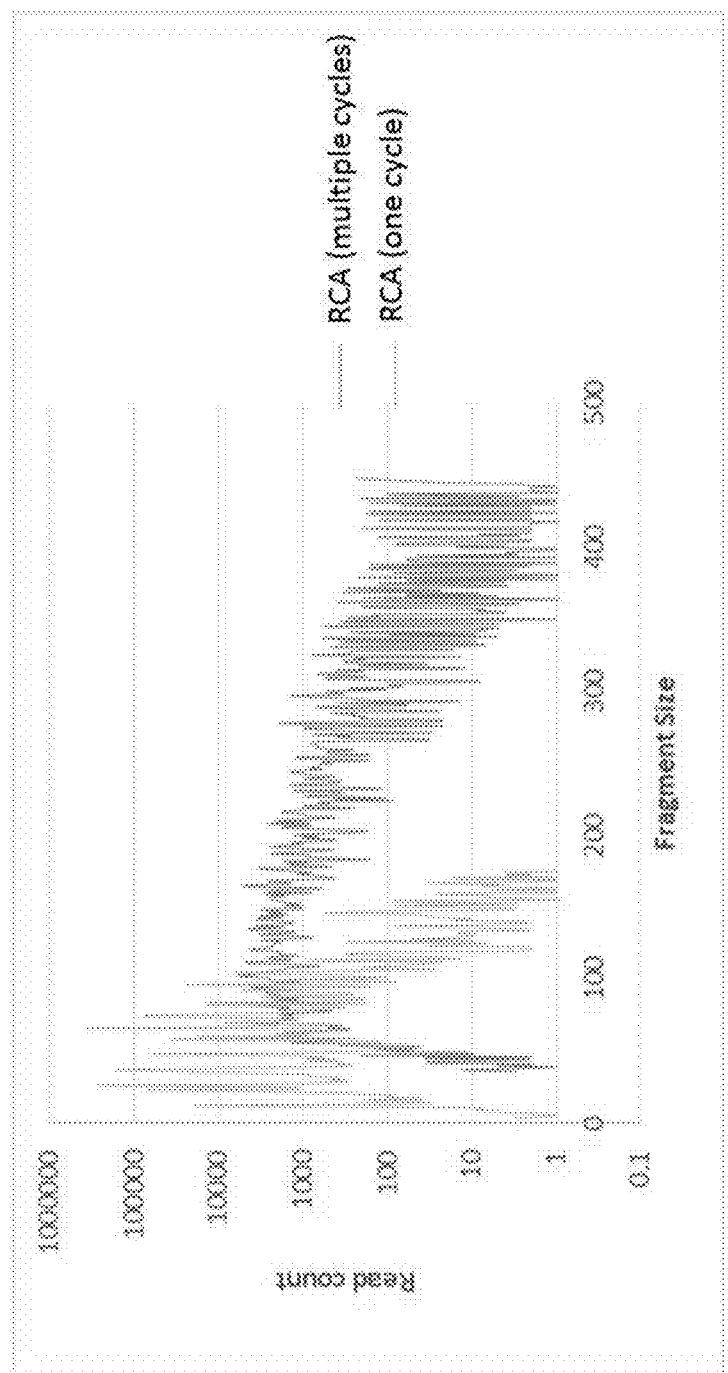
FIG. 7 illustrates the size distribution of individual repeat elements in exemplary rolling circle amplification reactions comprising one cycle and multiple cycles.
Figure 8:
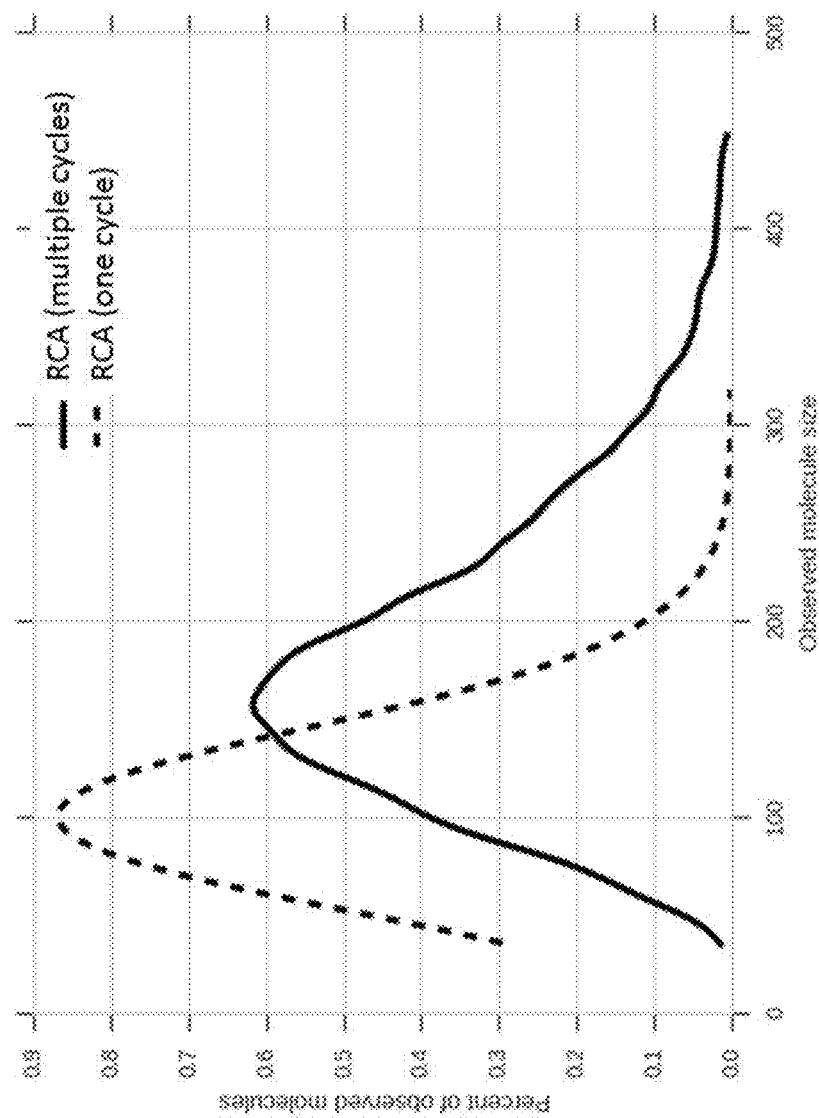
FIG. 8 shows fragment size distribution of sequenced targets generated by one cycle of rolling circle amplification and multiple cycles of rolling circle amplification.

Sequencing analysis of amplification products also demonstrates an increased proportion of larger DNA fragments when using multiple cycles of RCA as compared to one cycle of RCA. FIG. 7 shows a distribution of fragment size by read counts and FIG. 8 shows a distribution of observed molecule size by percentage of molecules.

Example 2: Comparison of Products from Multiple Cycles of RCA Using Either Primers with a Stem Structure or Primers without a Stem Structure Genomic DNA was sonicated to an average fragment size of approximately 150 bp. Fragmented DNA was purified with 0.9× Ampure beads to remove fragments smaller than 100 bp. Sonicated genomic DNA was then ligated to form circular target polynucleotides. For ligation, 12 µl of purified DNA fragments (>10 ng) was denatured by heating at 95° C. for 30 seconds and chilling on ice for 2 minutes. Then, 8 µl of ligation mix containing 2 µl of 10× CircLigase buffer, 4 µl of 5M Betaine, 1 µl of 50 mM MnCl2, and 1 µl of CircLigase II was added to the denatured DNA samples and the reactions are incubated at 60° C. for at least 12 hours. At the end the of ligation process, remaining linear single stranded DNA molecules were removed by an exonuclease treatment step. For exonuclease treatment, ligation products were heated at 80° C. for 45 seconds and following that was the addition of 1 µl of exonuclease mix (ExoI 20 U/µl: ExoIII 100 U/µl, at 1:2 ratio). The sample was incubated on a thermal cycler at 37° C. for 30 minutes and then at 80° C. for 20 minutes. After exonuclease treatment, 1 µl of 50 mM EDTA was added to each tube.

Circular target polynucleotides were subject to multiple cycles of RCA amplification using primers capable of forming a 19mer stem structure or primers designed without a stem structure. Exemplary common sequences capable of forming stem structures include those provided in Table 1 and any fragment thereof.

For each reaction, 0.34 uL of 1M Tris-HCl (pH9.2), 1 µl of 100 mM MgSO4, 2.78 µl of 180 mM (NH4)2SO4, 0.75 uL of dNTP mix (25 mM each), 0.5 µl of 10% Tween 20, 1.20 µl of 1M KCl, 2 µl of 10 µM back-to-back forward and reverse primers, 18.28 µl of water was added to each 10 ng of DNA samples. The reactions were heated at 80° C. for 1 minute and incubated at 63° C. for 5 minutes before cooling down to 4° C. Next, 15 units of Bst 2.0 warm start DNA polymerase was added to each reaction. The reactions were incubated in a thermal cycler with the following program: 8 cycles of 60° C. for 30 seconds; 70° C. for 4.5 minutes; 94° C. for 20 seconds; and 58° C. for 10 seconds. At the end of every two cycles, 15 units of Bst 2.0 warm start DNA polymerase was added.

All amplification products were purified by addition of 50 µl Ampure beads, following the manufacturer's instructions for the remaining wash steps. For elution, 55 µl of elution buffer was added to each tube and the beads were incubated at 65° C. for 5 minutes. After spinning briefly, the tubes were returned to the magnets. About 50 µl of eluted product was recovered from each reaction.

Sequencing adaptors were attached using KAPA hyper prep kits for Illumina. PCR amplified library products were analyzed by agarose gel and products in size range 550 bp-1000 bp were further collected for sequencing. The resulting amplification products were analyzed by sequencing. For performing bioinformatics on sequencing data, FASTQ files were obtained from a HiSeq run. The FASTQ files were aligned to a reference file containing the target sequence. Insert size was calculated based on sequencing data.

Amplification with B2B primers containing a stem structure and temperature cycling resulted in amplicons containing more polynucleotide copies as shown in Table 3. Table 3 lists the percentage of sequencing reads containing more than one repeat. Compared no stem primer, amplification using primers with a 19 base stem significantly increased the percentage of reads with more than one repeat.

TABLE 3

| Primers used for RCA | % of reads with repeats |
| --- | --- |
| Primers with 19mer stem | 64.62% |
| Primers without stem | 31.49% |

Example 3: Detecting Low-Frequency Fusion Allele from Mixed Genomic DNA Samples Chromosome rearrangements are observed in many cancer types. This example describes a method for detecting a fusion allele using circularized DNA molecules and back-to-back (B2B) primer design. This method enables fusion detection from DNA samples without prior knowledge of the 'partner' gene and can be applied for screening gene rearrangement events in cell free DNA or genomic DNA samples.

Genomic DNA from an EML4/ALK DNA standard reference (HD664 Horizon Diagnostics) containing 50% EML4/ALK fusion allele and a reference genomic DNA were sonicated to an average fragment size of approximately 150 bp. Fragmented DNA was purified with 0.9× Ampure beads to remove fragments that were smaller than 100 bp. For ligation, 12 µl of purified DNA fragments (>10 ng) was denatured by heating at 95° C. for 30 seconds and chilling on ice for 2 minutes. Then, 8 µl of ligation mix containing 2 µl of 10× CircLigase buffer, 4 µl of 5M Betaine, 1 µl of 50 mM $MnCl_2$, and 1 µl of CircLigase II was added to the denatured DNA samples and the reactions were incubated at 60° C. for at least 12 hours. At the end of the ligation process, remaining linear single stranded DNA molecules was removed by an exonuclease treatment step. For exonuclease treatment, ligation products were heated at 80° C. for 45 seconds, followed by addition of 1 µl of exonuclease mix (ExoI 20 U/µl: ExoIII 100 U/µl, at a 1:2 ratio) and incubated on a thermal cycle at 37° C. for 30 minutes and then at 80° C. for 20 minutes. After exonuclease treatment, 1 µl of 50 mM EDTA was added to each tube.

Sonicated genomic DNA was then ligated to form circular target polynucleotides. The two circularized DNA samples, HD664 and reference genomic DNA, were quantified by qPCR before mixing together to achieve 2.5%, 0.5%, 0.05% and 0% of fusion allele based on concentration (FIG. 9). For rolling circle amplification, 10 ng of each mixed DNA samples was used as starting material. For each reaction, 0.34 µl of 1M Tris-HCl (pH 9.2), 1 µl of 100 mM MgSO4, 2.78 µl of 180 mM (NH4)2SO4, 0.75 µl of dNTP mix (25 mM each), 0.5 µl of 10% Tween 20, 1.20 µl of 1M KCl, 2 µl of 10 µM forward and reverse primers designed specifically to target the ALK/EML4 fusion region (primer sequences provided in Table 4), 18.28 µl of water were added to each 10 ng of DNA samples. The reactions were heated at 80° C. for 1 minute and incubated at 63° C. for 5 minutes before cooling down to 4° C. To each reaction was added 15 units of Bst 2.0 warm start DNA polymerase, and each reaction was then incubated at 63° C. for 2 hours.

TABLE 4

Forward and reverse primer sequences for ALK fusion detection

| Oligo name | Oligo Sequences | SEQ ID NOS |
| --- | --- | --- |
| HD664_ALK_F | CCTTGGCACCCGAGAATTCCATTTGAGGGATGGCA CCATAT | 22 |
| HD664_ALK_R | GTTCAGAGTTCTACAGTCCGACGATCGGGACAGGA TAATAGGAGCTAACA | 23 |

Amplification products were purified by addition of 50 µl Ampure beads, following the manufacturer's instructions for the remaining wash steps. For elution, 55 µl elution buffer was added to each tube and the beads were incubated at 65° C. for 5 minutes. After spinning briefly, the tubes were returned to the magnets. About 50 µl of eluted product was recovered from each reaction. Each 50 µl of eluent was mixed with 5.7 µl of 10× AccuPrime buffer, 1 µl of 25 uM of each Illumina sequencing library adaptor primers and 2 units of AccuPrime HiFi Taq polymerase. Adapter attachment by amplification used the following PCR program: 95° C. for 2 minutes; 25 cycles of 95° C. for 30 seconds, 60° C. for 30 seconds, 72° C. for 2.5 minutes; and final extension at 72° C. for 7 minutes. PCR products were analyzed by agarose gel and products in size range 550 bp-1000 bp were collected for sequencing.

Figure 10:
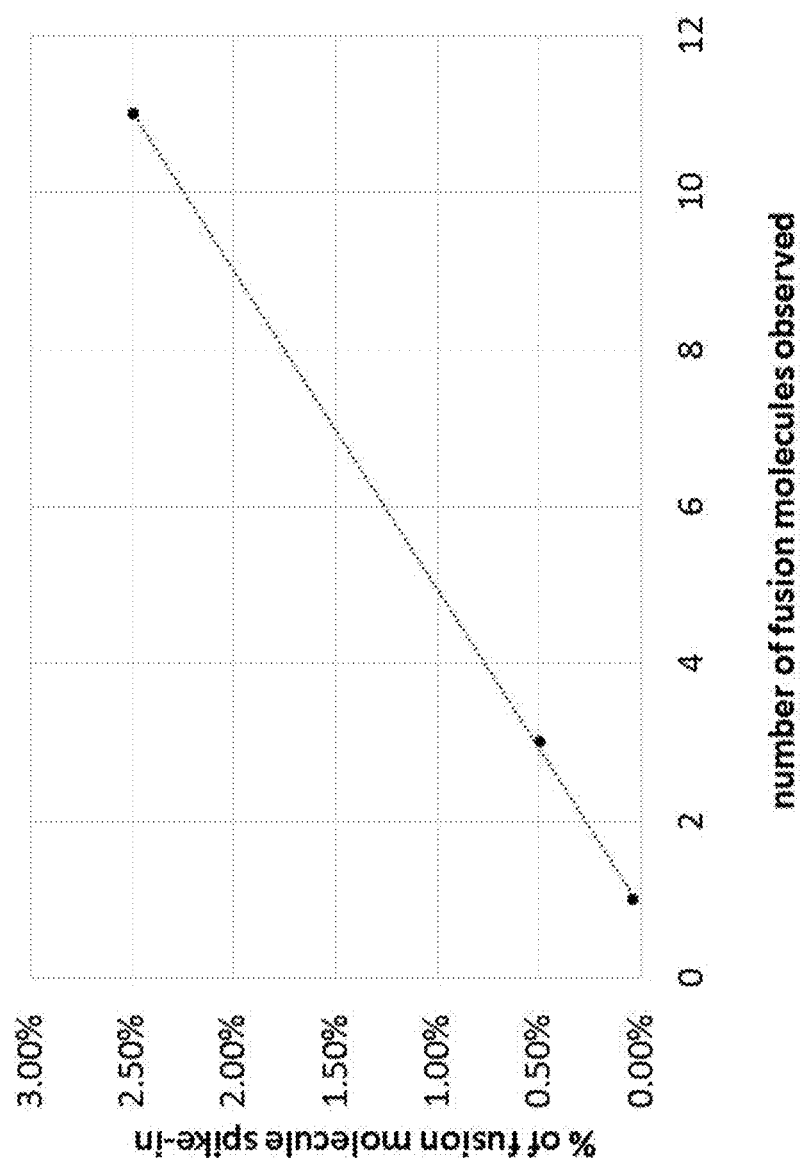
FIG. 10 illustrates fusion allele detection in accordance with an embodiment.

For performing bioinformatics on sequencing data, FASTQ files were obtained from a HiSeq run. The FASTQ files were aligned to a reference file containing the target sequence. The fusion allele was found in samples with 2.5%, 0.5% or 0.05% fusion allele spike-in, but was not found in the sample with 0% fusion allele spike-in as shown in FIG. 10.

Example 4: Detection of Targets in a Multiplex RCA with B2B Primers

Constituent target polynucleotides of a plurality of target polynucleotides in a sample were detected in multiple RCA and amplification with B2B primers. 20 ng of a control cfDNA extracted from human serum sample (H6914, Sigma) was re-suspended in total of 12 µl of Tris pH 8 buffer and was denatured by heating at 95° C. for 30 seconds and chilled on ice for 2 minutes. Then, 8 µl of ligation mix containing 2 µl of 10× CircLigase buffer, 4 µl of 5M Betaine, 1 µl of 50 mM $MnCl_2$, and 1 µl of CircLigase II was added to the denatured DNA samples and the reactions were incubated at 60° C. for at least 12 hours. At the end the of ligation process, remaining linear single stranded DNA molecules were removed by an exonuclease treatment step. For exonuclease treatment, ligation products were heated at 80° C. for 45 seconds, followed by the addition of 1 µl of exonuclease mix (ExoI 20 U/µl: ExoIII 100 U/µl, at 1:2 ratio). The sample was incubated on a thermal cycler at 37° C. for 30 minutes and then at 80° C. for 20 minutes. After exonuclease treatment, 1 µl of 50 mM EDTA was added to each tube.

Circular target polynucleotides were subjected to rolling circle amplification followed by amplification with B2B primers. Examples of B2B primers are provided in Table 5.

TABLE 5

Examples of back-to-back B2B primers

| Gene Name | B2B Forward Primer Name | Forward Primer Sequence | SEQ ID NOS | B2B Reverse Primer Name | Reverse Primer Sequence | SEQ ID NOS |
|---|---|---|---|---|---|---|
| BRAF | BRAF-BX1a | GTTCAGAGTTCTACAGTCCGACGATCCAGTTTGAACAGTTGTCTGGATC | 24 | BRAF-BX1b | CCTTGGCACCCGAGAATTCCAAAACTGATGGGACCCACTCC | 25 |
| CYP2 | CYP2c19-BXc | GTTCAGAGTTCTACAGTCCGACGATCTTCCCACTATCATTGATTATTTCC | 26 | CYP2c19-BXd | CCTTGGCACCCGAGAATTCCATGGGAAAATTATTGCATATCTAAGAG | 27 |
| EGFR | EGFR-BX1a | GTTCAGAGTTCTACAGTCCGACGATCCTTTCTCACCTTCTGGGATCC | 28 | EGFR-BX1b | CCTTGGCACCCGAGAATTCCAAAATTCCCGTCGCTATCAAG | 29 |
| EGFR | EGFR-BX2a | GTTCAGAGTTCTACAGTCCGACGATCCCATCACGTAGGCTTCCTG | 30 | EGFR-BX2b | CCTTGGCACCCGAGAATTCCAATGGCCAGCGTGGACAAC | 31 |
| EGFR | EGFR-BX3a | GTTCAGAGTTCTACAGTCCGACGATCGACATAGTCCAGGAGGCAGC | 32 | EGFR-BX3b | CCTTGGCACCCGAGAATTCCATGTCCGGGAACACAAAGAC | 33 |
| EGFR | EGFR-BX4a | GTTCAGAGTTCTACAGTCCGACGATCAAGCGACGGTCCTCCAAG | 34 | EGFR-BX4b | CCTTGGCACCCGAG AATTCCATGGCAGCCAGGAACGTAC | 35 |
| EGFR | EGFR-BX5a | GTTCAGAGTTCTACAGTCCGACGATCAGTACGTTCCTGGCTGCC | 36 | EGFR-BX5b | CCTTGGCACCCGAGAATTCCAAACACCGCAGCATGTCAAG | 37 |
| EGFR | EGFR-BX6a | GTTCAGAGTTCTACAGTCCGACGATCATCCACTTGATAGGCACCTTG | 38 | EGFR-BX6b | CCTTGGCACCCGAGAATTCCAAAGTGGATGGCATTGGAATC | 39 |
| EGFR | EGFR-BX7a | GTTCAGAGTTCTACAGTCCGACGATCTCTCGCTGGCAGGGATTC | 40 | EGFR-BX7b | CCTTGGCACCCGAGAATTCCACCTGGAGAAAGGAGAACGC | 41 |
| EGFR | EGFR-BX9a | GTTCAGAGTTCTACAGTCCGACGATCAACTTTGGGCGACTATCTGC | 42 | EGFR-BX9b | CCTTGGCACCCGAGAATTCCAAGTTCCGTGAGTTGATCATCG | 43 |
| EGFR | EGFR-BX10a | GTTCAGAGTTCTACAGTCCGACGATCTTGGAGTCTGTAGGACTTGGC | 44 | EGFR-BX10b | CCTTGGCACCCGAGAATTCCAACTTCTACCGTGCCCTGATG | 45 |
| EGFR | EGFR-BX11a | GTTCAGAGTTCTACAGTCCGACGATCCTGCTGTGGGATGAGGTACTC | 46 | EGFR-BX11b | CCTTGGCACCCGAGAATTCCACACAGCAGGGCTTCTTCAG | 47 |
| EGFR | EGFR-BX12a | GTTCAGAGTTCTACAGTCCGACGATCCATGGAATGCTTGTACCACATC | 48 | EGFR-BX12b | CCTTGGCACCCGAGAATTCCACATGGGCAACTTCTCTGTTTC | 49 |
| EGFR | EGFR-BX4c | GTTCAGAGTTCTACAGTCCGACGATCCTGGCAGCCAGGAACGTACT | 50 | EGFR-BX4d | CCTTGGCACCCGAGAATTCCACGACGGTCCTCCAAGTAGTTC | 51 |

TABLE 5-continued

Examples of back-to-back B2B primers

| Gene Name | B2B Forward Primer Name | Forward Primer Sequence | SEQ ID NOS | B2B Reverse Primer Name | Reverse Primer Sequence | SEQ ID NOS |
|---|---|---|---|---|---|---|
| EGFR | EGFR-BX5c | GTTCAGAGTTCTACAGTCCGACGATCACACCGCAGCATGTCAAGATC | 52 | EGFR-BX5d | CCTTGGCACCCGAGAATTCCAAGTACGTTCCTGGCTGCCAG | 53 |
| EGFR | EGFR_hot1-BXc | GTTCAGAGTTCTACAGTCCGACGATCGCACGGTGTATAAGGTAAGGTCC | 54 | EGFR_hot1-BXd | CCTTGGCACCCGAGAATTCCAGAATTCAGTTTCCTTCAAGATCC | 55 |
| KRAS | KRAS-BX1a | GTTCAGAGTTCTACAGTCCGACGATCAAGAGTGCCTTGACGATACAGC | 56 | KRAS-BX1b | CCTTGGCACCCGAGAATTCCATCTTGCCTACGCCACCAG | 57 |
| KRAS | KRAS_c181-BXc | GTTCAGAGTTCTACAGTCCGACGATCTCGAGAATATCCAAGAGACAGG | 58 | KRAS_c181-BXd | CCTTGGCACCCG AG AATTCCAAGAGGAGTACAGTGCAATGAGG | 59 |
| PIK3CA | PIK3CA-BX1a | GTTCAGAGTTCTACAGTCCGACGATCGCTTTGAGCTGTTCTTTGTCATT | 60 | PIK3CA-BX1b | CCTTGGCACCCGAGAATTCCAAAAGCAATTTCTACACGAGATCC | 61 |
| PIK3CA | PIK3CA-BX2a | GTTCAGAGTTCTACAGTCCGACGATCTTTAATTGTGTGGAAGATCCAATC | 62 | PIK3CA-BX2b | CCTTGGCACCCGAGAATTCCAATTAAACAGCATGCATTGAACTG | 63 |
| PIK3CA | PIK3CA-BX1c | GTTCAGAGTTCTACAGTCCGACGATCCCTCTCTCTGAAATCACTGAGC | 64 | PIK3CA-BX1d | CCTTGGCACCCGAGAATTCCAGAGGATCTCGTGTAGAAATTGC | 65 |
| PTEN | PTEN-BX1a | GTTCAGAGTTCTACAGTCCGACGATCTGTTTCTGCTAACGATCTCTTTG | 66 | PTEN-BX1b | CCTTGGCACCCGAGAATTCCAAGGAGATATCAAGAGGATGGATTC | 67 |
| PTEN | PTEN-BX2a | GTTCAGAGTTCTACAGTCCGACGATCCAGGAAATCCCATAGCAATAATG | 68 | PTEN-BX2b | CCTTGGCACCCGAGAATTCCATCCTGCAGAAAGACTTGAAGG | 69 |
| PTEN | PTEN-BX3a | GTTCAGAGTTCTACAGTCCGACGATCGCTTTGAATCCAAAAACCTTAAAAC | 70 | PTEN-BX3 b | CCTTGGCACCCGAGAATTCCAGGATTCAAAGCATAAAAACCATTAC | 71 |
| PTEN | PTEN-BX3c | GTTCAGAGTTCTACAGTCCGACGATCGGATTCAAAGCATAAAAACCATTAC | 72 | PTEN-BX3d | CCTTGGCACCCGAGAATTCCAGCTTTGAATCCAAAAACCTTAAAC | 73 |
| PTEN | PTEN-BX15c | GTTCAGAGTTCTACAGTCCGACGATCGATGTTAGTGACAATGAACCTGATC | 74 | PTEN-BX15d | CCTTGGCACCCGAGAATTCCATGGTGTTACAGAAGTTGAACTGC | 75 |

TABLE 5-continued

Examples of back-to-back B2B primers

| Gene Name | B2B Forward Primer Name | Forward Primer Sequence | SEQ ID NOS | B2B Reverse Primer Name | Reverse Primer Sequence | SEQ ID NOS |
|---|---|---|---|---|---|---|
| TP53 | TP53-BX1a | GTTCAGAGTTCTACAGTCCGACGATCCCTGACTCAGACTGACATTCTCC | 76 | TP53-BX1b | CCTTGGCACCCGAGAATTCCACAGGCCCTTCTGTCTTGAAC | 77 |
| TP53 | TP53-BX2a | GTTCAGAGTTCTACAGTCCGACGATCATGTTCCGAGAGCTGAATGAG | 78 | TP53-BX2b | CCTTGGCACCCGAGAATTCCAGAACATCTCGAAGCGCTCAC | 79 |
| TP53 | TP53-BX3a | GTTCAGAGTTCTACAGTCCGACGATCTTAAAGGACCAGACCAGCTTTC | 80 | TP53-BX3b | CCTTGGCACCCGAGAATTCCATTATGGTATAAGTTGGTGTTCTGAAG | 81 |
| TP53 | TP53-BX3c | GTTCAGAGTTCTACAGTCCGACGATCTTATGGTATAAGTTGGTGTTCTGAAG | 82 | TP53-BX3d | CCTTGGCACCCGAGAATTCCATTAAAGGACCAGACCAGCTTTC | 83 |
| TP53 | TP53-BX16c | GTTCAGAGTTCTACAGTCCGACGATCGCTCGACGCTAGGATCTGAC | 84 | TP53-BX16d | CCTTGGCACCCGAGAATTCCACTCTGAGTCAGGAAACATTTTCAG | 85 |

Figure 11:
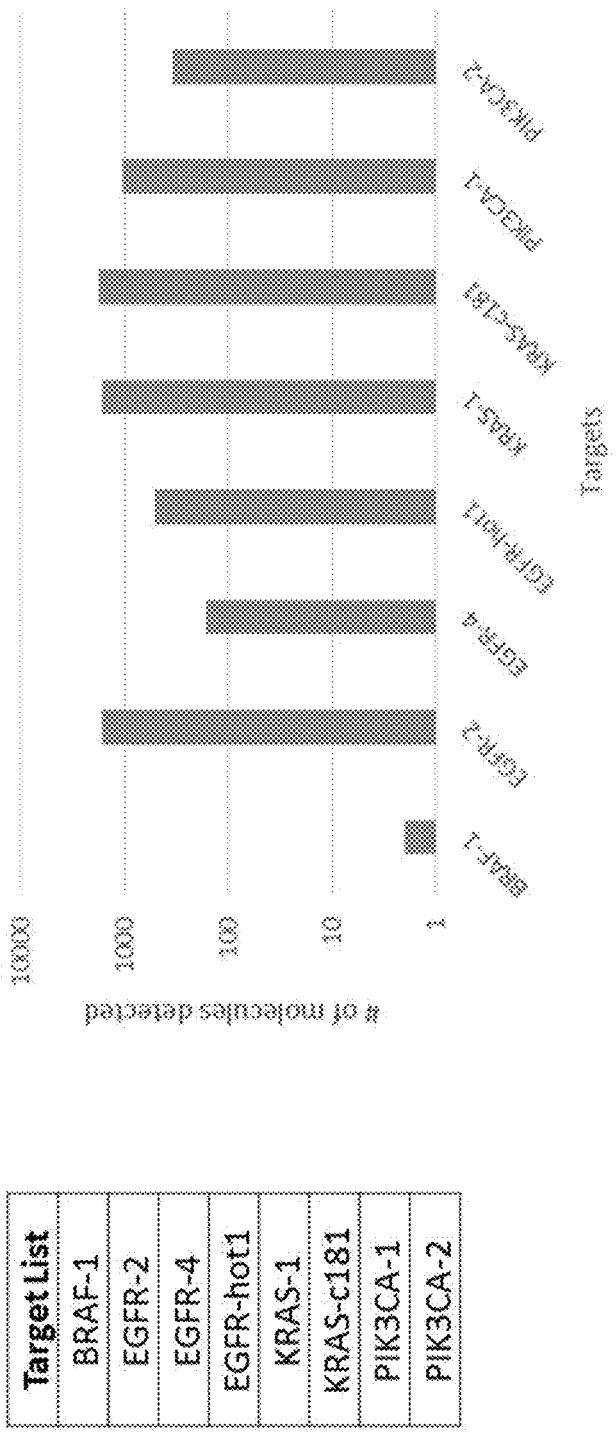
FIG. 11 illustrates that multiple target polynucleotide sequences are detectable in a multiplex reaction in accordance with an embodiment.

For this reaction, 0.34 µl of 1M Tris-HCl (pH9.2), 1 µl of 100 mM MgSO4, 2.78 µl of 180 mM (NH4)2SO4, 0.75 µl of dNTP mix (25 mM each), 0.5 µl of 10% Tween 20, 1.20 µl of 1M KCl, 2 µl of 10 µM back-to-back forward and reverse primers (a mixture of 8 paired primers targeting specific targets listed in the Target List table of FIG. 11), 18.28 µl of water was added to each 10 ng of DNA samples. The reactions were heated at 80° C. for 1 minute and incubated at 63° C. for 5 minutes before cooling down to 4° C. Next, 15 units of Bst 2.0 warm start DNA polymerase was added to each reaction. For isothermal amplification with B2B primers, the reaction was incubated at 63° C. for 2 hours.

All amplification products were purified by addition of 50 µl Ampure beads, following the manufacturer's instructions for the remaining wash steps. For elution, 55 µl of elution buffer was added to each tube and the beads were incubated at 65° C. for 5 minutes. After spinning briefly, the tubes were returned to the magnets. About 50 µl of eluted product was recovered from each reaction.

For adaptor attachment, each 50 µl of eluent was mixed with 5.7 µl of 10× AccuPrime buffer, 1 µl of 25 µM adaptor primers that are complementary to common sequences at the 3' end of the primers used in isothermal and B2B amplification, and 2 units of AccuPrime HiFi Taq polymerase. Adaptors were attached by amplification using the following PCR program: 95° C. for 2 minutes; 30 cycles of 95° C. for 30 seconds, 60° C. for 30 seconds, 72° C. for 2.5 minutes; and final extension at 72° C. for 7 minutes. PCR products were analyzed by agarose gel and products in size range 550 bp-1000 bp were further collected for sequencing. The resulting amplification products were analyzed by sequencing. Sequence analysis results as shown in FIG. 11 show that multiple target polynucleotide sequences are detectable in a multiplex reaction.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of nucleic acid processing, comprising:
(a) providing a reaction mixture comprising: (i) a polymerase, (ii) a circular polynucleotide; and (iii) a plurality of primers;
(b) in said reaction mixture, subjecting said circular polynucleotide to more than one cycle of amplification using said polymerase and said plurality of primers to generate a plurality of amplification products each amplification product of said plurality of amplification products comprising more than one copy of a sequence of said circular polynucleotide, wherein each cycle of amplification comprises:
annealing a primer of said plurality of primers to said circular polynucleotide at an annealing temperature;
performing a primer elongation reaction at an elongation temperature; and
subjecting said reaction mixture or derivative thereof to denaturation at a denaturation temperature; and
(c) subjecting said plurality of amplification products to nucleic acid sequencing to identify said sequence of said circular polynucleotide.

2. The method of claim 1, wherein said circular polynucleotide is a circularized cell-free nucleic acid.

3. The method of claim 1, wherein said circular polynucleotide is a circularized ribonucleic acid (RNA).

4. The method of claim 3, wherein said circularized RNA comprises messenger RNA (mRNA) or micro-RNA (miRNA).

5. The method of claim 1, wherein said circular polynucleotide is a circularized deoxyribonucleic acid (DNA).

6. The method of claim 1, wherein said circular polynucleotide is derived from a biological sample from a subject.

7. The method of claim 6, wherein said biological sample is a cell-free biological sample.

8. The method of claim 6, wherein said biological sample is serum, plasma, blood, perspiration, saliva, urine, stool, semen, mucosal excretions, spinal fluid, amniotic fluid, or lymph fluid.

9. The method of claim 1, wherein said circular polynucleotide is single stranded.

10. The method of claim 1, wherein said denaturation temperature is different from said annealing temperature and said elongation temperature.

11. The method of claim 10, wherein said denaturation temperature is between about 75° C. and about 95° C.; said annealing temperature is between about 45° C. and about 65° C.; and said elongation temperature is between about 65° C. and about 75° C.

12. The method of claim 1, wherein said primer comprises a random sequence.

13. The method of claim 1, wherein said primer comprises a gene specific sequence.

14. The method of claim 1, wherein said primer comprises a barcode sequence.

15. The method of claim 1, wherein said primer comprises an adaptor sequence.

16. The method of claim 1, further comprising processing said sequence of said circular polynucleotide to identify a variant in said sequence.

17. The method of claim 16, wherein said variant comprises at least one of a single nucleotide polymorphism, a deletion, an insertion, a copy number variant, a duplication, a translocation, a fusion, or a epigenetic variant.

18. The method of claim 16, wherein said variant is associated with a disease in a subject.

19. The method of claim 18, wherein said disease is cancer.

20. The method of claim 16, further comprising processing said sequence variant to select a treatment for a disease.

21. The method of claim 16, further comprising processing said sequence variant to monitor disease progression in a subject.

22. The method of claim 1, wherein said polymerase has strand displacement activity.

* * * * *